United States Patent
Jatsch et al.

(10) Patent No.: US 10,934,292 B2
(45) Date of Patent: Mar. 2, 2021

(54) HEXAMETHYLINDANES

(71) Applicant: Merck Patent GmbH, Darmstadt (DE)

(72) Inventors: Anja Jatsch, Frankfurt am Main (DE); Philipp Stoessel, Frankfurt am Main (DE); Amir Hossain Parham, Frankfurt am Main (DE); Tobias Grossmann, Darmstadt (DE); Jonas Valentin Kroeber, Frankfurt am Main (DE); Thomas Eberle, Landau (DE); Herwig Buchholz, Frankfurt am Main (DE)

(73) Assignee: Merck Patent GmbH, Darmstadt (DE)

( * ) Notice: Subject to any disclaimer, the term of this patent is extended or adjusted under 35 U.S.C. 154(b) by 399 days.

(21) Appl. No.: 15/751,735

(22) PCT Filed: Jul. 14, 2016

(86) PCT No.: PCT/EP2016/001225
§ 371 (c)(1),
(2) Date: Feb. 9, 2018

(87) PCT Pub. No.: WO2017/025166
PCT Pub. Date: Feb. 16, 2017

(65) Prior Publication Data
US 2020/0140440 A1 May 7, 2020

(30) Foreign Application Priority Data
Aug. 13, 2015 (EP) .................................... 15180942

(51) Int. Cl.
| | | |
|---|---|---|
| *H01L 51/50* | (2006.01) |
| *C07D 487/04* | (2006.01) |
| *C07D 209/94* | (2006.01) |
| *C07D 265/34* | (2006.01) |
| *C07D 401/10* | (2006.01) |
| *C07D 401/14* | (2006.01) |
| *C07D 403/04* | (2006.01) |
| *C07D 403/10* | (2006.01) |
| *C07D 403/14* | (2006.01) |
| *C07D 405/12* | (2006.01) |
| *C07D 405/14* | (2006.01) |
| *C07D 409/10* | (2006.01) |
| *C07D 409/12* | (2006.01) |
| *C07D 409/14* | (2006.01) |
| *C07D 413/10* | (2006.01) |
| *C07D 417/10* | (2006.01) |
| *C07D 491/048* | (2006.01) |
| *C07D 491/107* | (2006.01) |
| *C07D 498/04* | (2006.01) |
| *H01L 51/00* | (2006.01) |

(52) U.S. Cl.
CPC ......... *C07D 487/04* (2013.01); *C07D 209/94* (2013.01); *C07D 265/34* (2013.01); *C07D 401/10* (2013.01); *C07D 401/14* (2013.01); *C07D 403/04* (2013.01); *C07D 403/10* (2013.01); *C07D 403/14* (2013.01); *C07D 405/12* (2013.01); *C07D 405/14* (2013.01); *C07D 409/10* (2013.01); *C07D 409/12* (2013.01); *C07D 409/14* (2013.01); *C07D 413/10* (2013.01); *C07D 417/10* (2013.01); *C07D 491/048* (2013.01); *C07D 491/107* (2013.01); *C07D 498/04* (2013.01); *H01L 51/0059* (2013.01); *H01L 51/0067* (2013.01); *H01L 51/0069* (2013.01); *H01L 51/0072* (2013.01); *H01L 51/0073* (2013.01); *H01L 51/0074* (2013.01); *H01L 51/5056* (2013.01); *H01L 51/5072* (2013.01); *H01L 51/5092* (2013.01); *H01L 51/5096* (2013.01)

(58) Field of Classification Search
None
See application file for complete search history.

(56) References Cited

U.S. PATENT DOCUMENTS

| | | | |
|---|---|---|---|
| 2012/0068170 A1 | 3/2012 | Pflumm et al. | |
| 2015/0171348 A1 | 6/2015 | Stoessel et al. | |
| 2015/0263297 A1* | 9/2015 | Stoessel ............. | C08G 73/0694 252/301.16 |
| 2019/0386226 A1 | 12/2019 | Parham et al. | |

FOREIGN PATENT DOCUMENTS

| | | |
|---|---|---|
| CN | 102448946 A | 5/2012 |
| CN | 104520308 A | 4/2015 |
| KR | 20140105634 A | 9/2014 |
| WO | WO-2014023377 A2 | 2/2014 |
| WO | WO-2015051869 A1 | 4/2015 |
| WO | WO-2015070944 A1 | 5/2015 |

OTHER PUBLICATIONS

International Search Report for PCT/EP2016/001225 dated Sep. 23, 2016.
Written Opinion of the International Searching Authority for PCT/EP2016/001225 dated Sep. 23, 2016.
Attili, S. K., "An open pilot study of ambulatory photodynamic therpay using a wearable low-irradiance organic light-emitting diode light source in the treatmen of nonmelanoma skin cancer", British Journal of Dermatology, 2009, vol. 161, pp. 170-173.

* cited by examiner

*Primary Examiner* — Gregory D Clark
(74) *Attorney, Agent, or Firm* — Faegre Drinker Biddle & Reath LLP

(57) ABSTRACT

The present invention relates inter alia to organic compounds, compositions, formulations and electronic devices.

20 Claims, No Drawings

HEXAMETHYLINDANES

CROSS-REFERENCE TO RELATED APPLICATIONS

This application is a national stage application (under 35 U.S.C. § 371) of PCT/EP2016/001225, filed Jul. 14, 2016, which claims benefit of European Application No. 15180942.3, filed Aug. 13, 2015, both of which are incorporated herein by reference in their entirety.

The present invention describes carbazole derivatives, in particular for use as triplet matrix materials in organic electroluminescent devices. The invention furthermore discloses a process for the preparation of the compounds according to the invention and for the preparation of electronic devices comprising these compounds.

The structure of organic electroluminescent devices (OLEDs) in which organic semiconductors are employed as functional materials is described, for example, in U.S. Pat. Nos. 4,539,507, 5,151,629, EP 0676461 and WO 98/27136. The emitting materials employed are frequently organometallic complexes which exhibit phosphorescence instead of fluorescence. For quantum-mechanical reasons, significant increase with respect to energy and power efficiency is possible using organometallic compounds as phosphorescent emitters. In general, there is still a need for improvement in OLEDs, in particular also in OLEDs which exhibit triplet emission (phosphorescence), for example with respect to efficiency, operating voltage and lifetime.

The properties of phosphorescent OLEDs are not determined only by the triplet emitters employed. In particular, the other materials used, such as, for example, matrix materials, are also of particular importance here. Improvements in these materials may thus also result in significant improvements in the OLED properties.

In accordance with the prior art, use is made, inter alia, of indolocarbazole derivatives (for example in accordance with WO 2007/063754 or WO 2008/056746) or indenocarbazole derivatives (for example in accordance with WO 2010/136109 or WO 2011/000455), in particular those which are substituted by electron-deficient heteroaromatic compounds, such as triazine, as matrix materials for phosphorescent emitters. Furthermore, bisdibenzofuran derivatives (for example in accordance with EP 2301926) are used, for example, as matrix materials for phosphorescent emitters. However, there is still a need for improvement on use of these matrix materials, in particular with respect to the efficiency, lifetime and operating voltage of the device.

The object of the present invention is the provision of compounds which are suitable for use in a fluorescent or in particular in a phosphorescent OLED, in particular as matrix material. In particular, the object of the present invention is to provide matrix materials which are also suitable for green- and if desired also for blue-phosphorescent OLEDs and which result in good efficiency, a long lifetime and a low operating voltage. The properties of the matrix materials in particular have a significant influence on the lifetime and efficiency of the organic electroluminescent device.

Surprisingly, it has been found that electroluminescent devices which comprise compounds of the following formula (1) have improvements compared with the prior art, in particular on use as matrix materials for phosphorescent dopants.

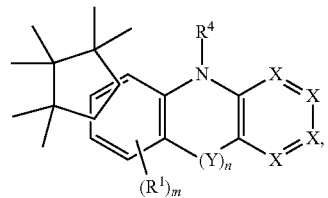

wherein the following applies to the symbols used:

Y is at each occurrence same or different and selected from $C(R^1)_2$, $N(R^1)$, $C(=O)$, $C(=S)$, O, or S, preferably $C(R^1)_2$, $N(R^1)$;

X is at each occurrence same or different, and X includes $CR^1$ or N, wherein it is preferred if any of the X groups is represented by $CR^1$;

$R^1$ is at each occurrence same or different, and $R^1$ includes H, D, F, Cl, Br, I, CHO, $N(Ar^1)_2$, $C(=O)Ar^1$, $P(=O)(Ar^1)_2$, $S(=O)Ar^1$, $S(=O)_2Ar^1$, $CR^2=CR^2Ar^1$, CN, $NO_2$, $Si(R^2)_3$, $B(OR^2)_2$, $B(R^2)_2$, $B(N(R^2)_2)_2$, $OSO_2R^2$, a straight-chain alkyl, alkoxy, or thioalkoxy group having 1 to 40 C atoms or a branched or cyclic alkyl, alkoxy, or thioalkoxy group having 3 to 40 C atoms, each of which may be substituted by one or more $R^2$, wherein one or more non-adjacent methylene groups may be replaced by $R^2C=CR^2$, $C≡C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S, or $C(=O)NR^2$, and wherein one or more hydrogen atoms can include a substitution selected from D, F, Cl, Br, I, CN, $NO_2$, or an aromatic or heteroaromatic ring system having 5 to 60 aromatic ring atoms, which may in each case be substituted by one or more radicals $R^2$, or an aryloxy or heteroaryloxy group having 5 to 40 aromatic ring atoms, which is optionally substituted by one or more radicals $R^2$, or an aralkyl or heteroaralkyl group having 5 to 40 aromatic ring atoms, which is optionally substituted by one or more radicals $R^2$, or a combination of these systems; wherein two or more substituents $R^1$ together with the atoms to which they are bonded, or two substituents $R^1$, together with the atom to which they are bonded, may also form a mono- or polycyclic, aliphatic or aromatic ring system with one another;

$R^2$ is at each occurrence same or different, and $R^2$ includes H, D, F, Cl, Br, I, $N(R^3)_2$, CN, $NO_2$, $Si(R^3)_3$, $B(OR^3)_2$, $C(=O)R^3$, $P(=O)(R^3)_2$, $S(=O)R^3$, $S(=O)_2R^3$, $OSO_2R^3$, a straight-chain alkyl, alkoxy or thioalkoxy group having 1 to 40 C atoms or a straight-chain alkenyl or alkynyl having 2 to 40 C atoms or a branched or cyclic alkyl, alkenyl, alkynyl, alkoxy, alkylalkoxy, or thioalkoxy group having 3 to 40 C atoms, each of which is optionally substituted by one or more radicals $R^3$, where one or more non-adjacent $CH_2$ groups is optionally replaced by $R^3C=CR^3$, $C≡C$, $Si(R^3)_2$, $Ge(R^3)_2$, $Sn(R^3)_2$, $C=O$, $C=S$, $C=Se$, $C=NR^3$, $P(=O)(R^3)$, SO, $SO_2$, $NR^3$, O, S or $CONR^3$ and where one or more H atoms is optionally replaced by D, F, Cl, Br, I, CN or $NO_2$, or an aromatic or heteroaromatic ring system having 5 to 60 aromatic ring atoms, which may in each case be substituted by one or more radicals $R^3$, or an aryloxy, aralkoxy, or heteroaryloxy group having 5 to 60 aromatic ring atoms, which is optionally substituted by one or more radicals $R^3$, or a diarylamino group, a diheteroarylamino group, or arylheteroarylamino group having 10 to 40 aromatic ring atoms, which is optionally substituted by one or more radicals $R^3$, or a combination of two or more of these groups, wherein two or more substituents $R^2$ may also form a mono- or polycyclic, aliphatic or aromatic ring system with one another, wherein preferably two or more geminal and vicinal substituents $R^2$ form a single mono- or polycyclic, aliphatic or aromatic ring system;

$R^3$ is at each occurrence same or different, and $R^3$ includes H, D, F, or an aliphatic, aromatic and/or heteroaromatic hydrocarbon radical having 1 to 20 C atoms, wherein on or more H atoms can be substituted for F, wherein two or more substituents $R^3$ may also form a mono- or polycyclic, aliphatic or aromatic ring system with one another, wherein preferably geminal and vicinal substituents $R^3$ do not form a single mono- or polycyclic, aliphatic or aromatic ring system;

$R^4$ is at each occurrence same or different, and $R^4$ includes $Ar^1$, a first moiety comprising a $C_1$-$C_{40}$ alkyl, a $C_1$-$C_{40}$ unsaturated group, a $C_3$-$C_{40}$ cyclic alkyl, or a $C_3$-$C_{40}$ unsaturated cyclic group, the moiety further comprising $R^2$, wherein one or more methylene groups, preferably non-vicinal methylene groups, can include a substitution selected from $R^2C=CR^2$, $C\equiv C$, $Si(R^2)_2$, $Ge(R^2)_2$, $Sn(R^2)_2$, C=O, C=S, C=Se, $C=NR^2$, $P(=O)(R^2)$, SO, $SO_2$, $NR^2$, O, or $C(=O)NR^2$, wherein one or more hydrogen atoms can include a substitution selected from D, F, Cl, Br, I, CN, $NO_2$, or $Ar^1$;

$Ar^1$ is at each occurrence same or different, and $Ar^1$ includes an aromatic ring, an aromatic ring system, a hetero-aromatic ring, a hetero-aromatic ring system, or a aromatic hetero-aromatic ring system, wherein $Ar^1$ can include one or more $R^3$ substitution;

m is 0, 1 or 2, preferably m is 1, very preferably m is 0;

n is 0 or 1, preferably 0, wherein n=0 means that both rings are bonded to each other via a covalent single bond.

The recitation that two or more substituents may also form a ring is to be understood within the scope of this invention that the two substituents are connected by a single chemical bond, as illustrated by the following scheme:

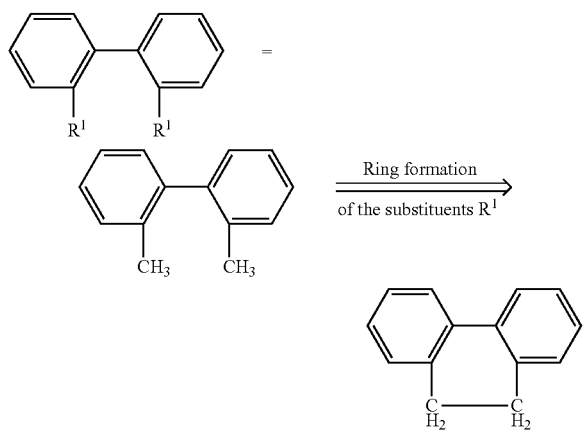

Moreover, the above recitation should also be understood that for the case when one of the two substituents is hydrogen, the second substituents forms the single bond to the atom the hydrogen was bonded to, as illustrated in the following scheme:

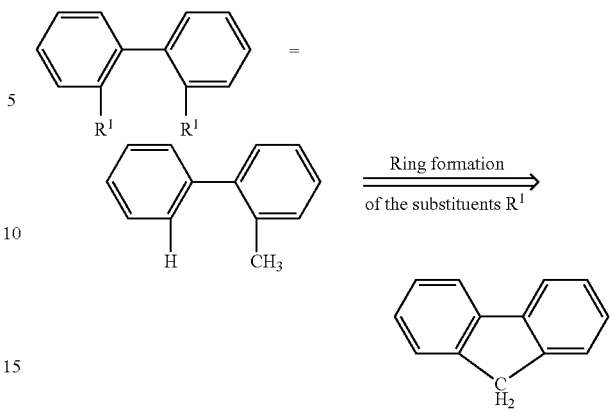

An aryl group in according to this invention contains at least 6 C atoms; a heteroaryl group according to this invention contains at least 2 C atoms and at least one heteroatom, with the proviso that the sum of C atoms and heteroatoms is at least 5. The heteroatoms are preferably selected from N, O, and/or S. An aryl group or heteroaryl group here is taken to mean either a simple aromatic ring, i.e. benzene, or a simple heteroaromatic ring, for example pyridine, pyrimidine, thiophene, etc., or a condensed (fused) aryl or heteroaryl group, for example naphthalene, anthracene, pyrene, quinoline, isoquinoline, etc.

An aromatic ring system in the sense of this invention contains 6 to 60 C atoms in the ring system. A heteroaromatic ring system in the sense of this invention contains 5 to 60 aromatic ring atoms of which at least one is a heteroatom. The heteroatoms are preferably selected from N, O, and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an sp$^3$ hybridized C, Si, N, or O atom, an sp$^2$ hybridized C or N, or an sp hybridized C atom. Thus, for example, systems such as 9,9'-spirobifluorene, 9,9-diarylfluorene, triarylamine, diaryl ether, stilbene, etc., are also intended to be taken to be aromatic ring systems in the sense of this invention, as are systems in which two or more aryl groups are connected, for example, by a cyclic alkyl group, alkenyl, or alkynyl or by a silyl group. Furthermore, ring systems that are linked to one another by a single bond, such as, for example, biphenyl, terphenyl, or diphenyltriazine are referred to as an aromatic and heteroaromatic ring system in the sense of this application.

An aromatic or heteroaromatic ring system having 5-60 aromatic ring atoms, which may also in each case be substituted by the above-mentioned substituents and which may be linked via any desired positions on the aromatic or heteroaromatic group, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, bi-phenylene, terphenyl, terphenylene, triphenylene, quarterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzo-xazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole or groups derived from combination of these systems.

For the purposes of the present invention, a straight chain aliphatic alkyl group with 1 to 40 C atoms, a branched or cyclic aliphatic alkyl group with 3 to 40 C atoms, an alkenyl group or alkynyl group with 2 to 40 C atoms and in which, in addition, individual H atoms or $CH_2$ groups may be substituted by the above-mentioned substituents, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neo-pentyl, n-hexyl, cyclohexyl, neo-hexyl, n-heptyl, cycloheptyl, n-octyl, cyclooctyl, 2-ethylhexyl, trifluoro-methyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy or 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenyl-thio, ethynylthio, propynylthio, butynylthio, pentynylthio, hexynylthio, heptynylthio or octynylthio.

An electron-deficient heteroaryl group in the sense of the present invention is defined as a 5-membered ring heteroaryl group having at least two heteroatoms, for example imidazole, oxazole, oxadiazole, etc., or as a 6-membered ring heteroaryl group having at least one heteroatom, for example, pyridine, pyrimidine, pyrazine, triazine, etc. Further 6-membered ring aryl or 6-membered ring heteroaryl groups may also be condensed onto these groups, such as, for example, in benzimidazole or quinoline.

In one embodiment, the above-mentioned compound is selected from one of the following formulae (1a), (1b), or (1c):

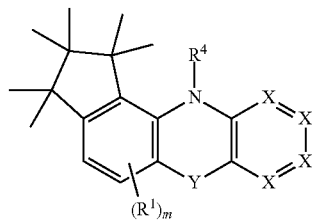

1a

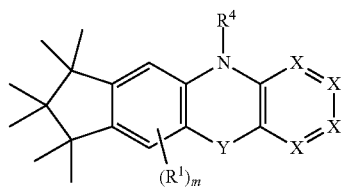

1b

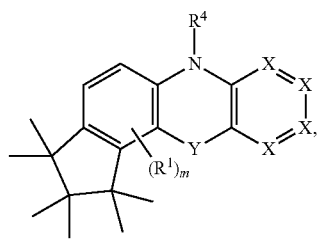

1c wherein symbols $R^1$, $R^4$, X, and Y include the groups as described above and m is 0, 1 or 2, preferably m is 0 or 1, very preferably m is 0.

In another preferred embodiment, the above-mentioned compound of formula (1) is selected from one of the following formulae (2a), (2b), or (2c):

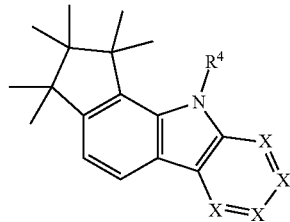

2a

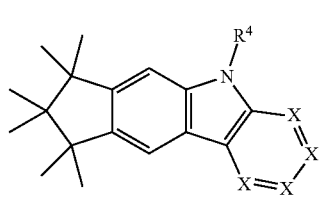

2b

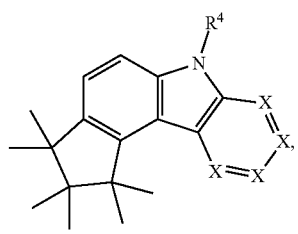

2c wherein symbols $R^4$ and X include the groups as described above.

In a further preferred embodiment, the above-mentioned compound of the formula (1) is selected from one of the following formulae (3a), (3b) and (3c), whereby compounds of the formulae (3a) and (3b) are particularly preferred. Particular preference is given to the compounds of formulae (3a), (3b) and (3c), preferably to compounds of formulae (3a) and (3b), wherein R¹ is equal to H.

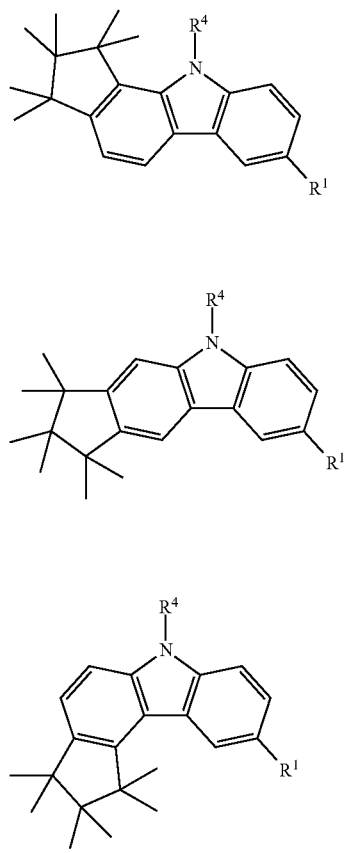

3a

3b

3c

Preference is given to a compound according to the following formula (4)

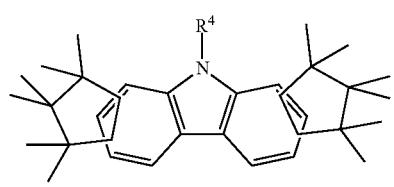

4

In a particular preferred embodiment, the above-mentioned compound of the formula (1) is selected from one of the following formulae (4a), (4b) and (4c), whereby compounds of the formulae (4a) and (4b) are particularly preferred.

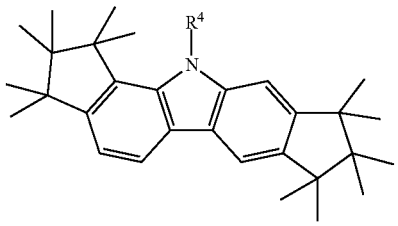

4a

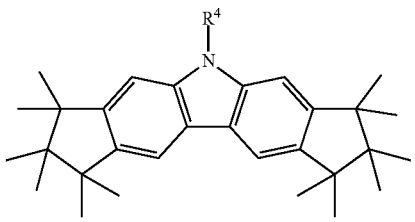

4b

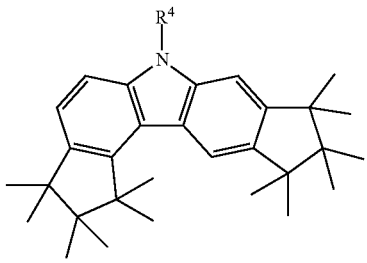

4c

In a yet another preferred embodiment, the above-mentioned compound of the formula (1) is selected from one of the following formula (5).

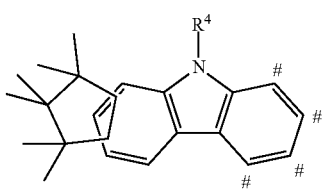

5 wherein two vicinal aromatic carbon atoms that are marked with # are bonded to the carbon atom and nitrogen atom of the following group (5-1) that are marked with *. Through connection of group (5-1) to formula (5), an additional five-membered ring is built.

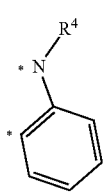

5-1

Particular preference is given to one of the following formulae (5a) to (5r).
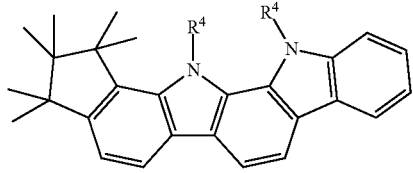
5a
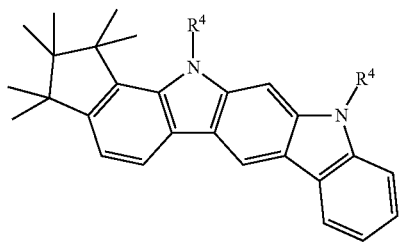
5b
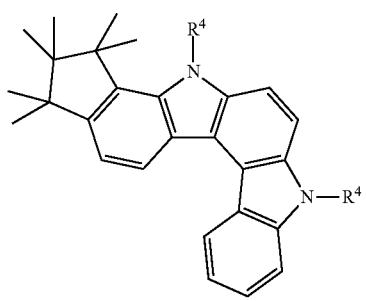
5c
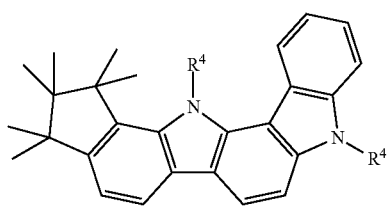
5d
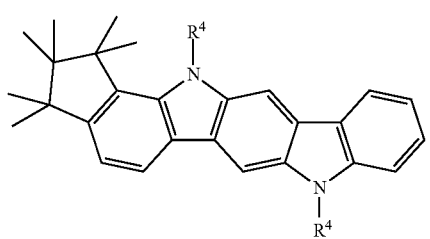
5e
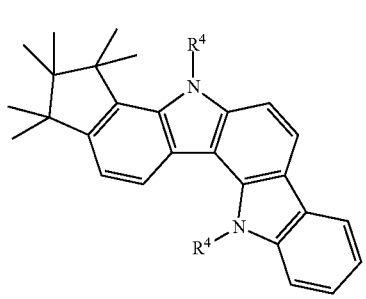
5f
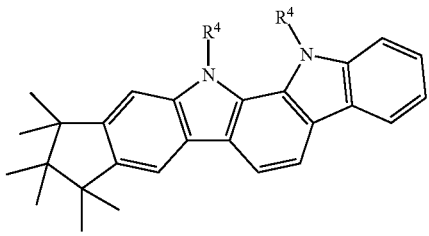
5g
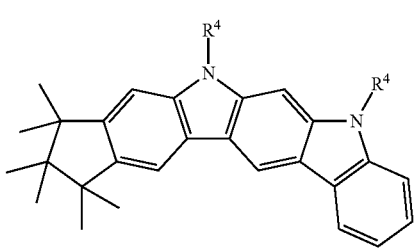
5h
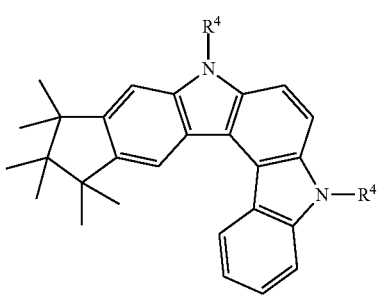
5i
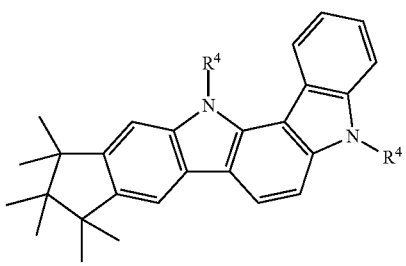
5j
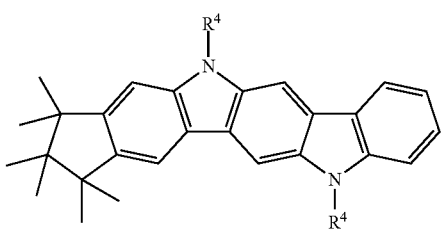
5k
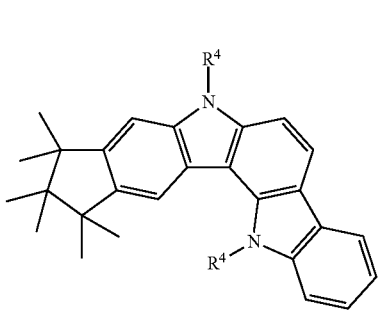
5l 5m 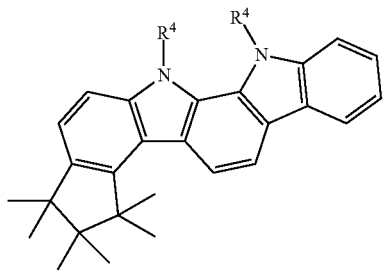
5n 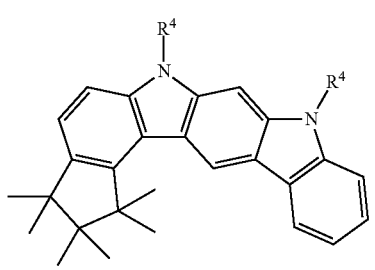
5o 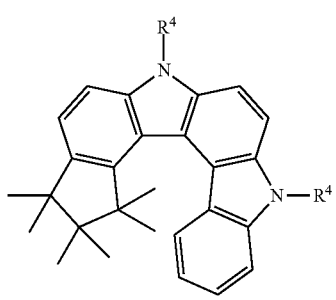
5p 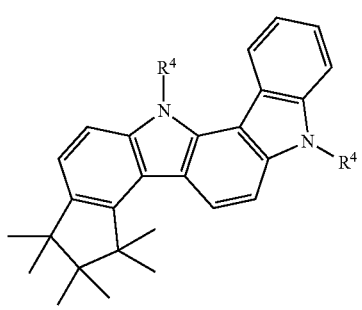
5q 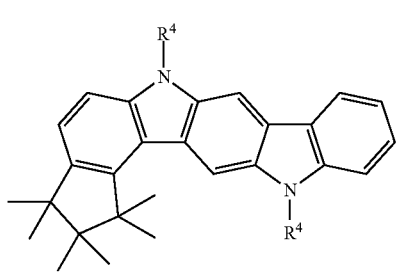
5r 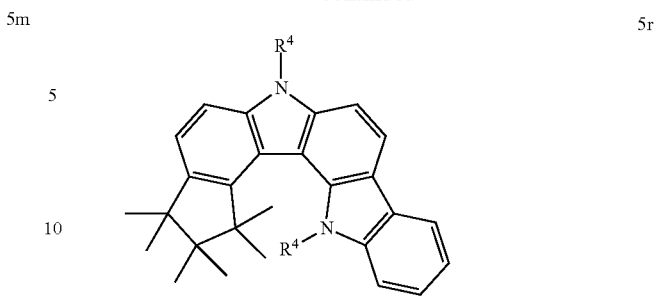
whereas compounds of formulae (5g), (5h), (5j) and (5k) are particularly preferred, compounds of formulae (5g), (5h) and (5k) are very particularly preferred and compounds of formulae (5h) and (5k) are even more preferred.
In yet another preferred embodiment, the above-mentioned compound of the formula (1) is selected from one of the following formulae (6a) to (6d).
6a 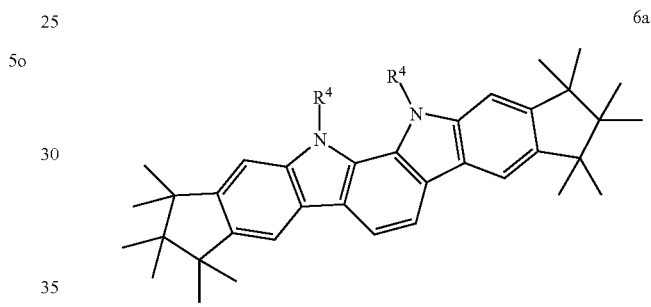
6b 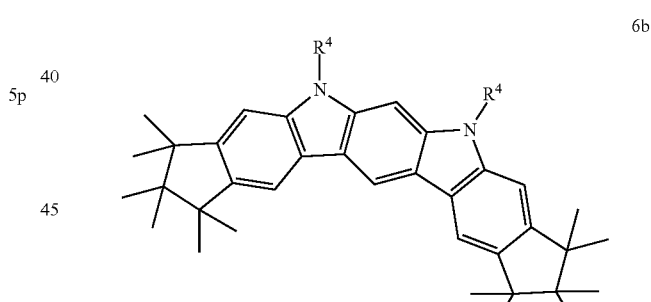
6c 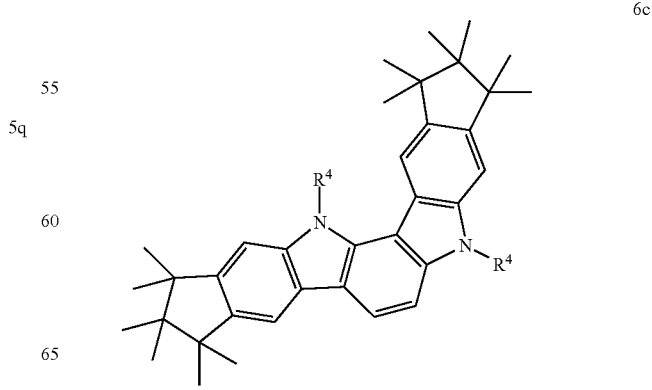

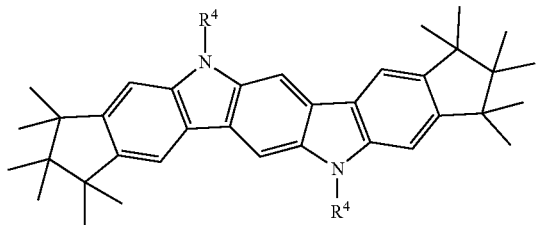
6d whereas compounds of formulae (6a), (6b) and (6d) are particularly preferred.

In yet another preferred embodiment, the above-mentioned compound of the formula (1) is selected from one of the following formula (7).

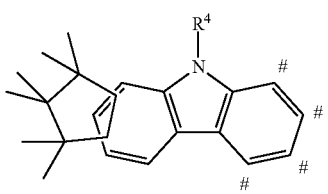
7 wherein two vicinal aromatic carbon atoms that are marked with # are bonded to the carbon atoms of the following group (7-1) that are marked with *. Through connection of group (7-1) to formula (7), an additional five-membered ring is built.

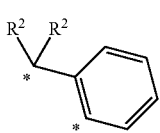
7-1

Particular preference is given to one of the following formulae (7a) to (7r).

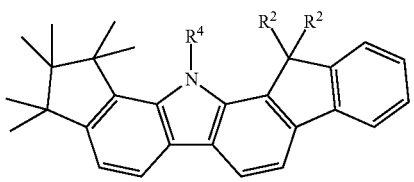
7a

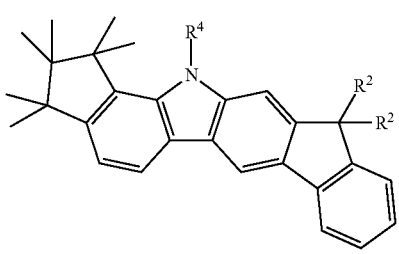
7b

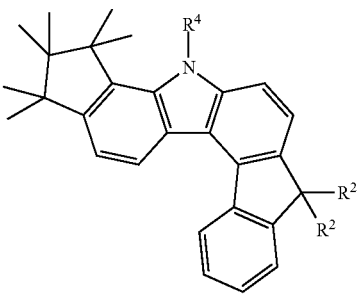
7c

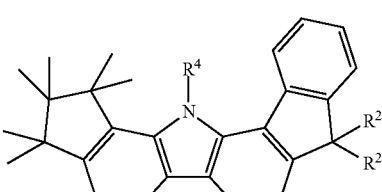
7d

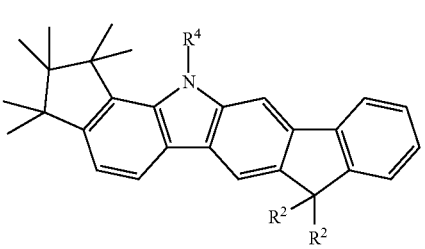
7e

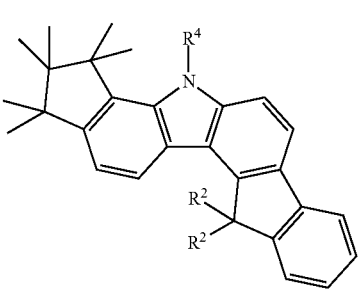
7f

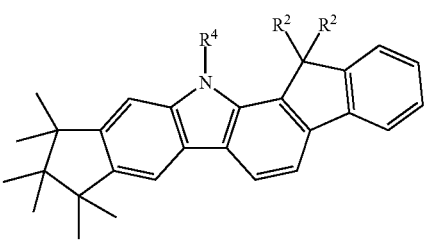
7g

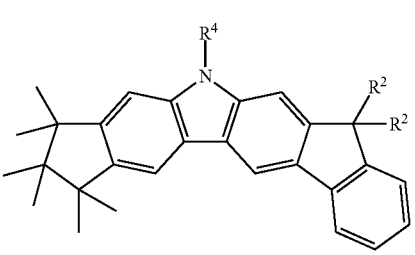
7h

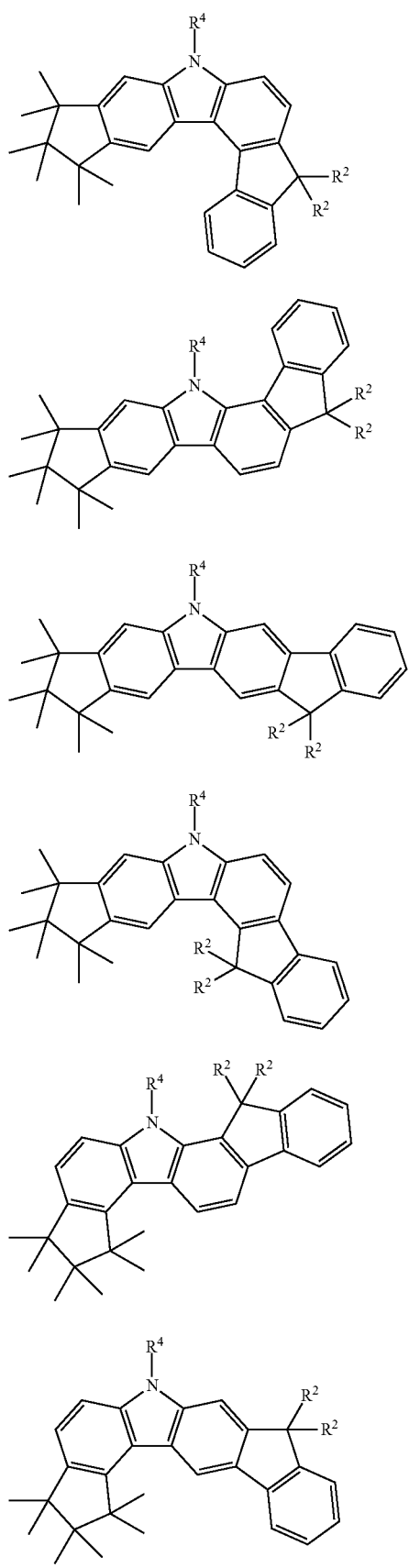
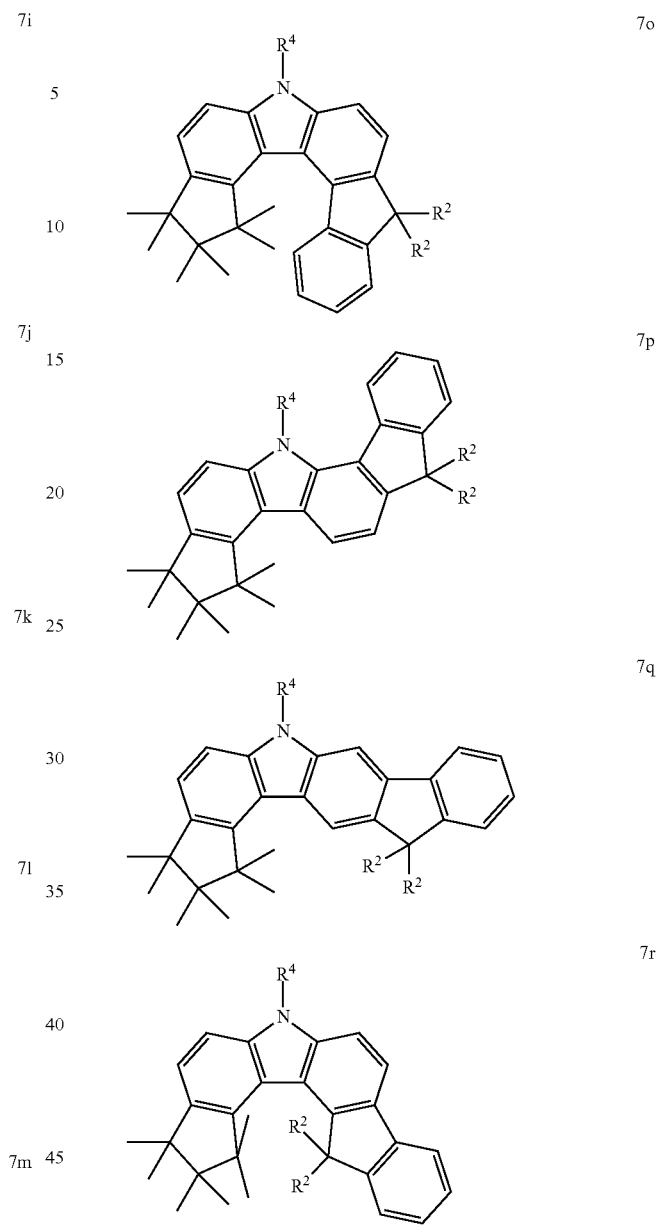
whereas compounds of formulae (7a), (7b), (7d), (7e), (7g), (7h), (7l), (7k), (7m); (7n), (7p) and (7q) are particularly preferred.
In still another preferred embodiment, the above-mentioned compound of the formula (1) is selected from one of the following formulae (8a) to (8l).
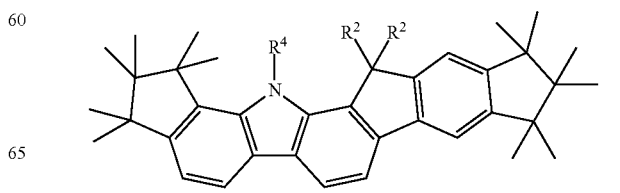

-continued
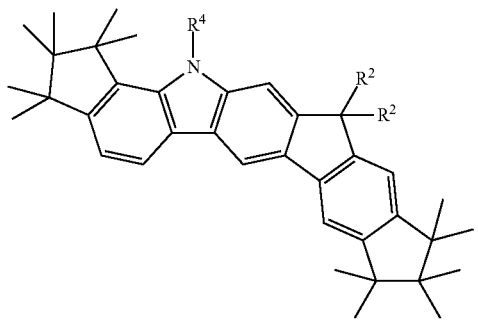
8b
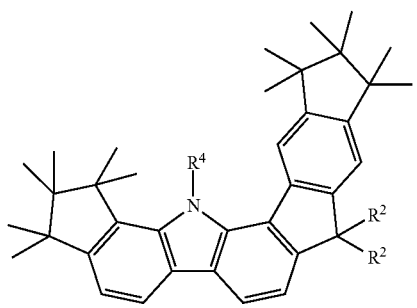
8c
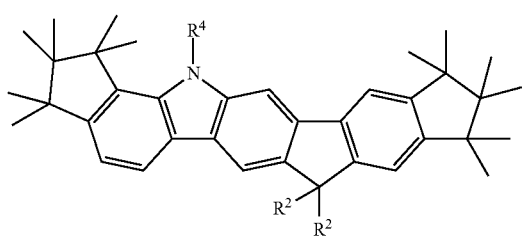
8d
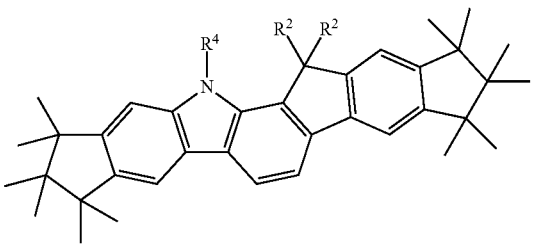
8e
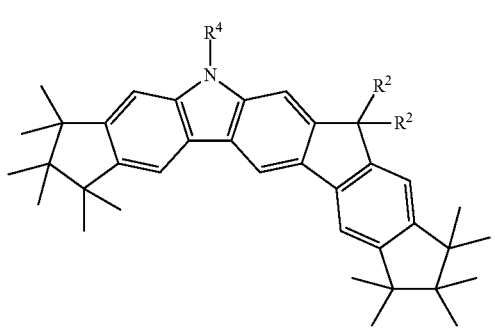
8f
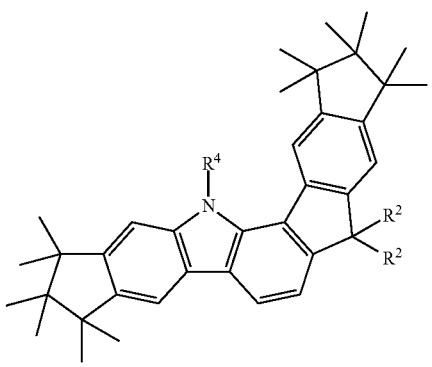
8g
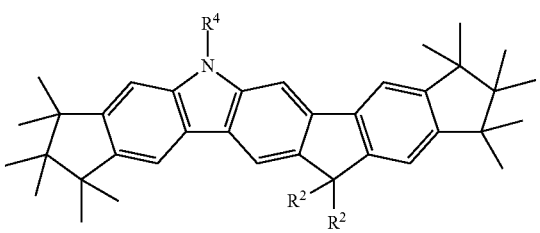
8h
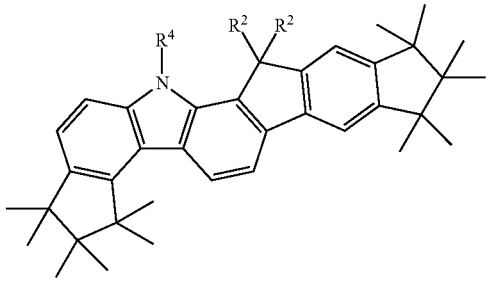
8i
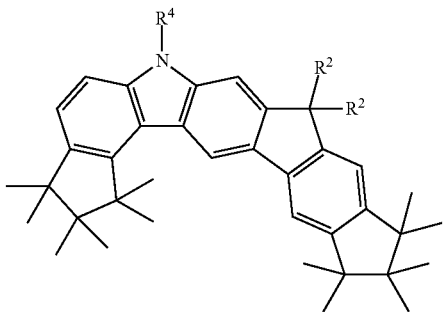
8j
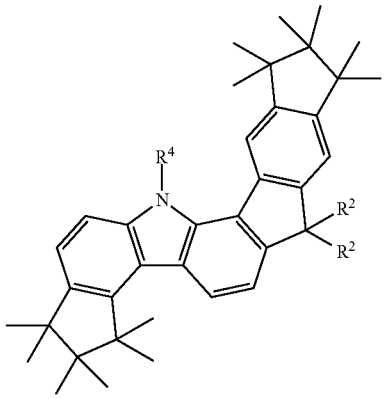
8k

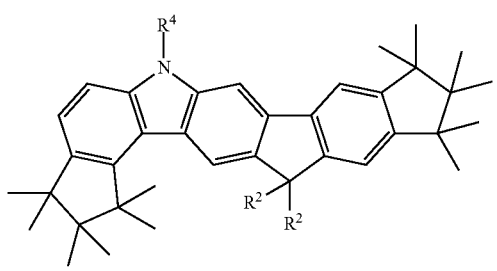
81
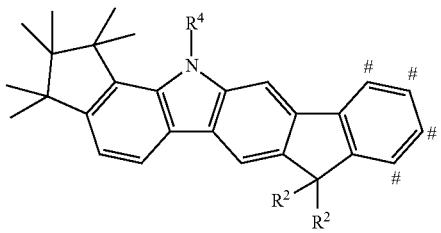
9e
In still another preferred embodiment, the above-mentioned compound of the formula (1) is selected from one of the following formulae (9a) to (9r).
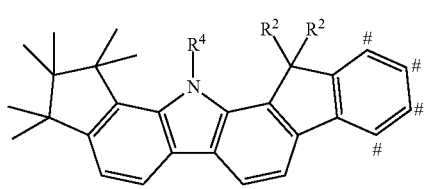
9a
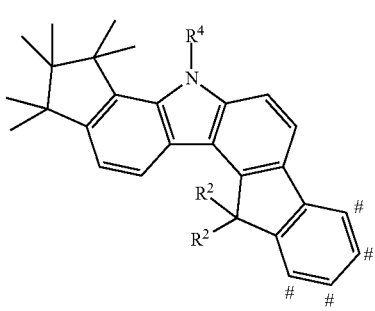
9f
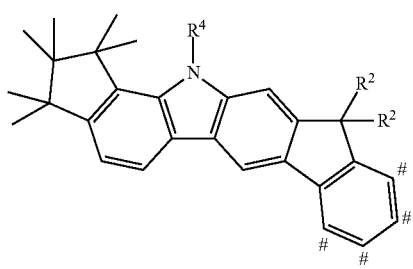
9b
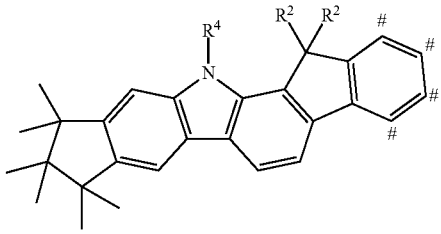
9g
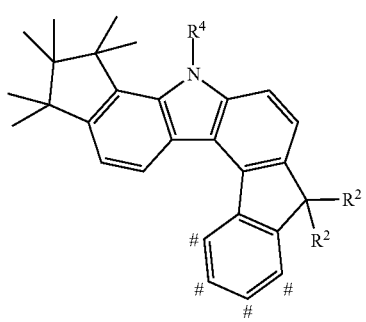
9c
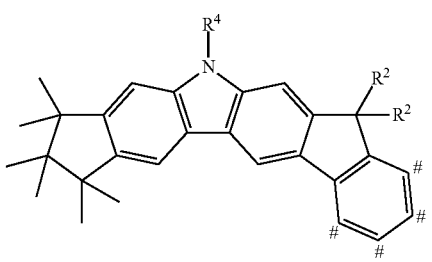
9h
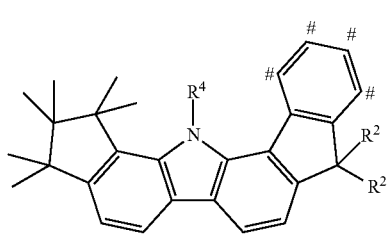
9d
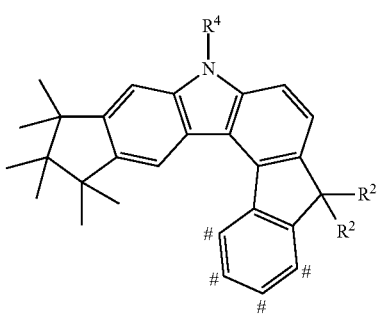
9i 9j
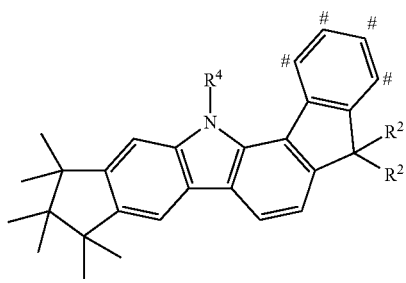
9k
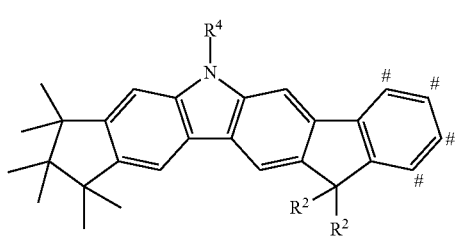
9l
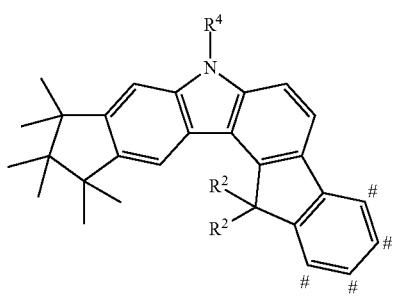
9m
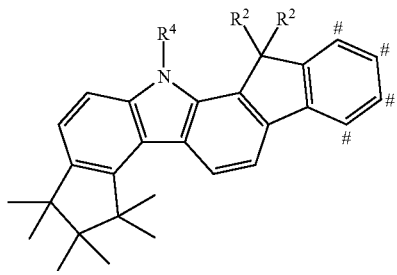
9n
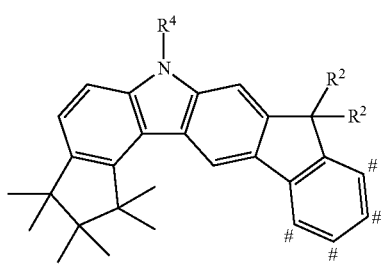
9o
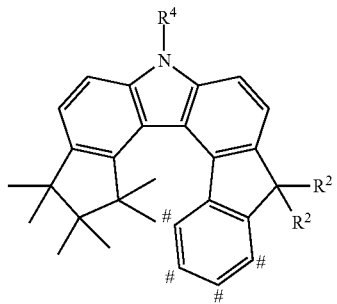
9p
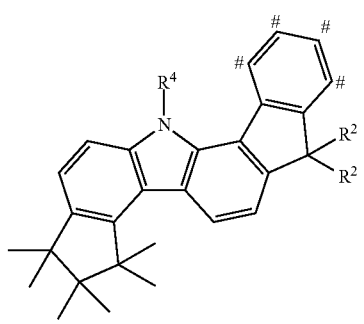
9q
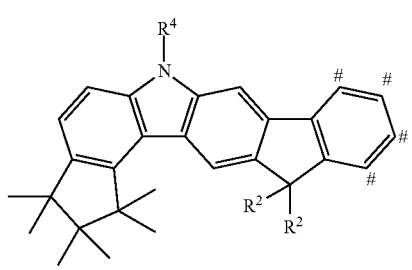
9r
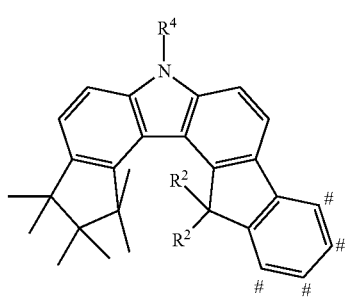
wherein two vicinal aromatic carbon atoms that are marked with # are bonded to the carbon atoms of the group (9-1) or to the carbon and nitrogen atom of group (5-1) that are marked with *.
9-1
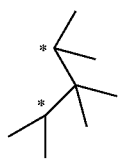
As an example, there are 6 possibilities to connect formula (9a) and formula (9-1). One of these 6 possibilities is shown in the following formula.

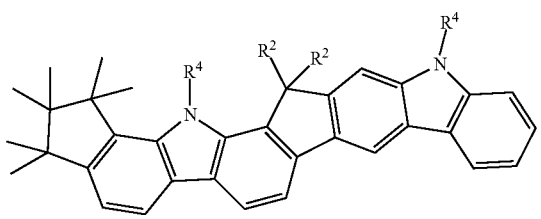

In a yet another preferred embodiment, the above-mentioned compound of the formula (1) is selected from one of the following formula (10).

10

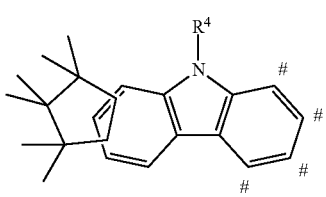

wherein two vicinal aromatic carbon atoms that are marked with # are bonded to the carbon atom and oxygen atom of the following group (10-1) that are marked with *. Through connection of group (10-1) to formula (10), an additional five-membered ring is built.

10-1

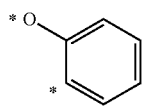

In still another preferred embodiment, the above-mentioned compound of the formula (1) is selected from one of the following formulae (10a) to (10l).

10a

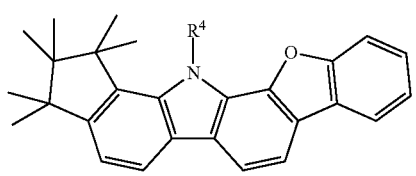

10b

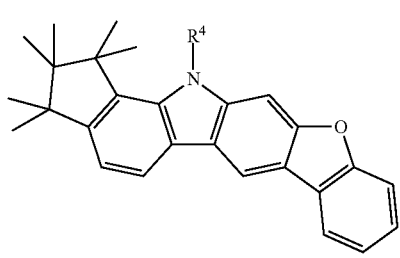

10c

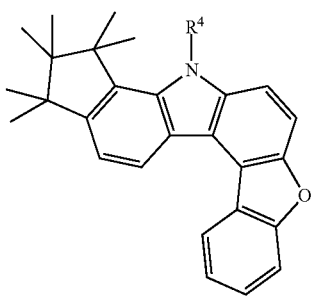

10d

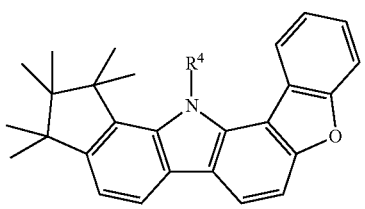

10e

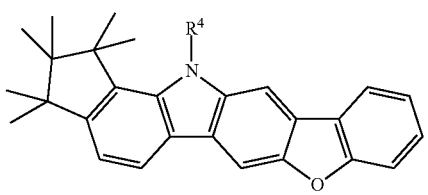

10f

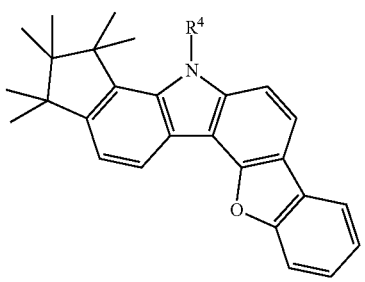

10g

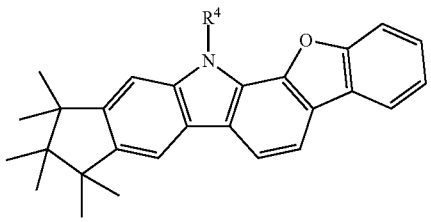

10h

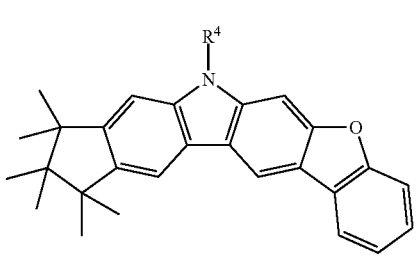

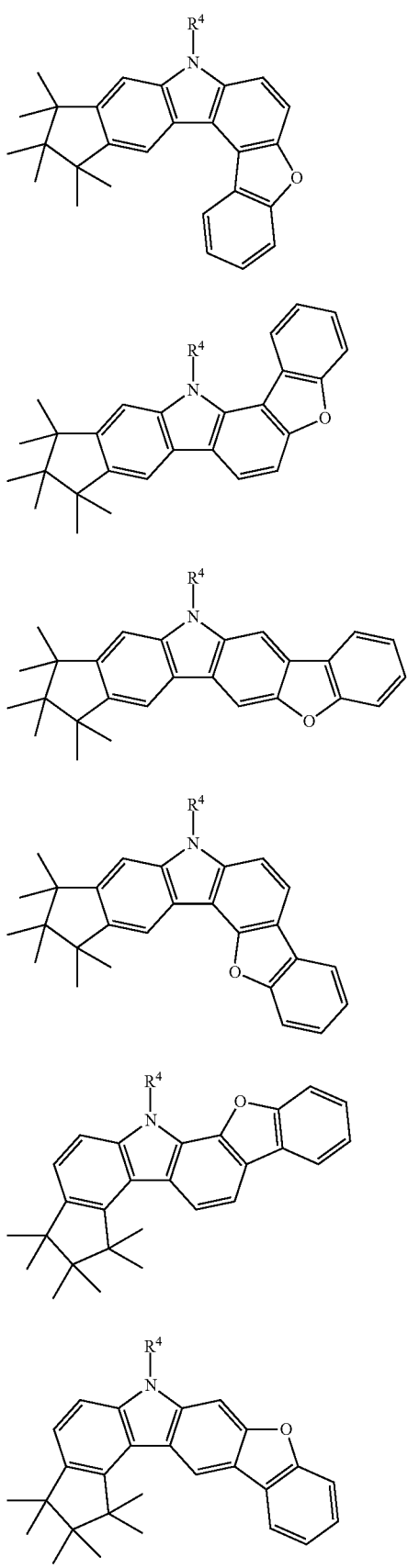

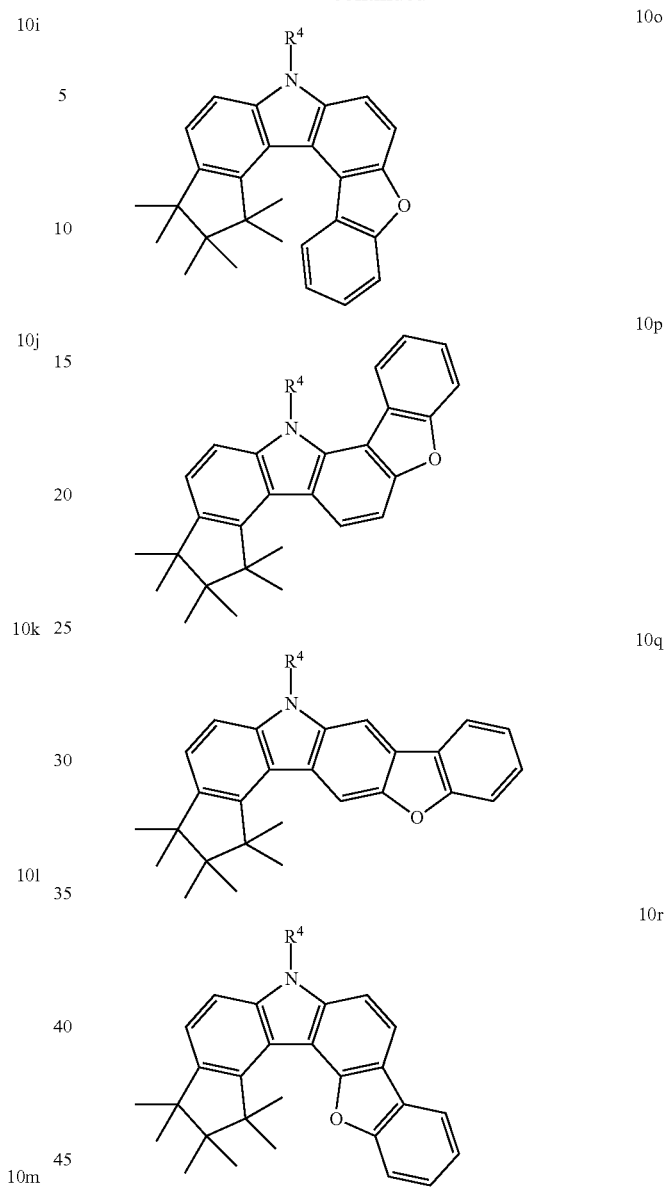

In a yet another preferred embodiment, the above-mentioned compound of the formula (1) is selected from one of the following formula (11).

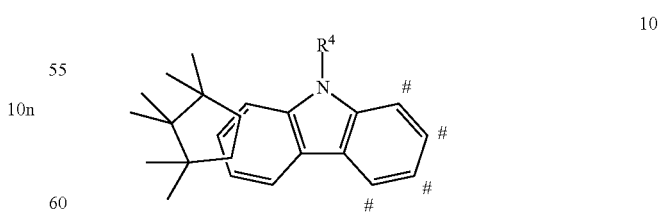

wherein two vicinal aromatic carbon atoms that are marked with # are bonded to the carbon atom and oxygen atom of the following group (11-1) that are marked with *. Through connection of group (11-1) to formula (11), an additional six-membered ring is built.

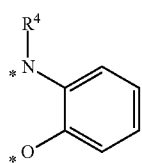
11-1
In still another preferred embodiment, the above-mentioned compound of the formula (1) is selected from one of the following formulae (11a) to (11r).
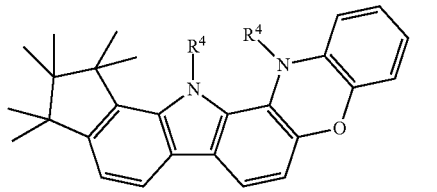
11a
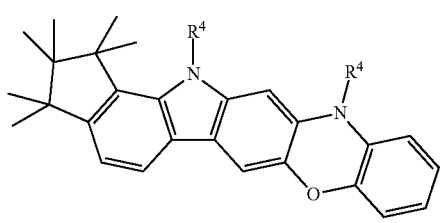
11b
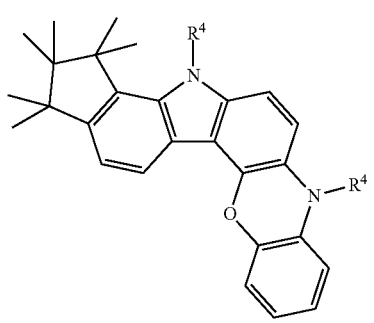
11c
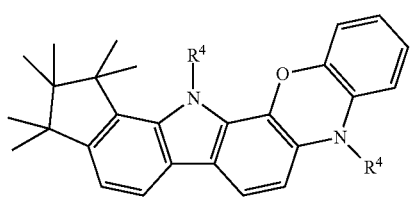
11d
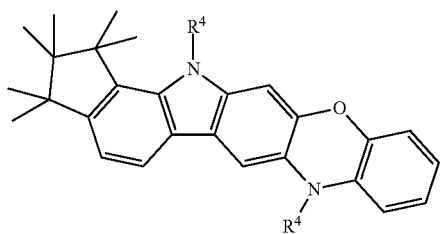
11e
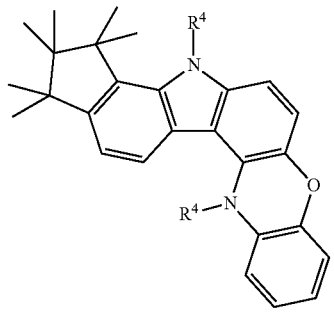
11f
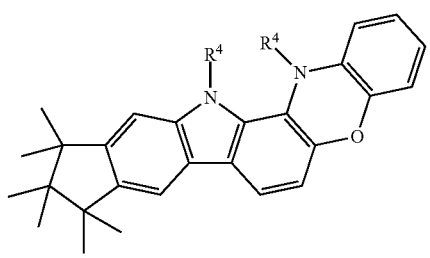
11g
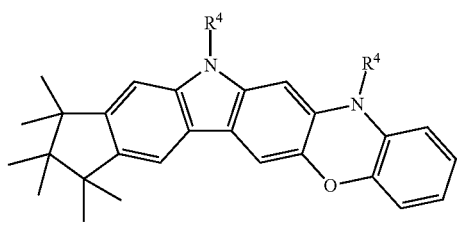
11h
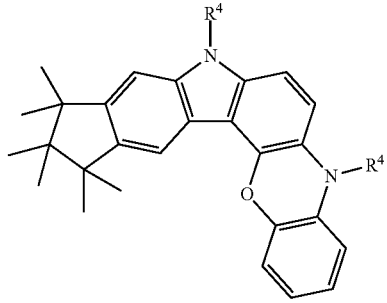
11i
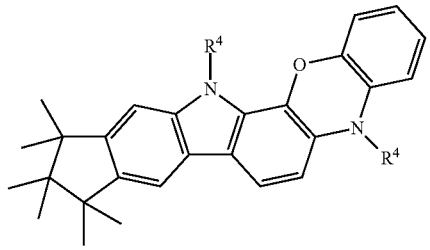
11j
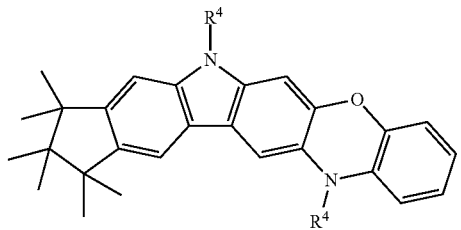
11k

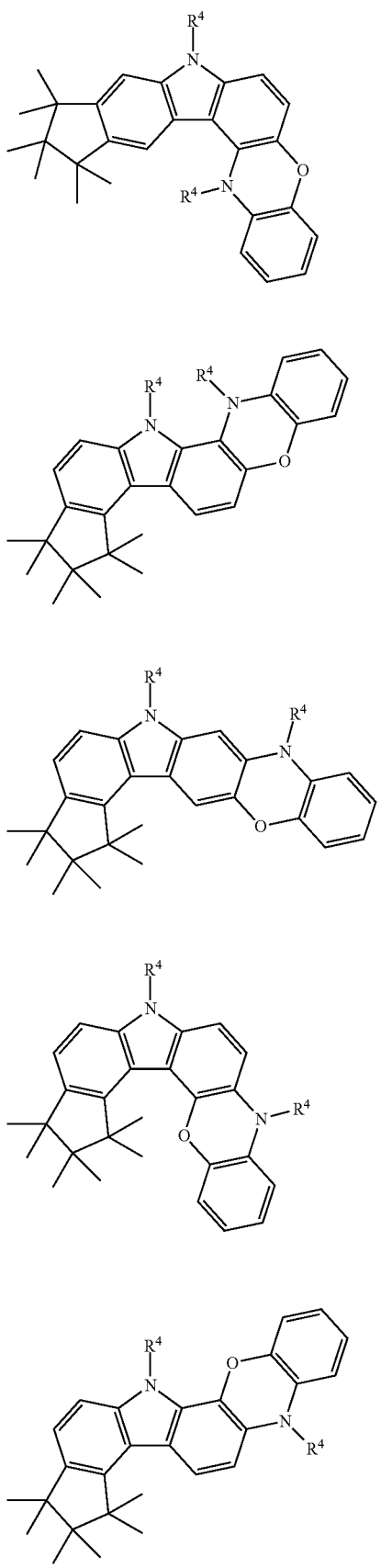

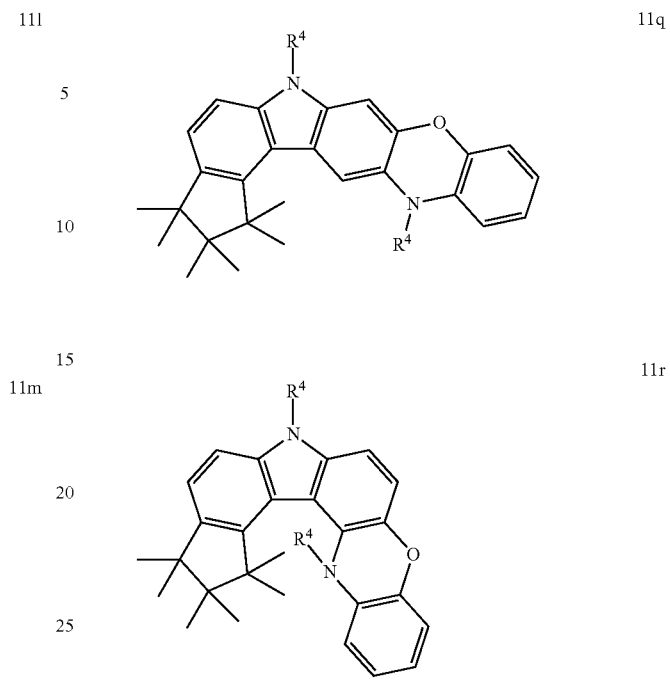

In one embodiment of the invention, the radical $R^4$ which is bonded to the nitrogen atom stands for an aromatic or heteroaromatic ring system having 5 to 60 aromatic ring atoms, preferably having 6 to 24 aromatic ring atoms, which may also be substituted by one or more.

In one further embodiment $R^4$ is selected from a phenyl-, biphenyl-, terphenyl-, quarterphenyl-, pyridyl-, pyrimidinyl-, pyrazinyl-, pyridazinyl-, triazinyl-, diarylaminopenyl-, diarylaminobiphenyl-, fluorenyl-, spiro-bifluorenyl-, carbazoyl-, indenocarbazoyl-, indolocarbazoyl-, dibenzo-thiophenyl- or dibenzofuranylgroup which can be substituted with one or more $R^2$ that can be same or different in each occurrence.

In yet another preferred embodiment $R^4$ is selected from a phenyl-, biphenyl-, terphenyl-, quarterphenyl-, pyridyl-, pyrimidinyl-, pyrazinyl-, pyridazinyl-, triazinyl-, diarylaminopenyl- or diarylaminobiphenyl group which can be substituted with one or more $R^2$ that can be same or different in each occurrence.

In yet one further embodiment, $R^4$ includes one of the following groups:

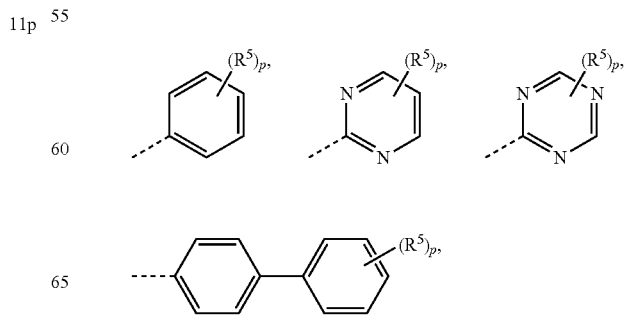

-continued

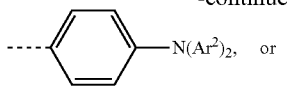
or

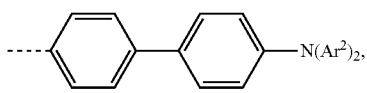

wherein

R⁵ is at each occurrence same or different, and $R^5$ includes H, D, F, Cl, Br, I, CHO, $N(Ar^2)_2$, $C(=O)Ar^2$, $P(=O)(Ar^2)_2$, $S(=O)Ar^2$, $S(=O)_2Ar^2$, $CR^6=CR^6Ar^2$, CN, $NO_2$, $Si(R^6)_3$, $B(OR^6)_2$, $B(R^6)_2$, $B(N(R^6)_2)_2$, $OSO_2R^6$, a straight-chain alkyl, alkoxy, or thioalkoxy group having 1 to 40 C atoms or a branched or cyclic alkyl, alkoxy, or thioalkoxy group having 3 to 40 C atoms, each of which may be substituted by one or more $R^6$, wherein one or more non-adjacent methylene groups may be replaced by $R^6C=CR^6$, C≡C, $Si(R^6)_2$, $Ge(R^6)_2$, $Sn(R^6)_2$, C=O, C=S, C=Se, $C=NR^6$, $P(=O)(R^6)$, SO, $SO_2$, $NR^6$, O, S, or $C(=O)NR^6$, and wherein one or more hydrogen atoms can include a substitution selected from D, F, Cl, Br, I, CN, $NO_2$, or an aromatic or hetero-aromatic ring system having 5 to 60 aromatic ring atoms, which may in each case be substituted by one or more radicals $R^6$, or an aryloxy or heteroaryloxy group having 5 to 40 aromatic ring atoms, which is optionally substituted by one or more radicals $R^6$, or an aralkyl or heteroaralkyl group having 5 to 40 aromatic ring atoms, which is optionally substituted by one or more radicals $R^6$, or a combination of these systems; wherein two or more substituents $R^5$ together with the atoms to which they are bonded, or two substituents $R^5$, together with the atom to which they are bonded, may also form a mono- or polycyclic, aliphatic or aromatic ring system with one another;

$R^6$ is at each occurrence same or different, and $R^6$ includes H, D, F, or an aliphatic, aromatic and/or heteroaromatic hydrocarbon radical having 1 to 20 C atoms, wherein on or more H atoms can be substituted for F, wherein two or more substituents $R^6$ may also form a mono- or polycyclic, aliphatic or aromatic ring system with one another, wherein preferably geminal and vicinal substituents $R^6$ do not form a single mono- or polycyclic, aliphatic or aromatic ring system;

$Ar^2$ is at each occurrence same or different, and $Ar^2$ includes an aromatic ring, an aromatic ring system, a hetero-aromatic ring, a hetero-aromatic ring system, or an aromatic hetero-aromatic ring system, wherein $Ar^2$ can include 5 to 40 ring atoms, wherein $Ar^2$ includes one or more $R^6$ substitution;

p is 0, 1, 2, 3, 4 or 5.

Particular preference is given to the above mentioned compounds wherein $R^4$ is a phenyl group which can be unsubstituted or substituted by one or more $R^5$ as outlined above.

Examples of compounds according to the invention are the following structures.

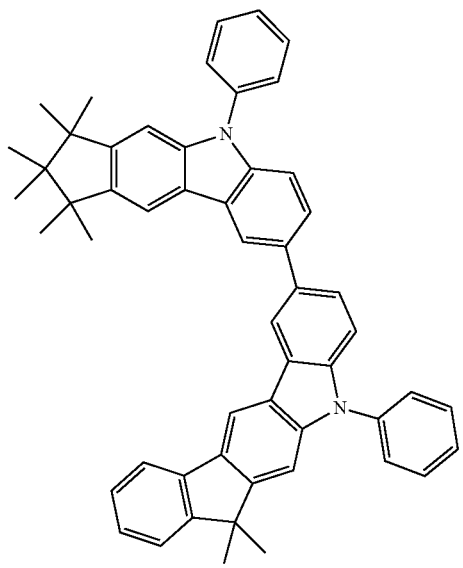

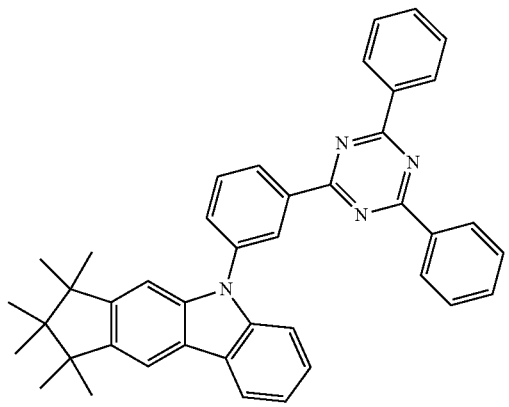

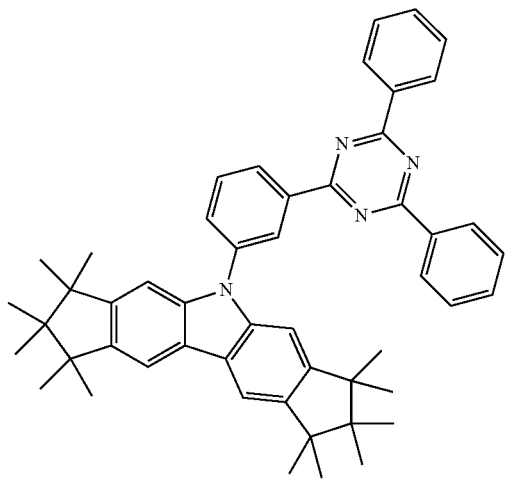

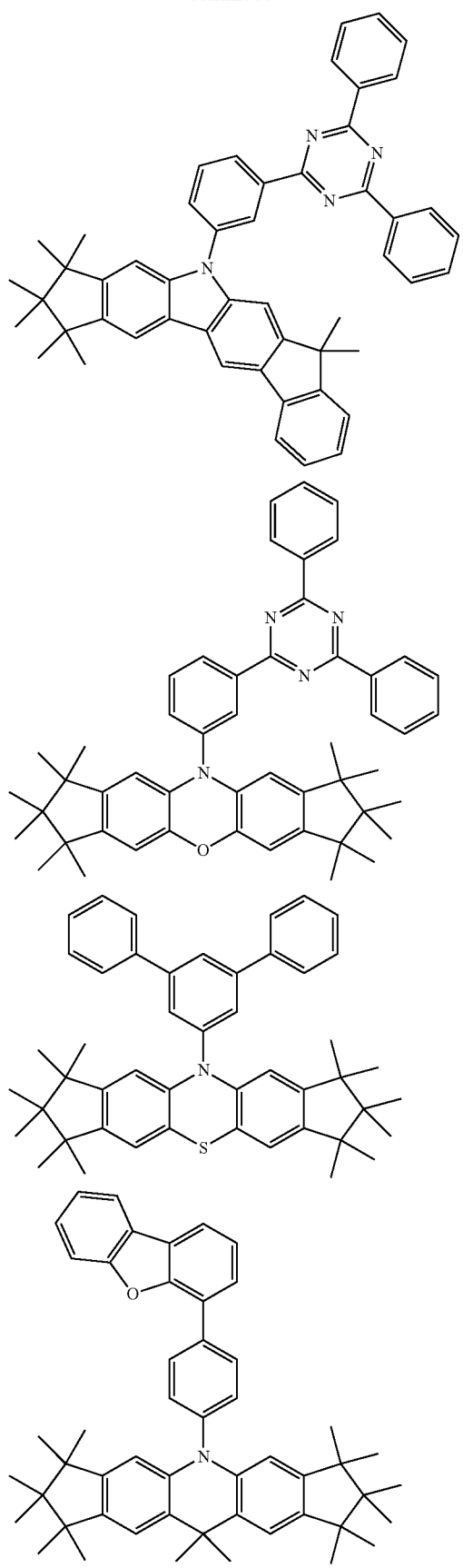
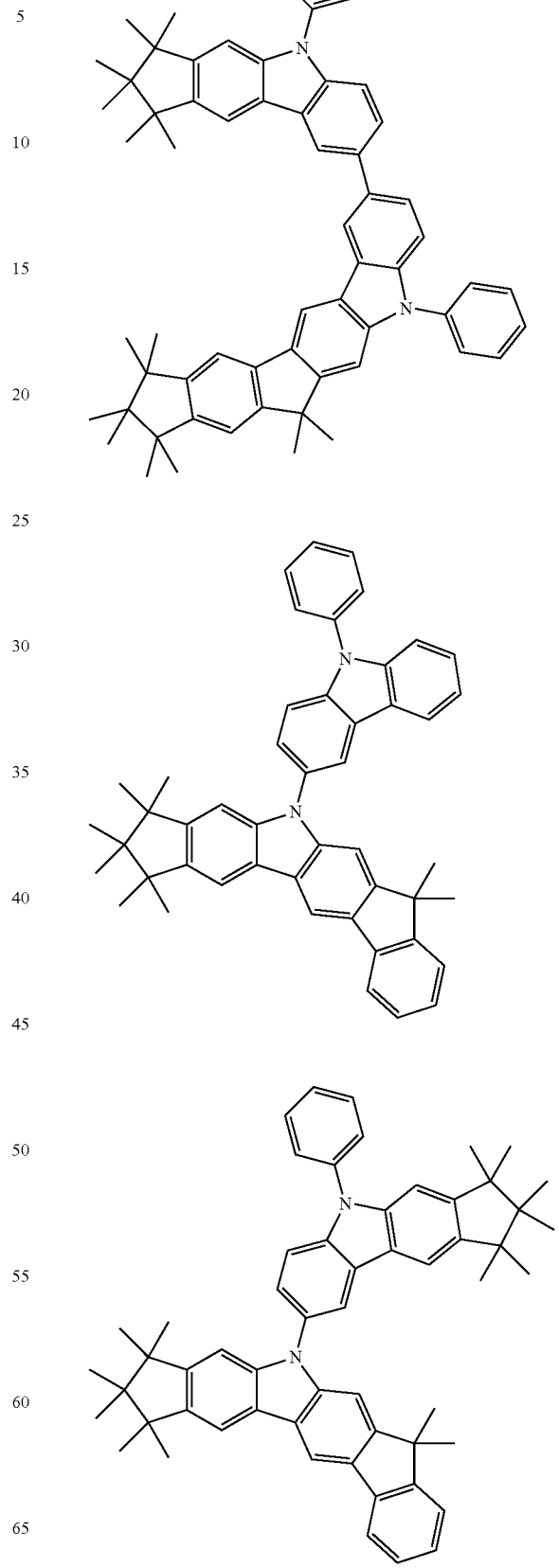

35
-continued
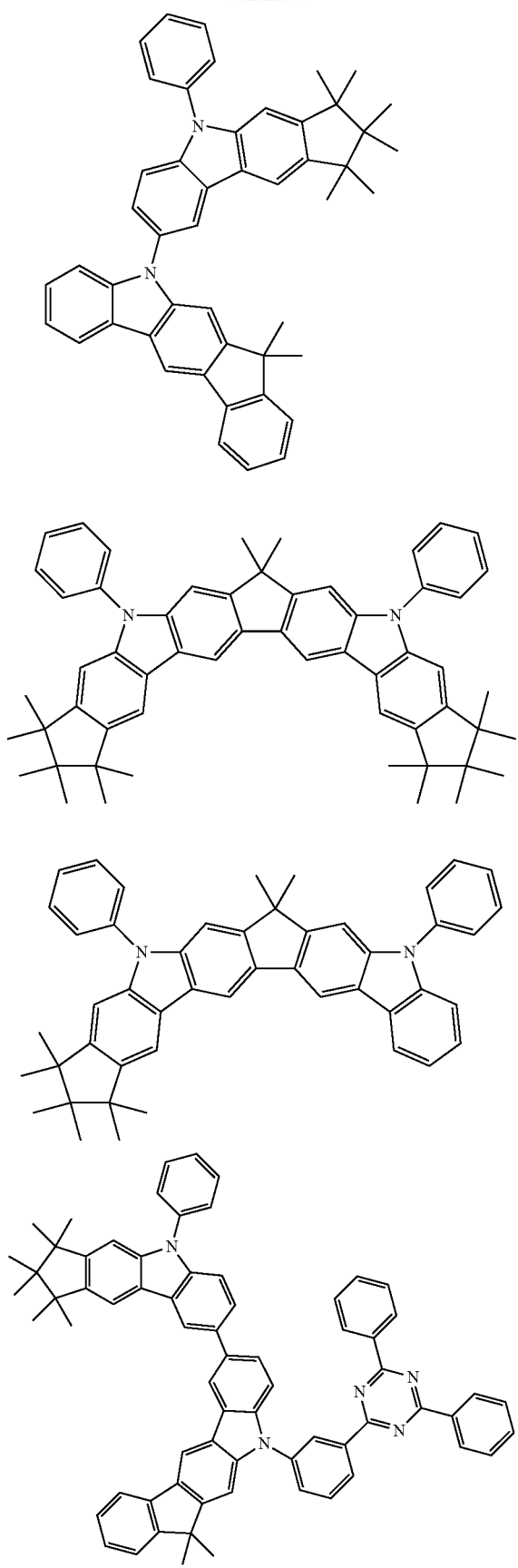
36
-continued
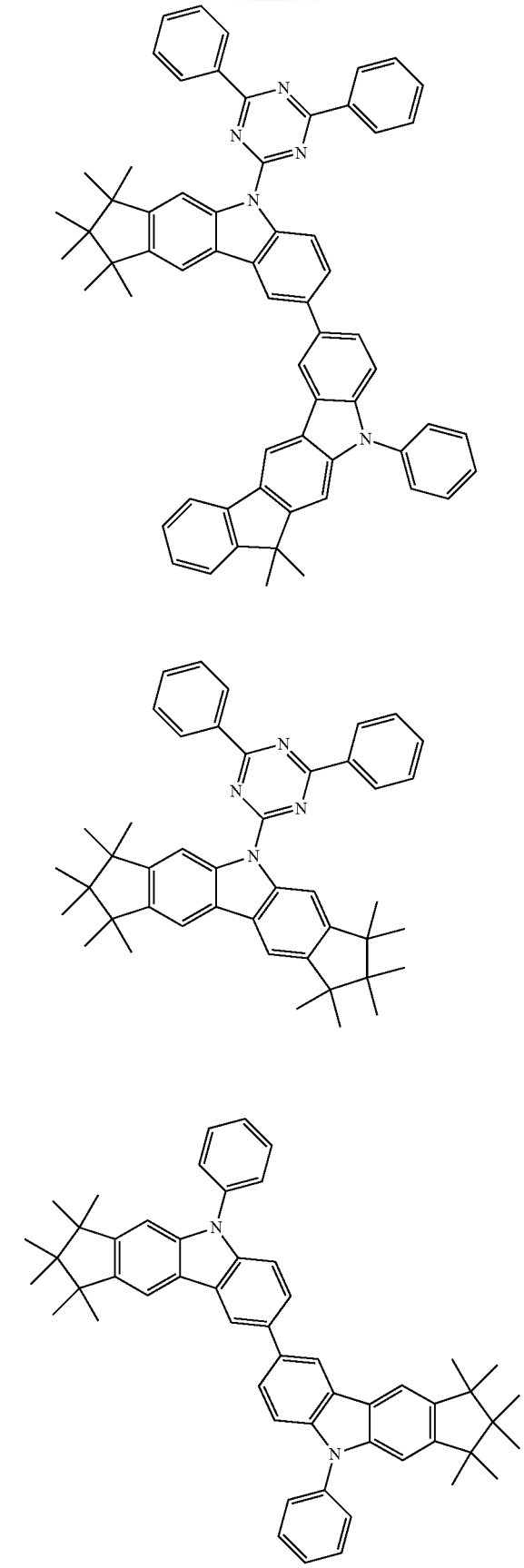

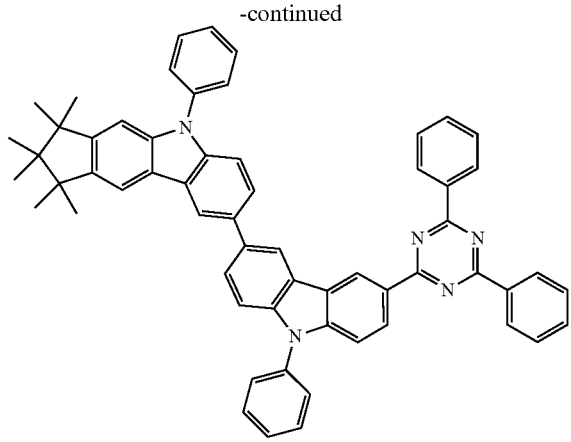
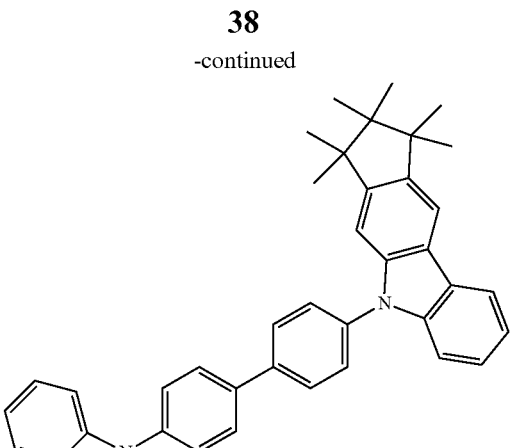
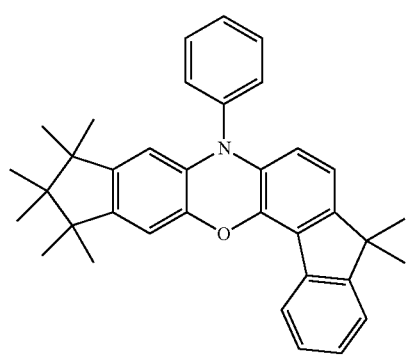
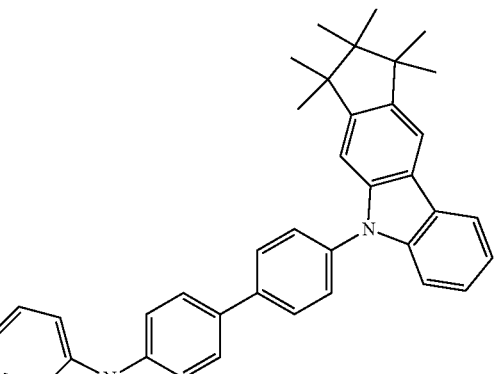
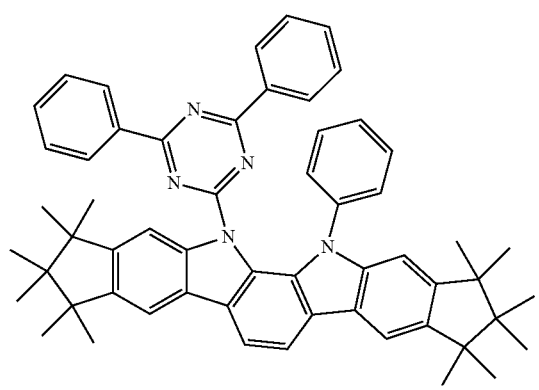
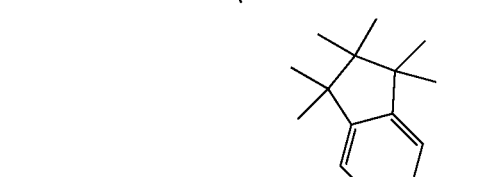
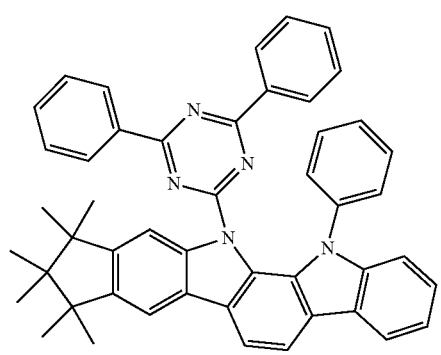

-continued
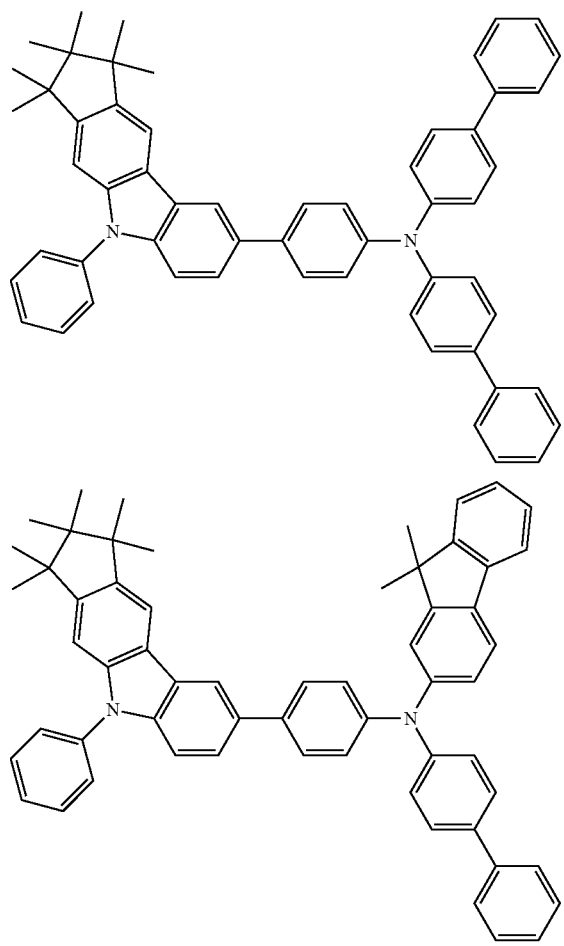
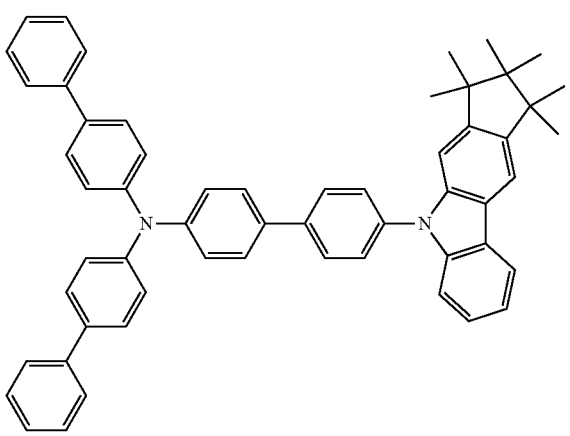
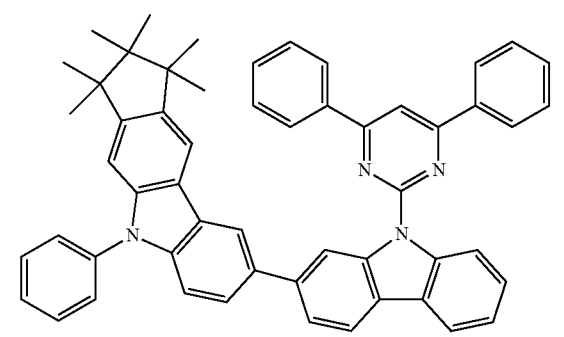
-continued
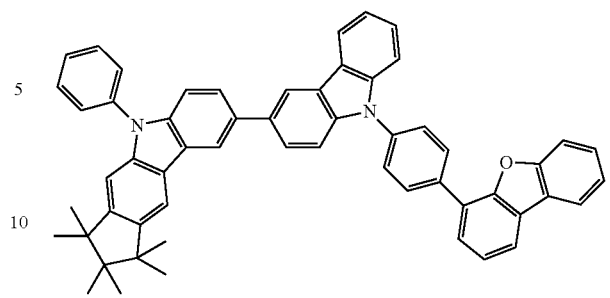
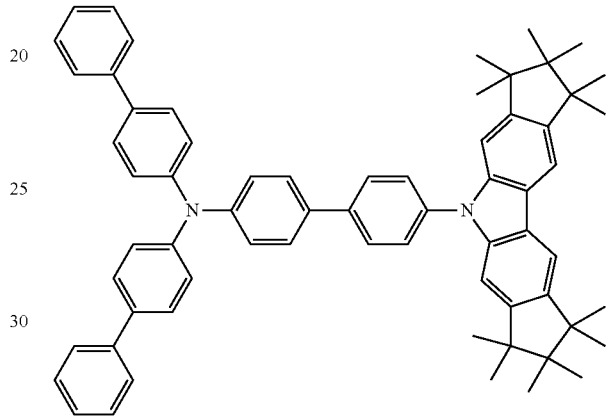
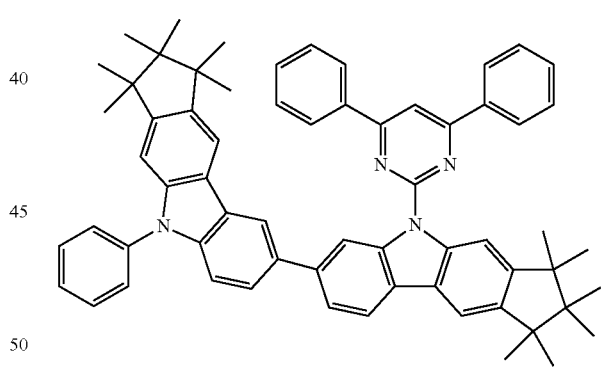
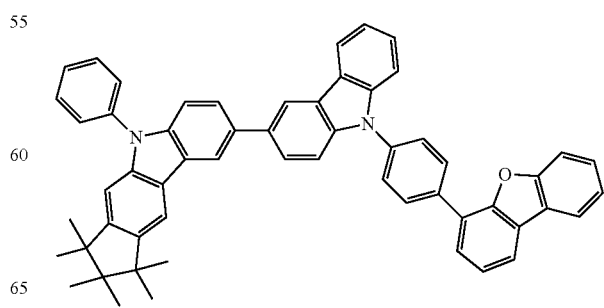

41
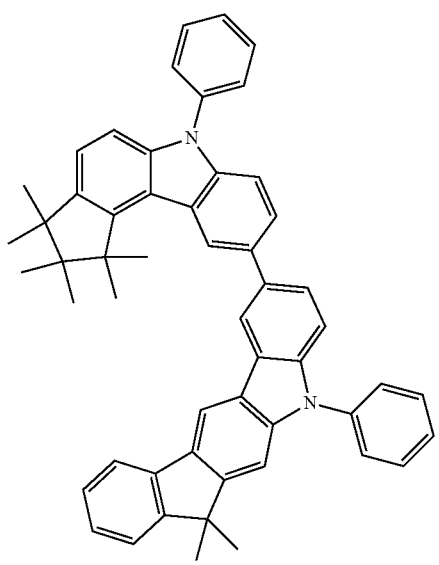
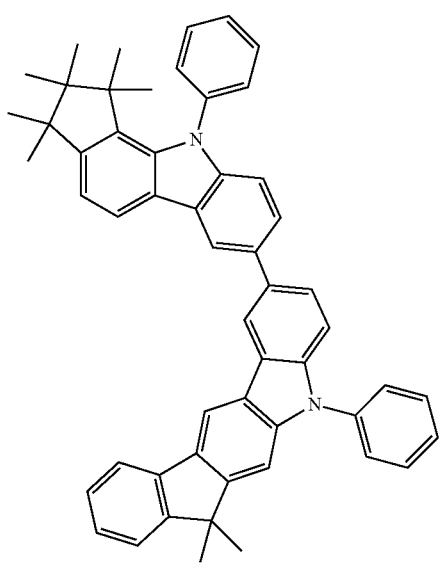
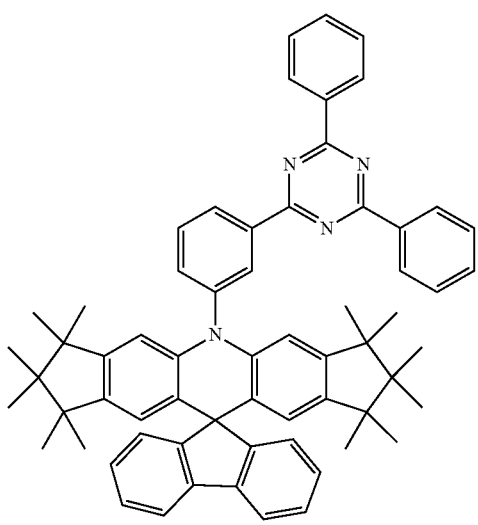
42
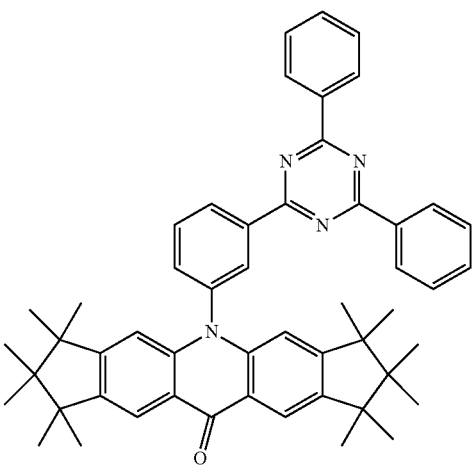
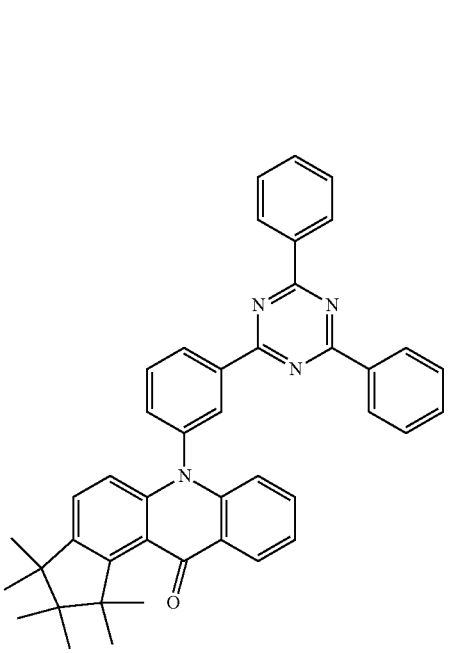
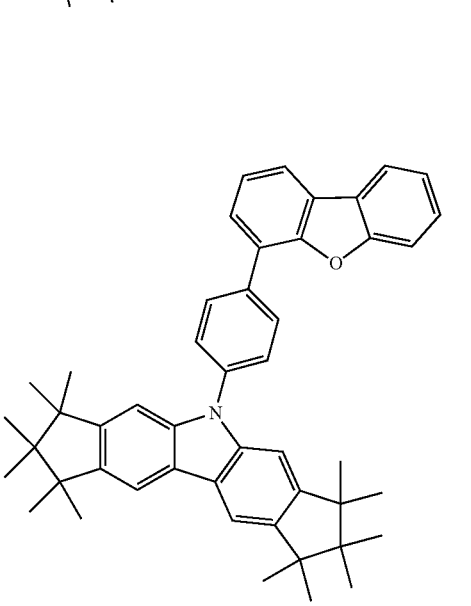

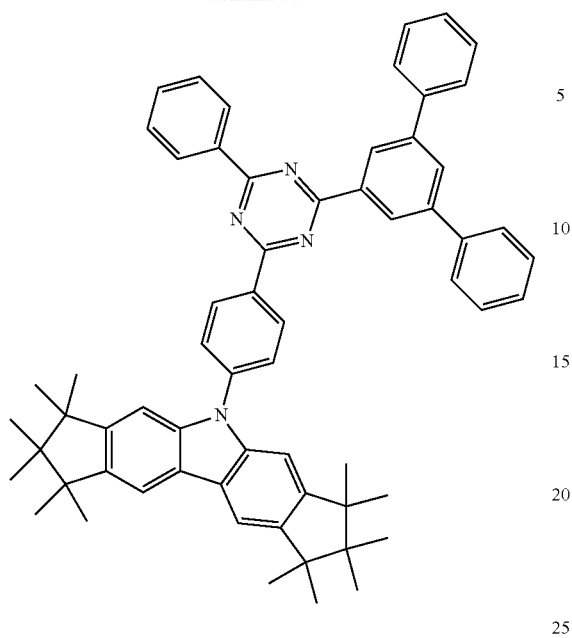
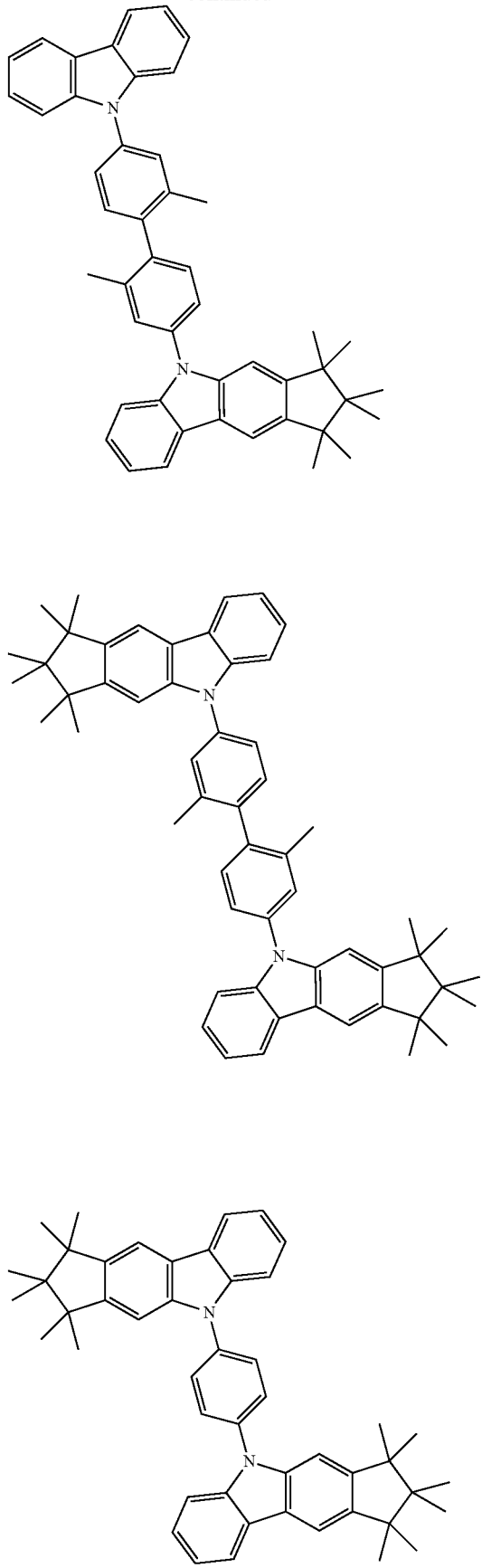

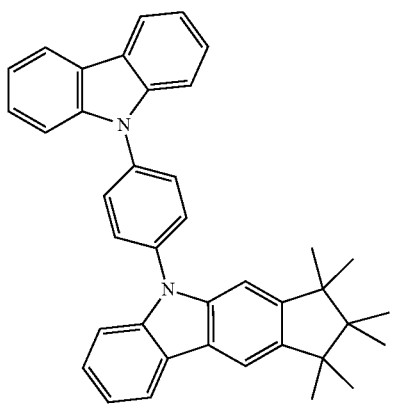
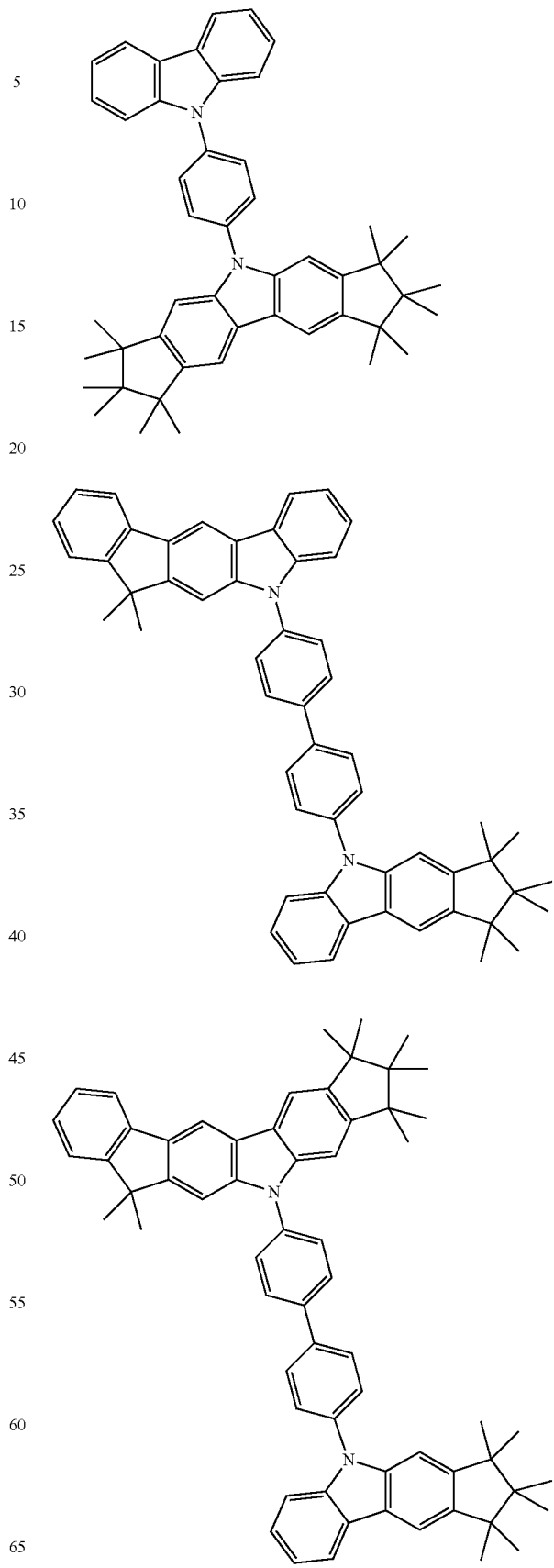

-continued
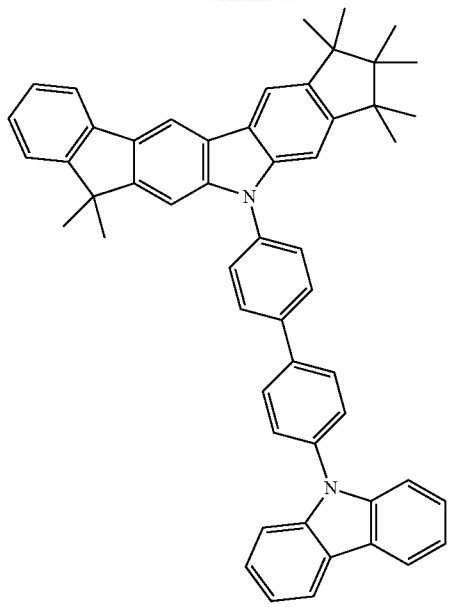
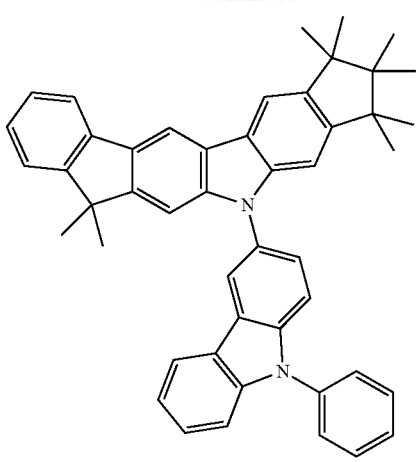
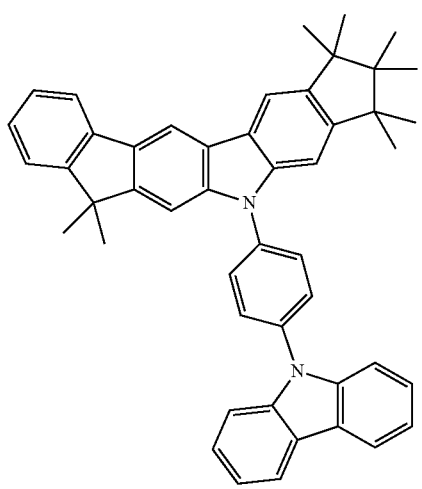
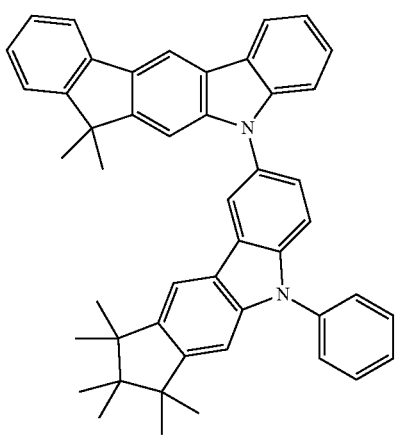
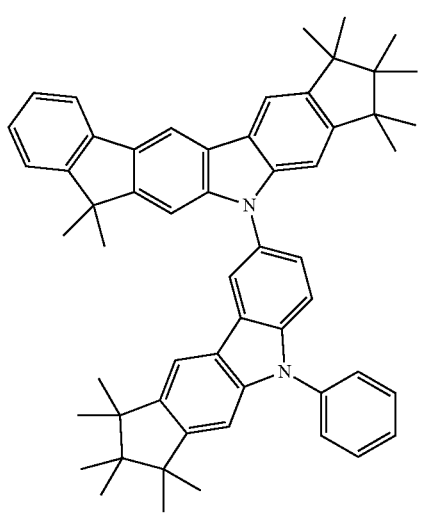
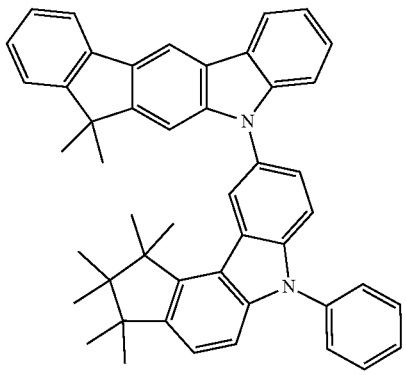

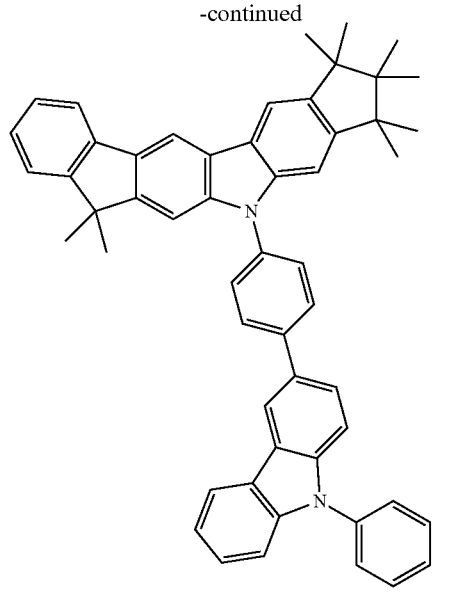
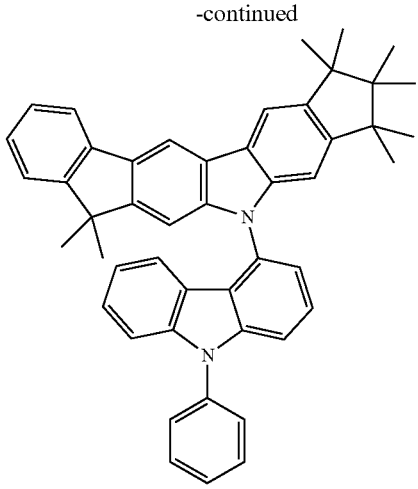
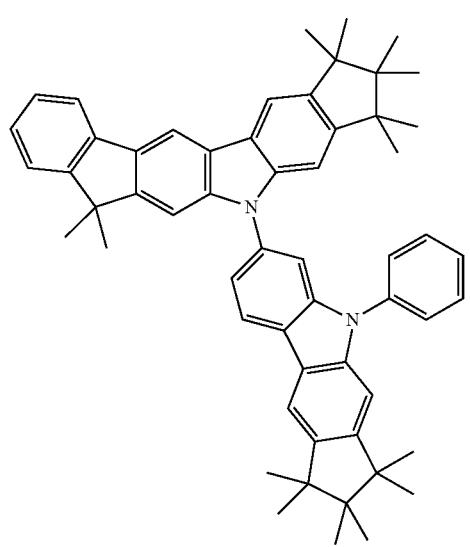
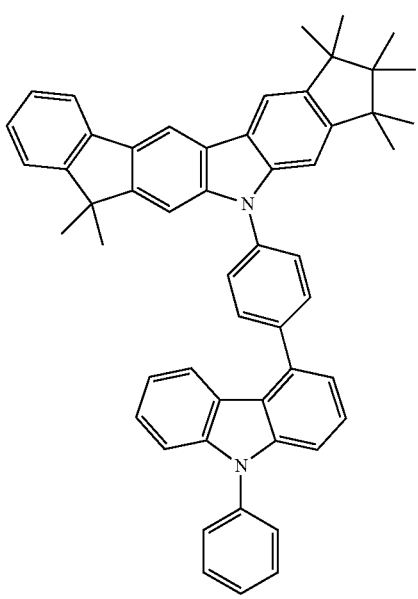
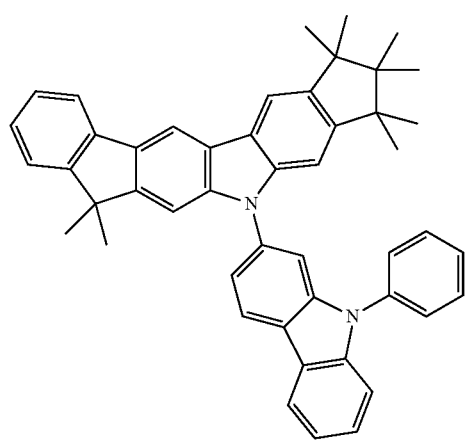
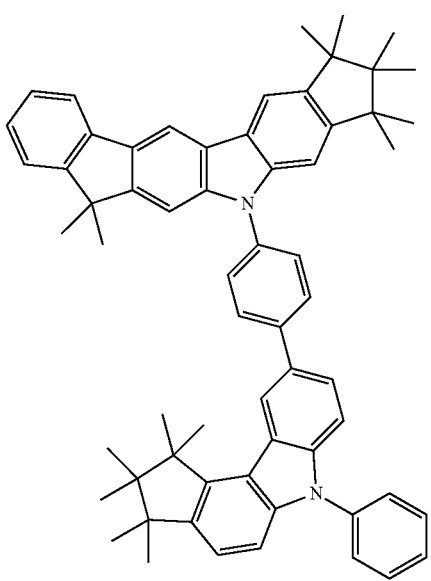

51
-continued
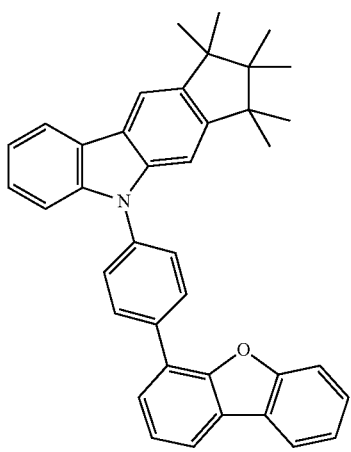
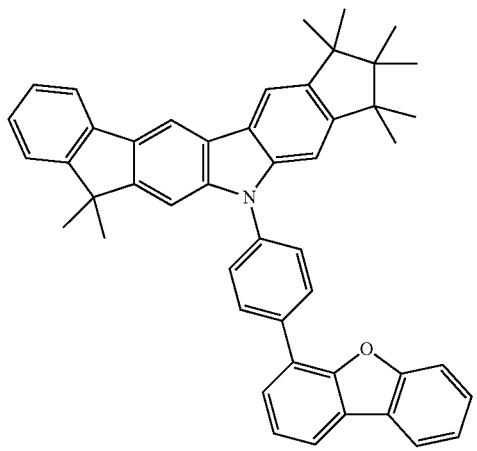
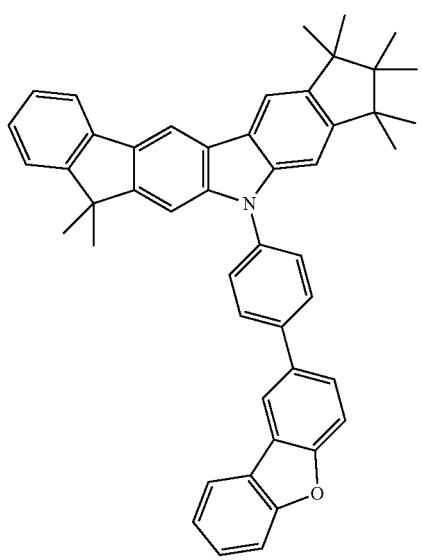
52
-continued
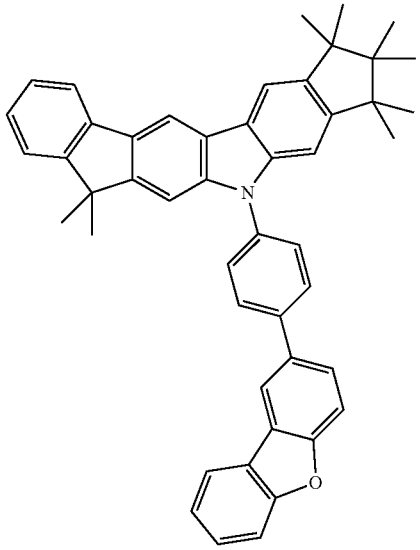
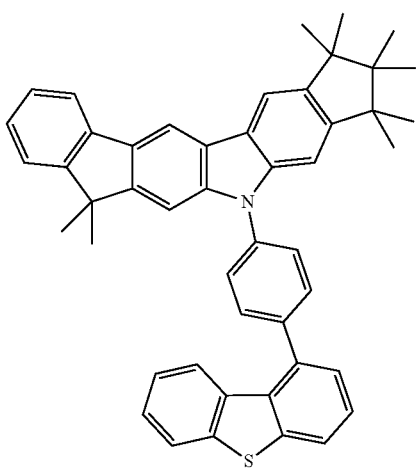
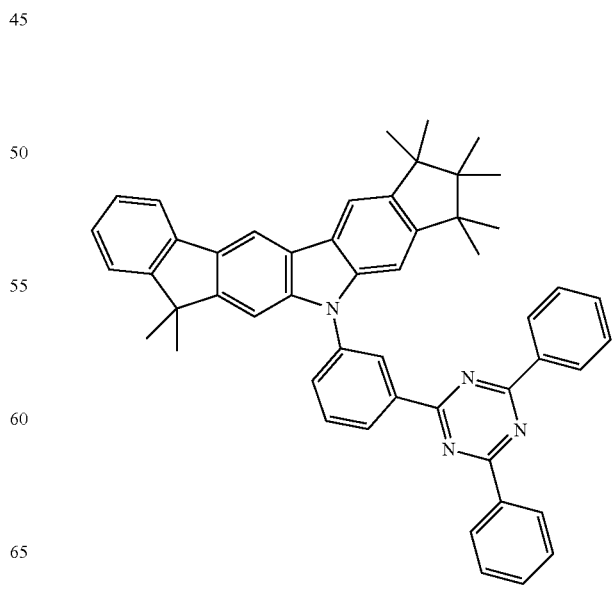

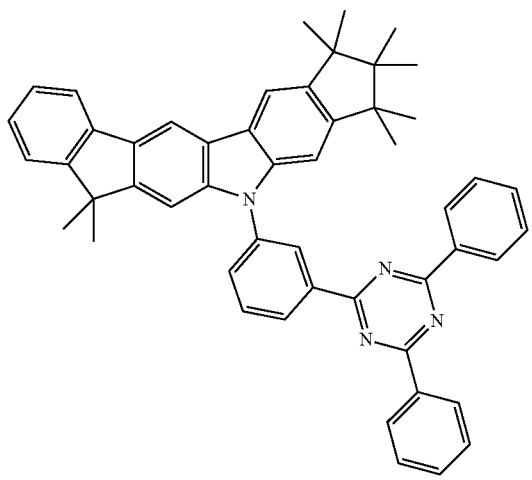
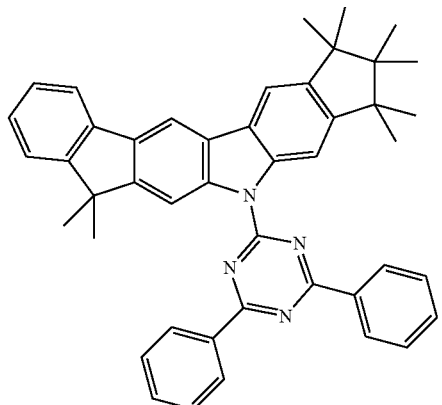
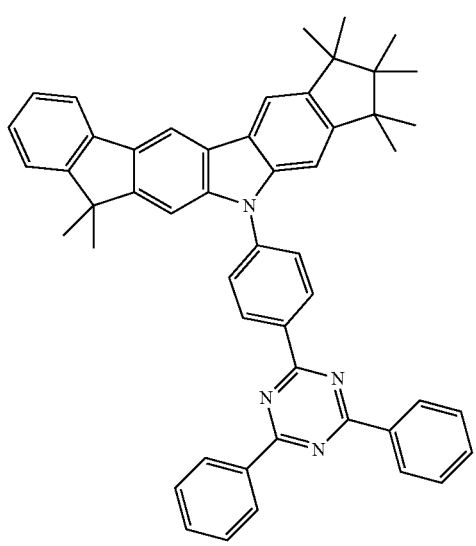
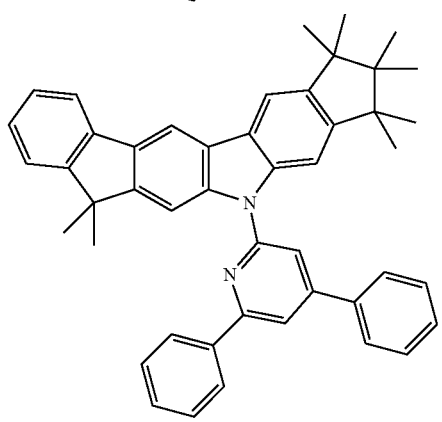
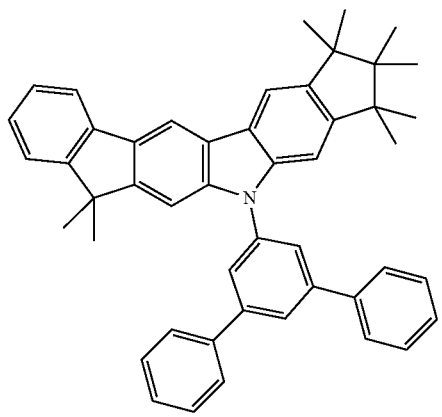
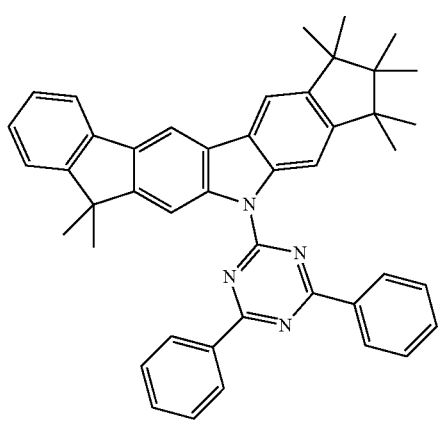
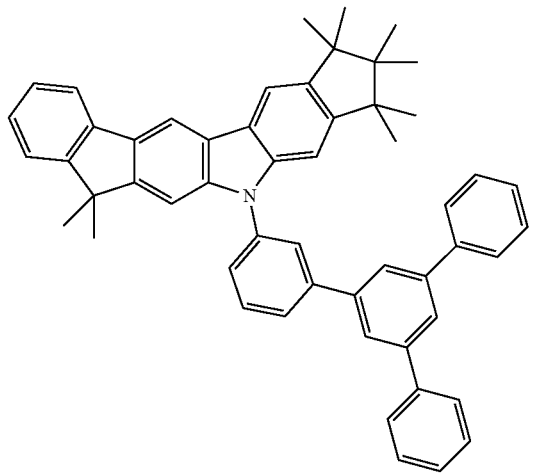

-continued
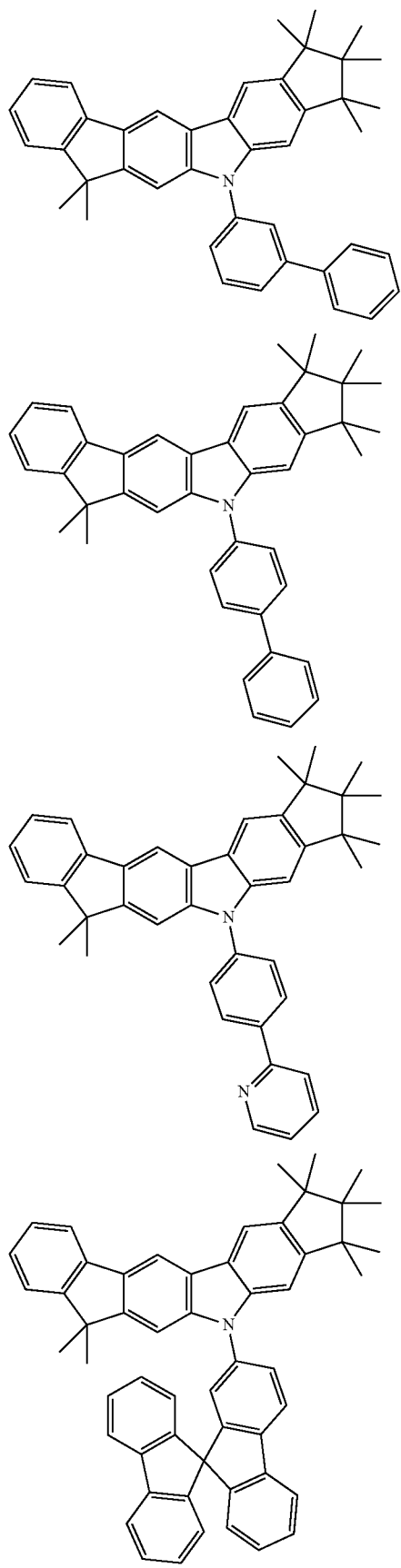
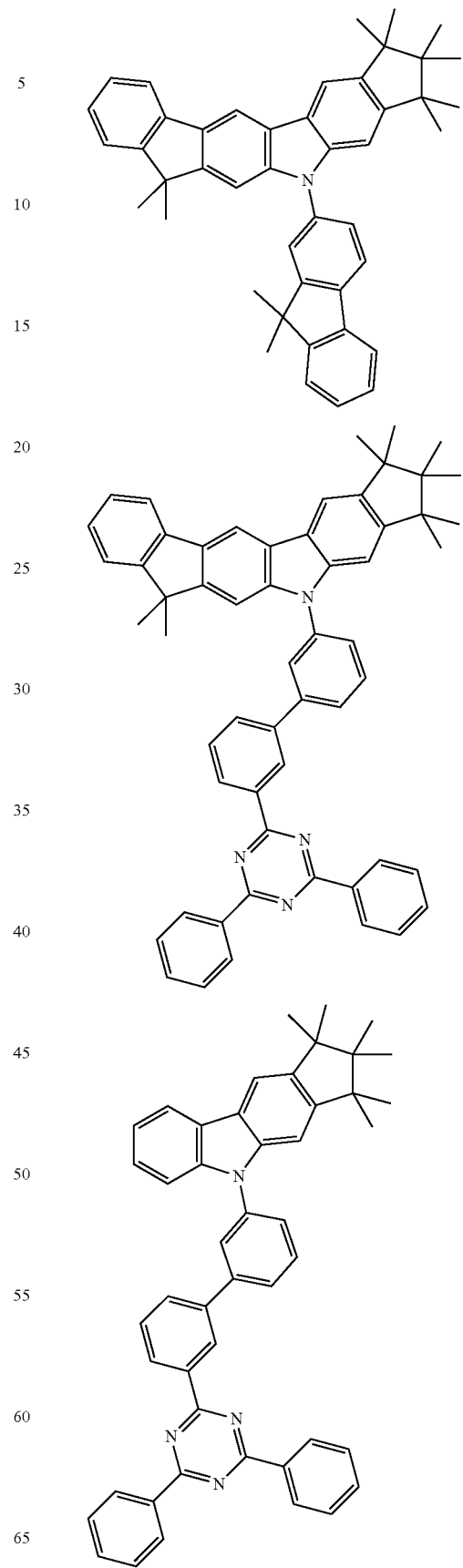

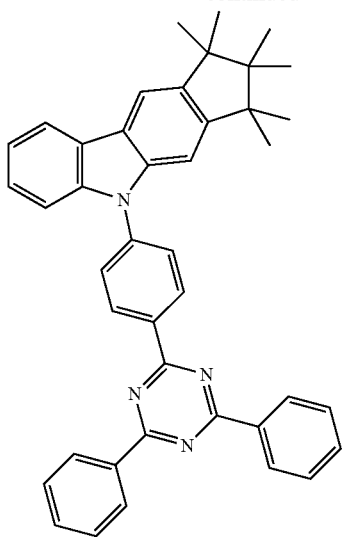
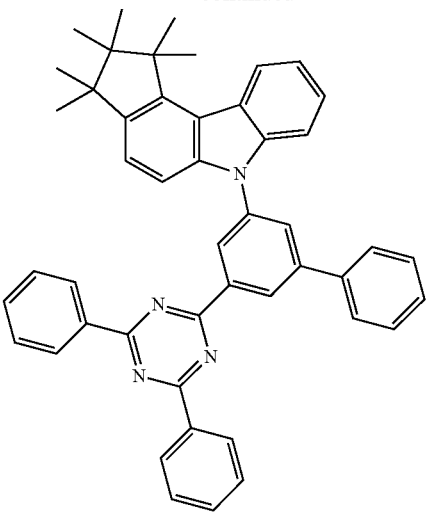
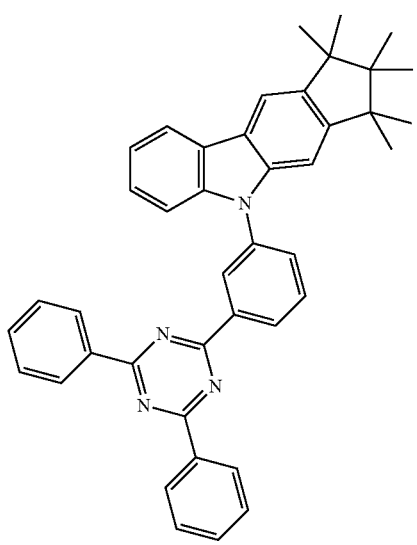
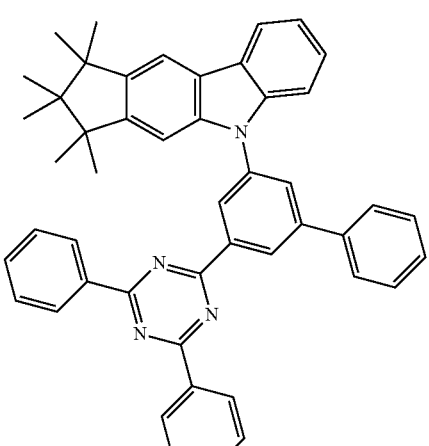
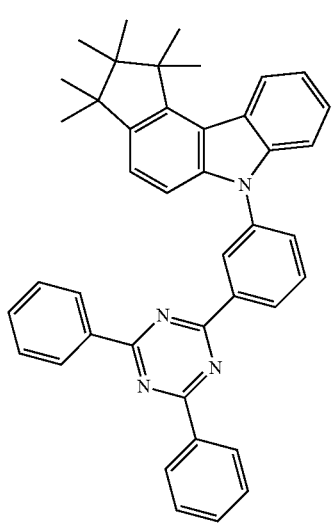
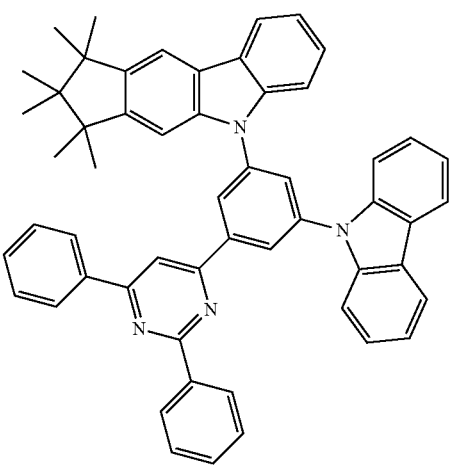

-continued
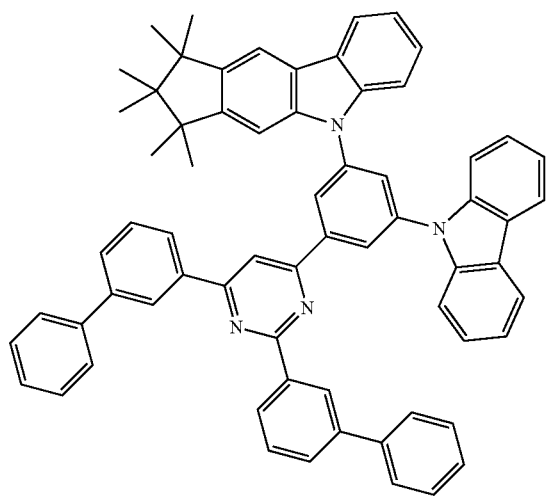
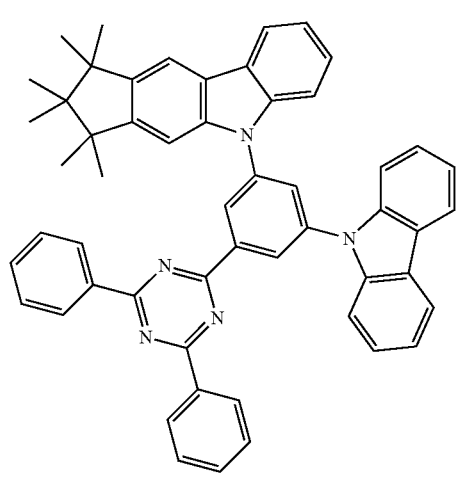 [SMILES: CC1(C)c2cc3c4ccccc4n(-c4cc(-c5nc(-c6ccccc6)nc(-c6ccccc6)n5)cc(-n5c6ccccc6c6ccccc65)c4)c3cc2C(C)(C)C1(C)C]
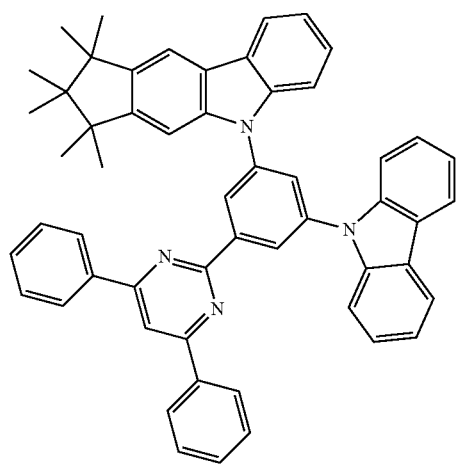
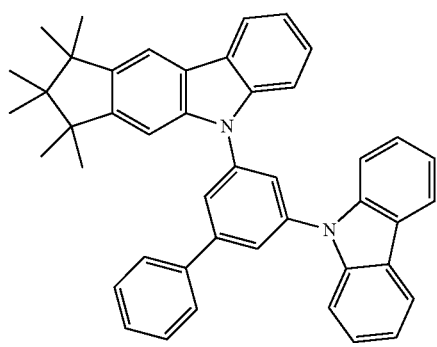
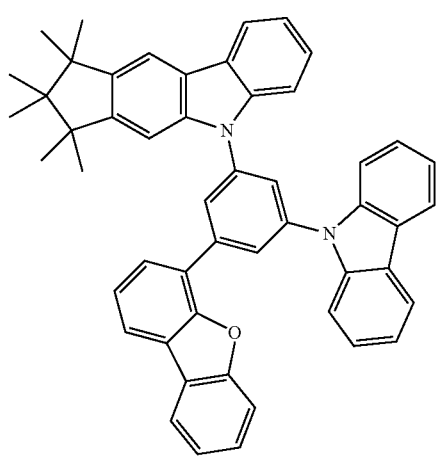
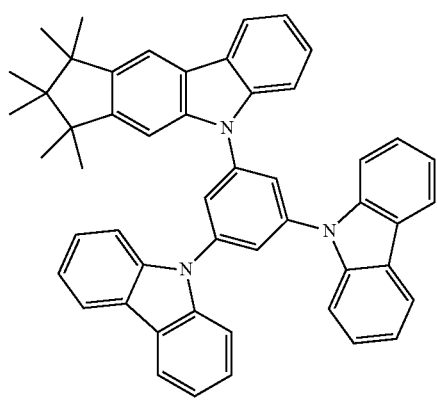
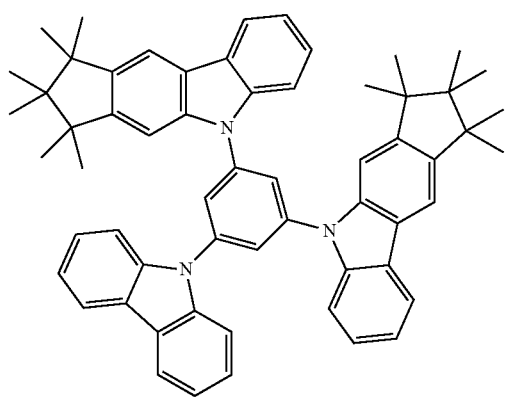

61
-continued
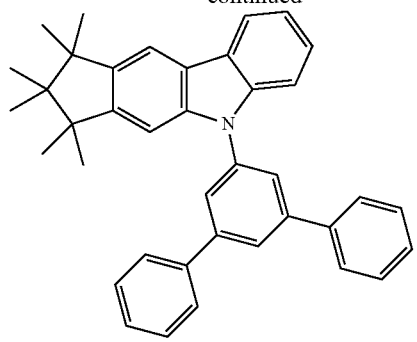
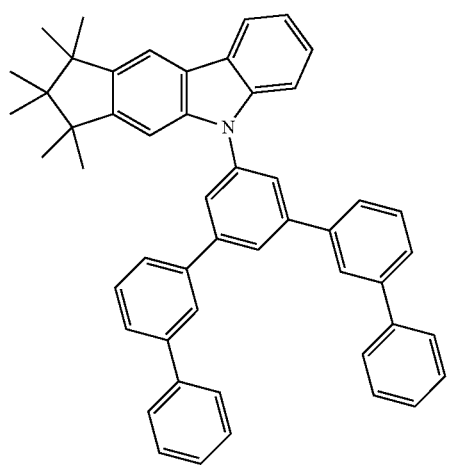
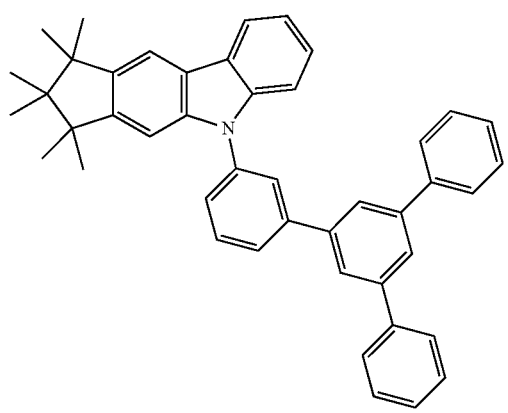
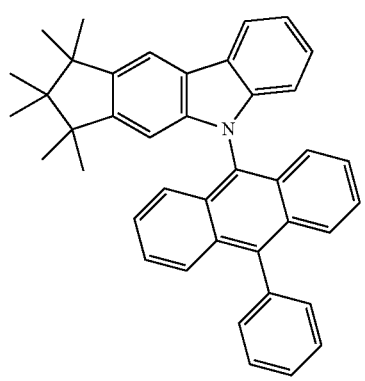
62
-continued
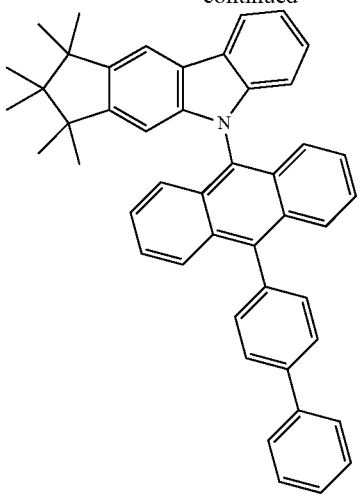
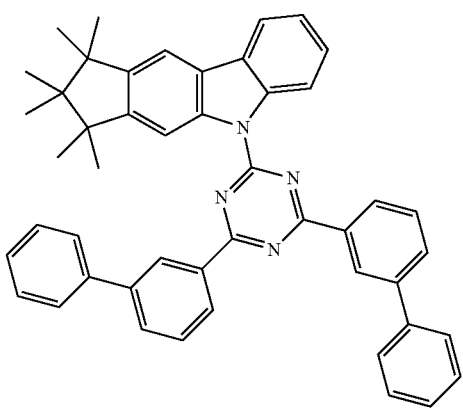
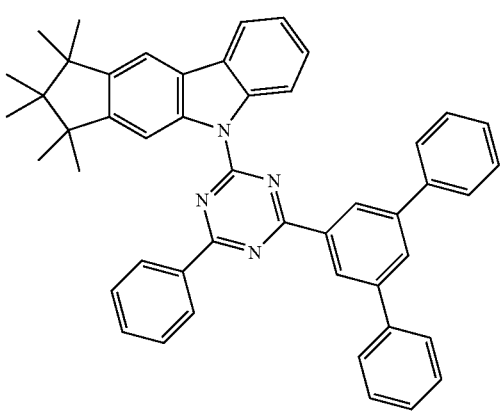

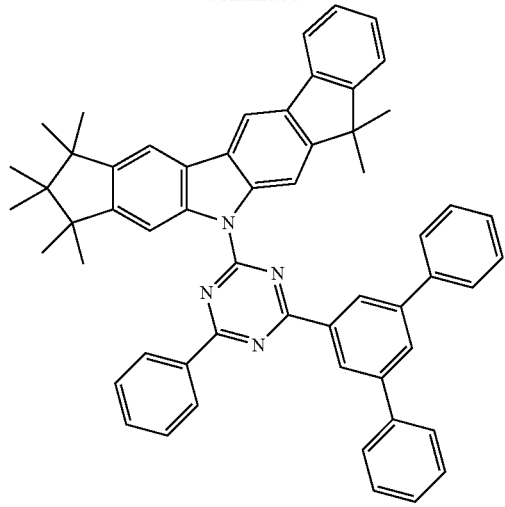
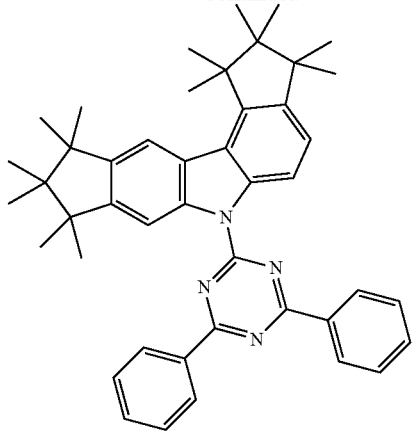
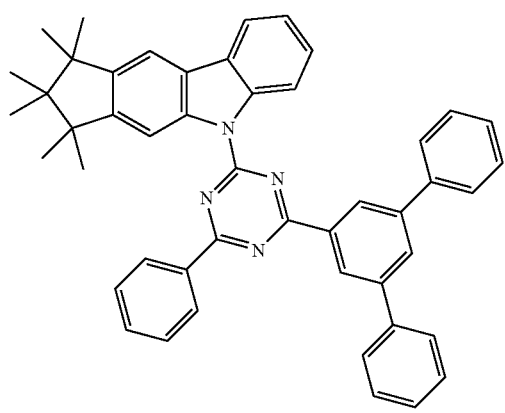
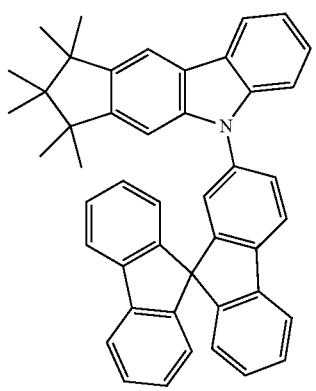
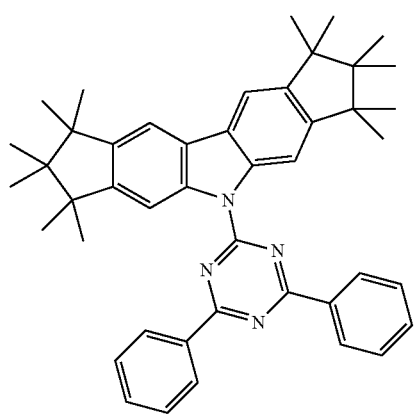

65
-continued
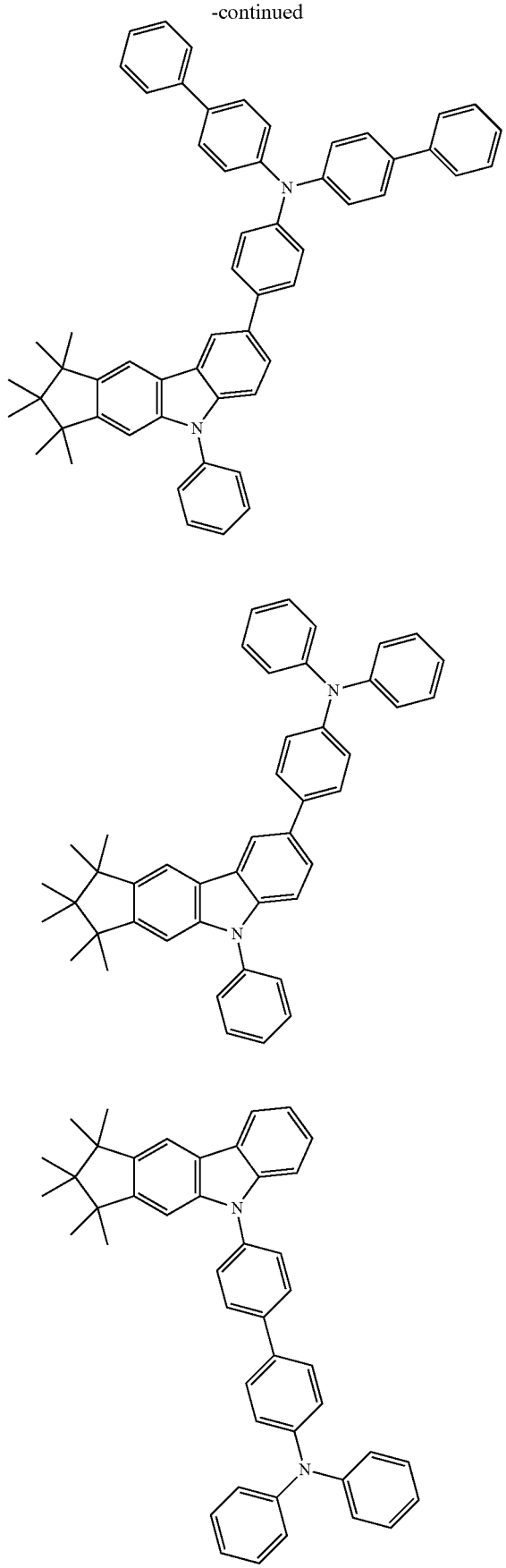
66
-continued
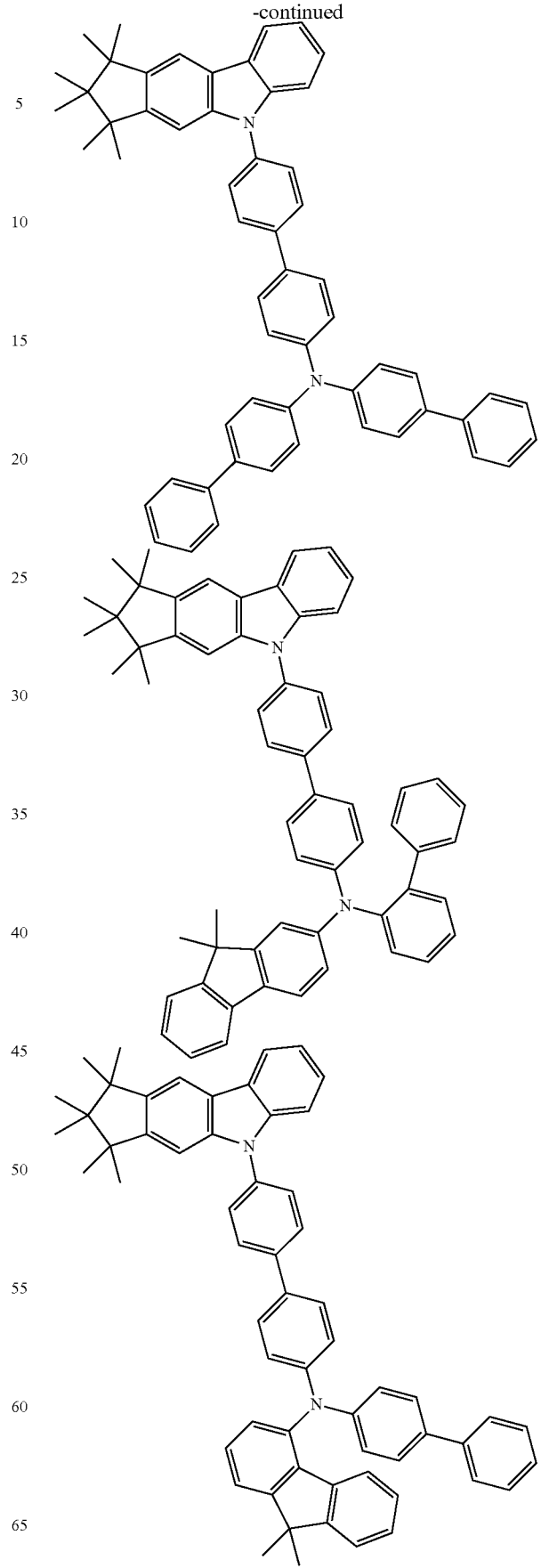

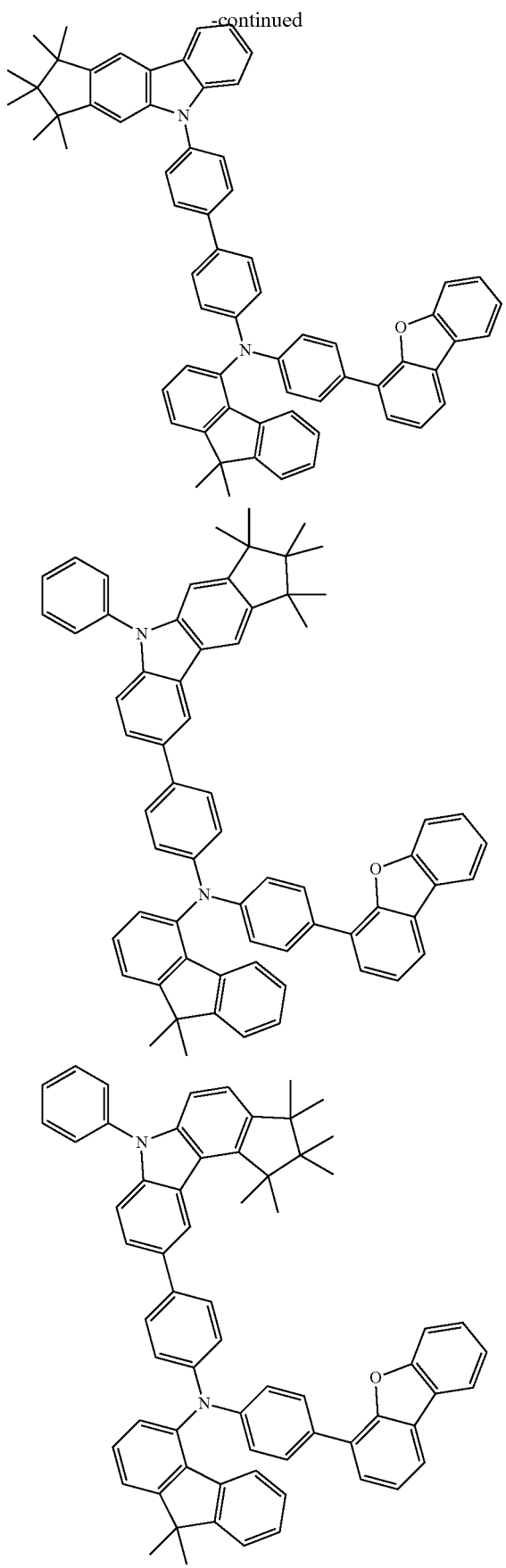
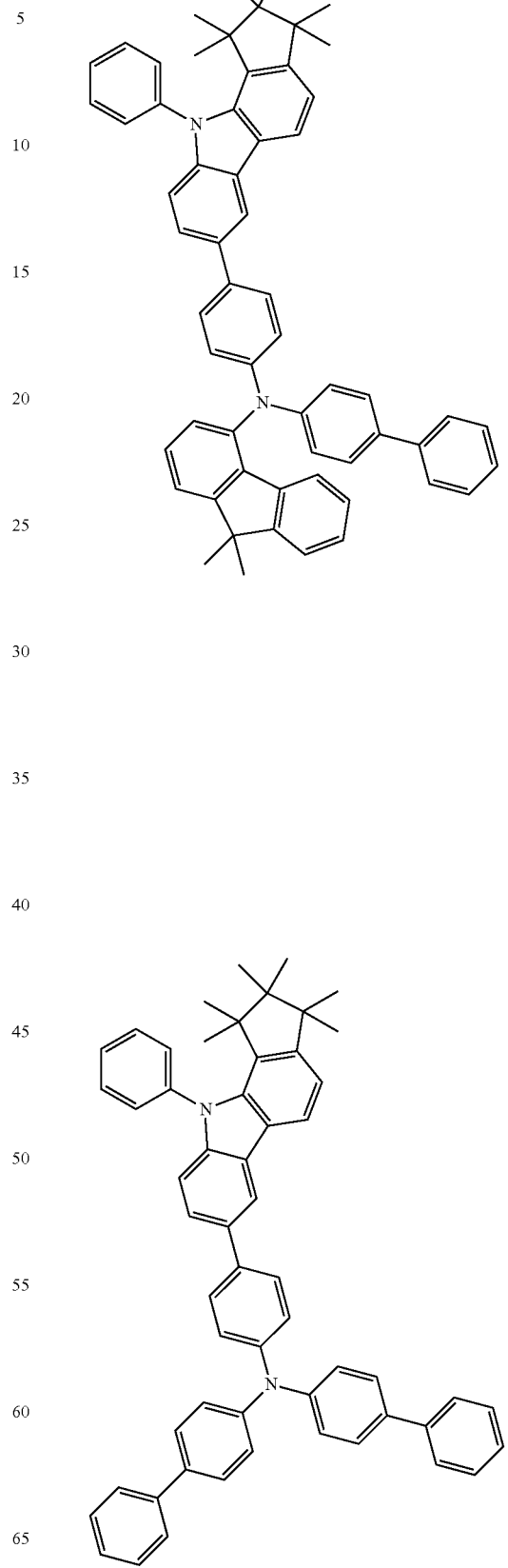

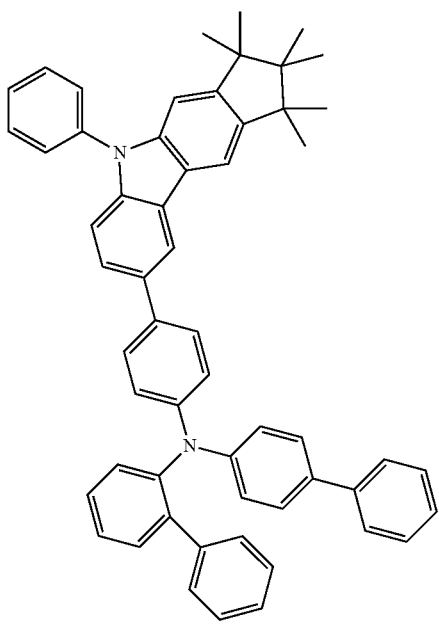
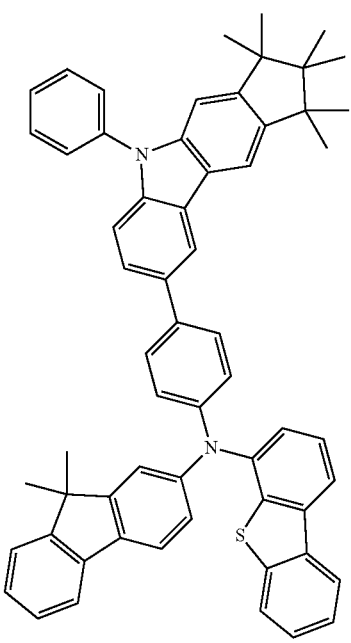
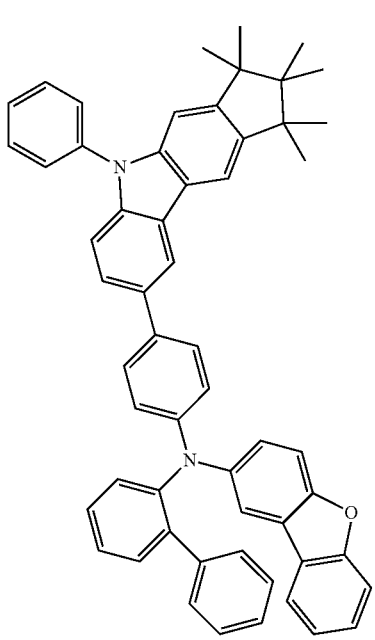
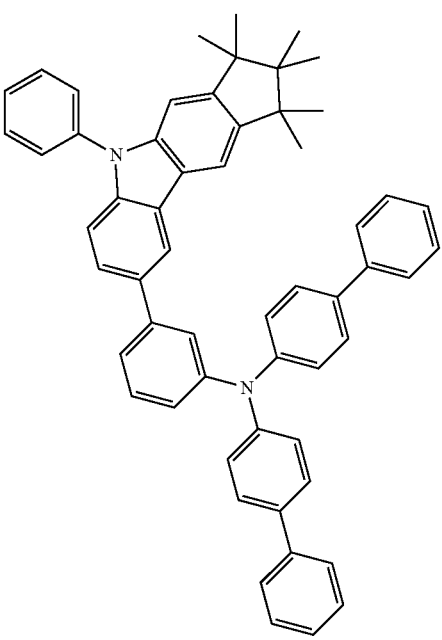

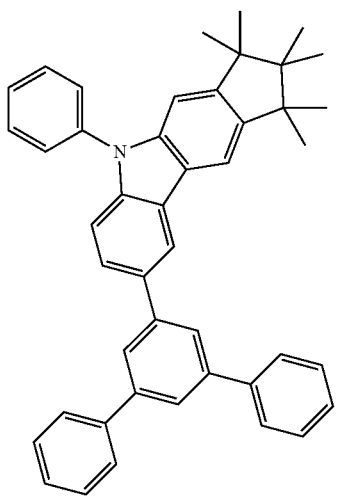
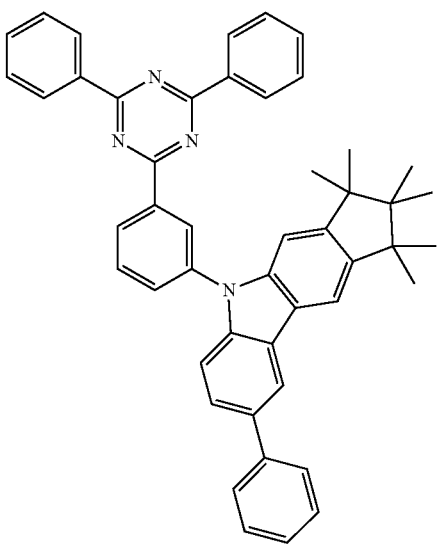
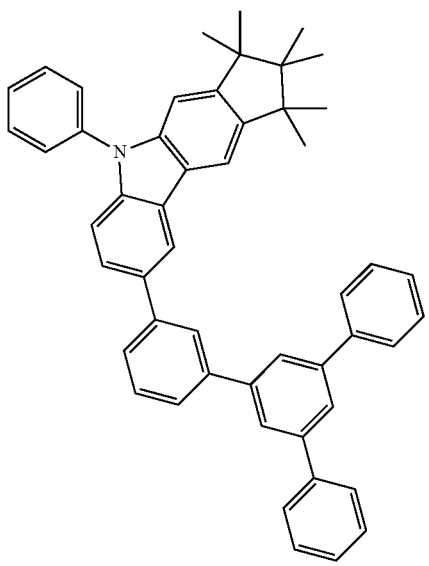
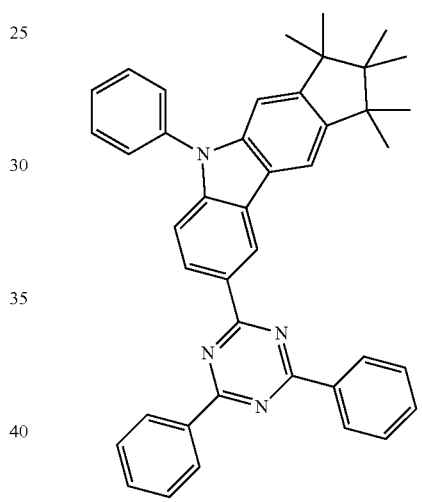
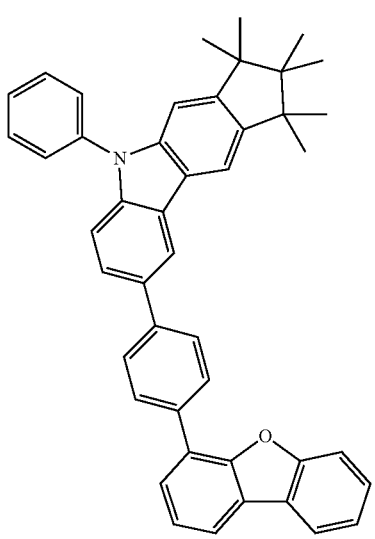
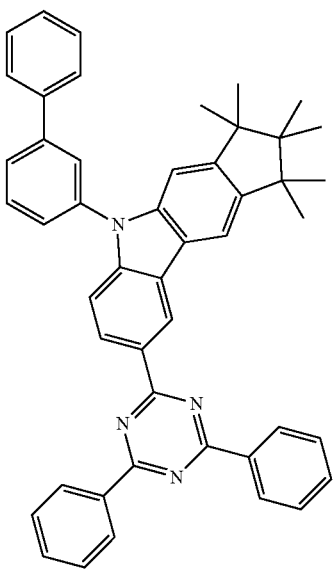

73
-continued
74
-continued
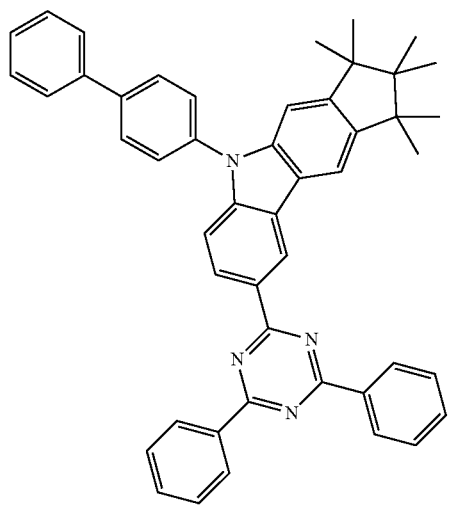
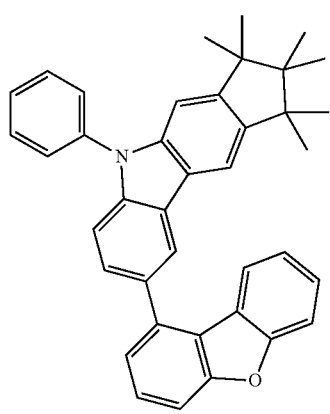
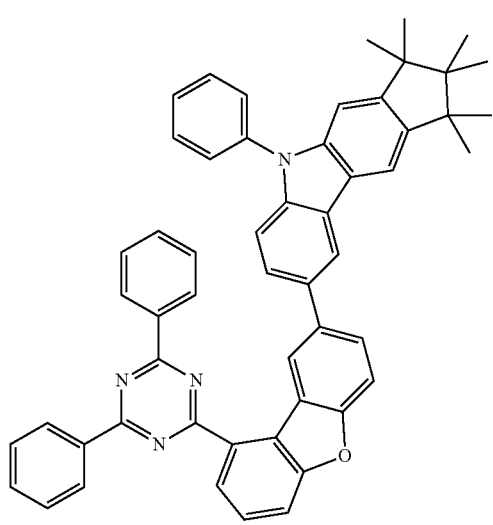
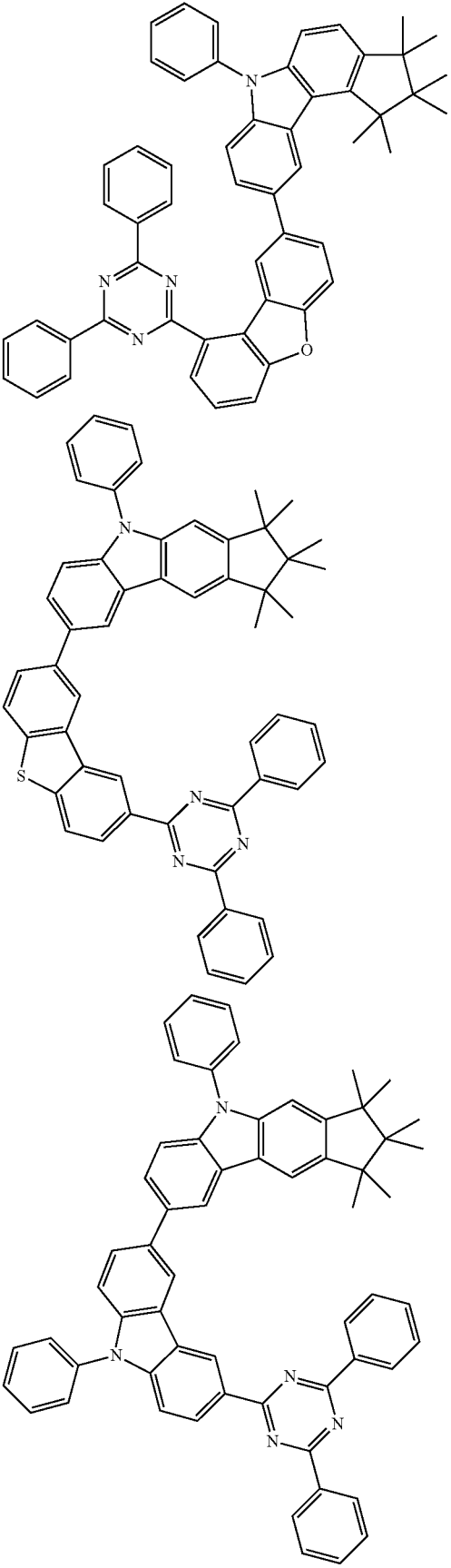

75
-continued
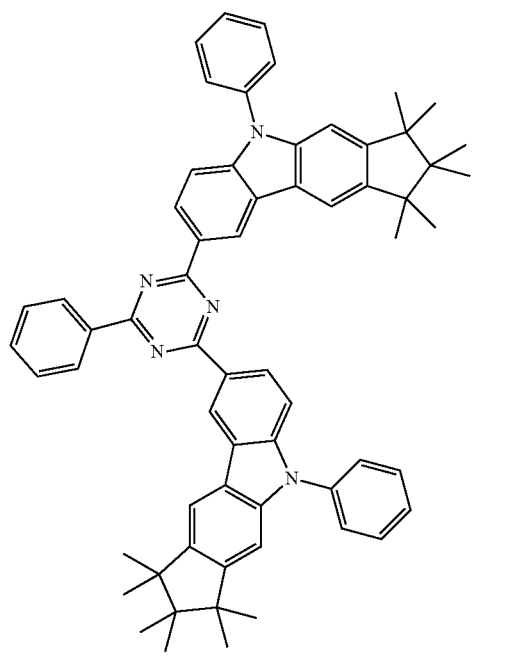
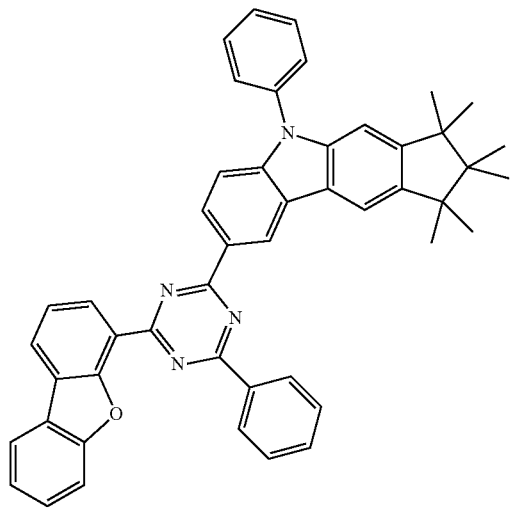
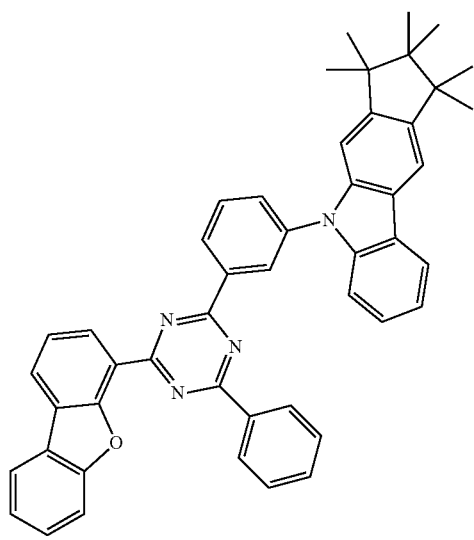
76
-continued
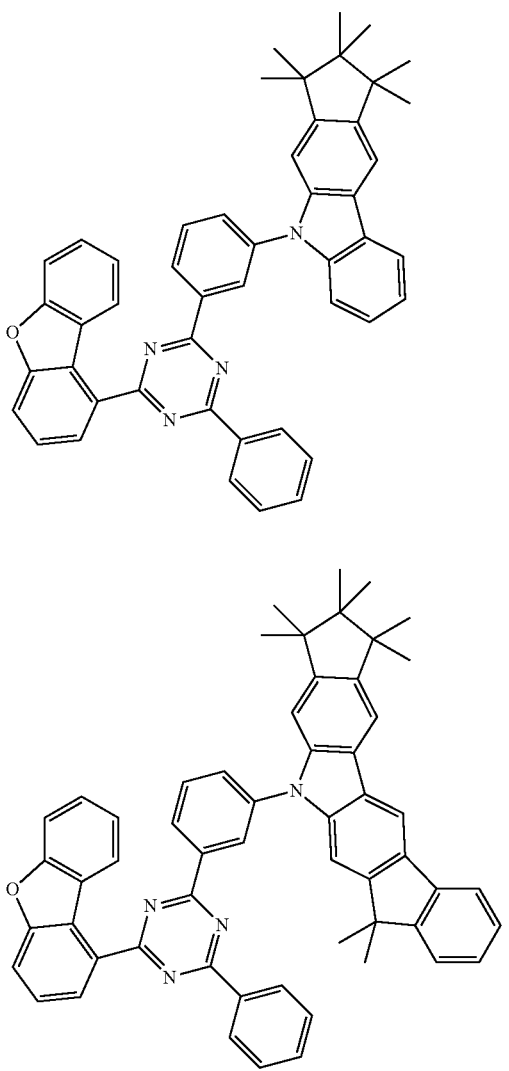
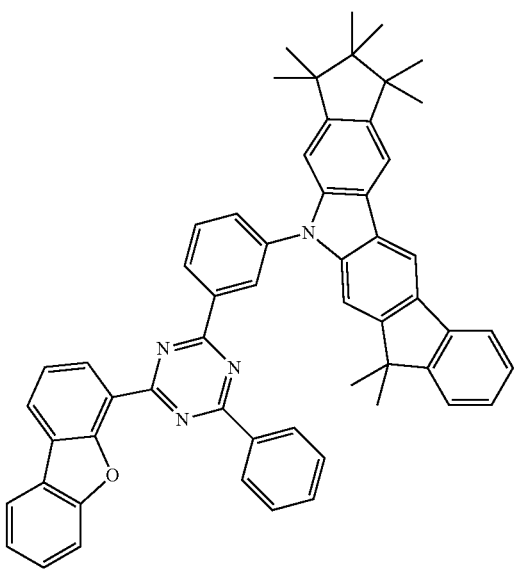

77
-continued
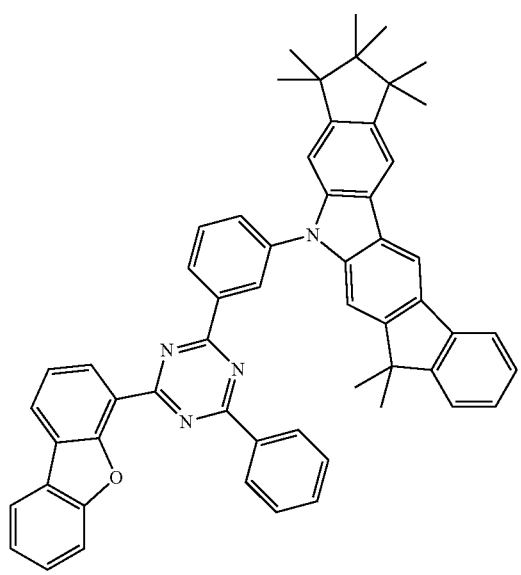
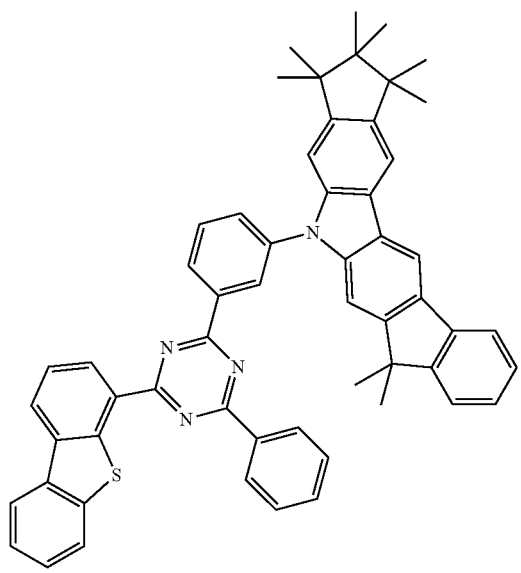
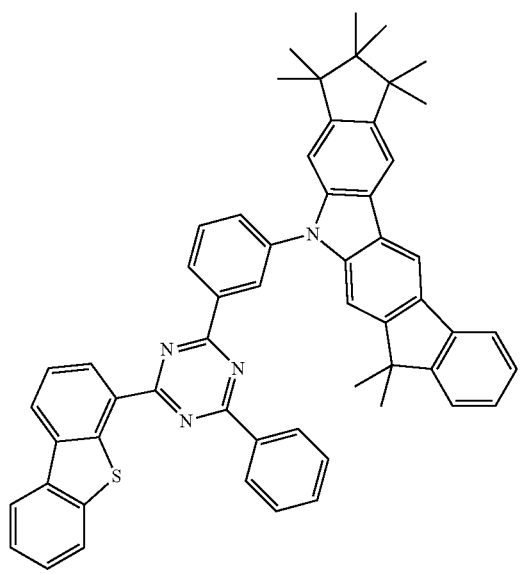
78
-continued
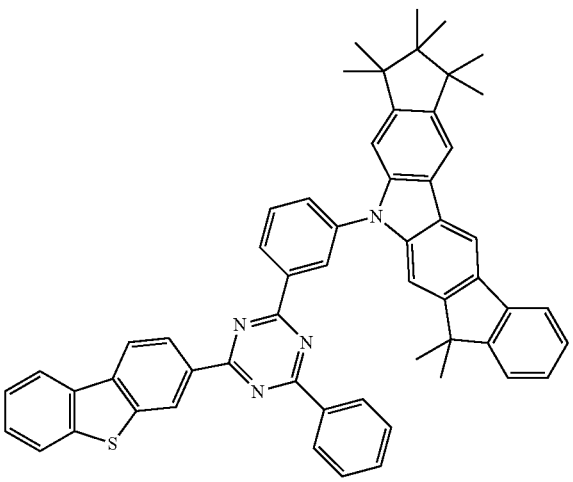
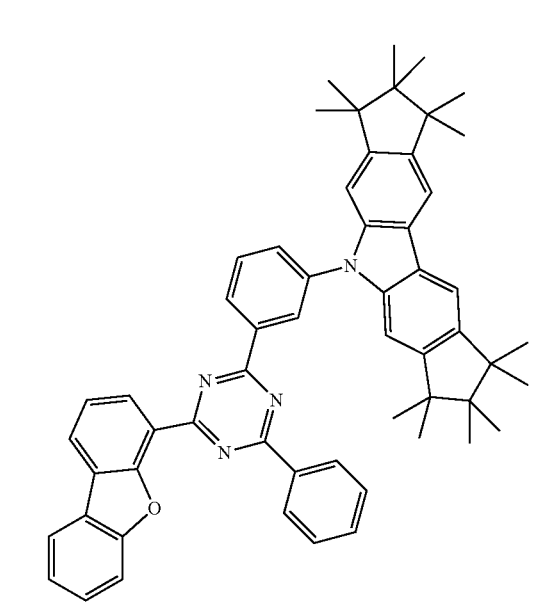
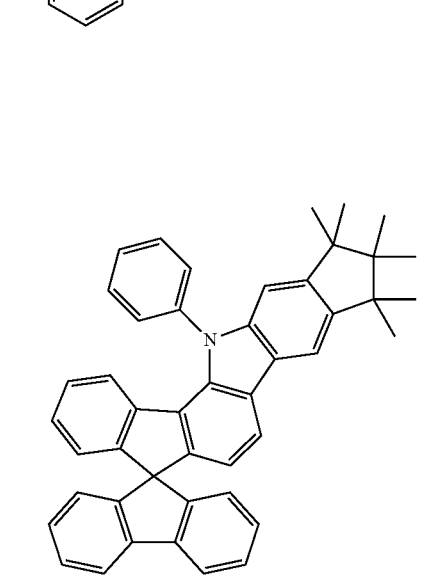

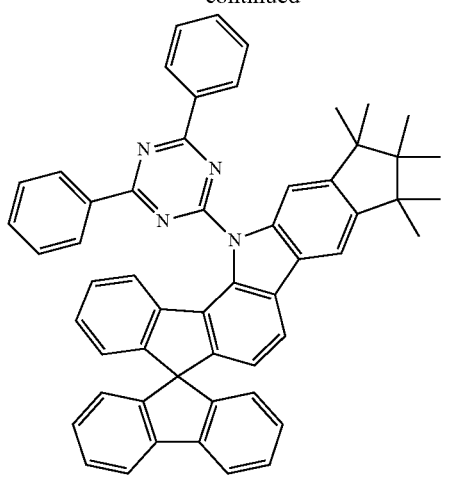
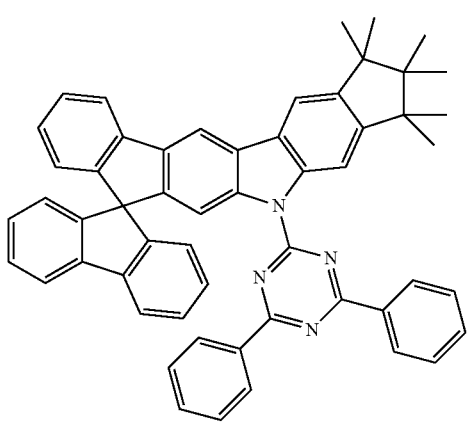
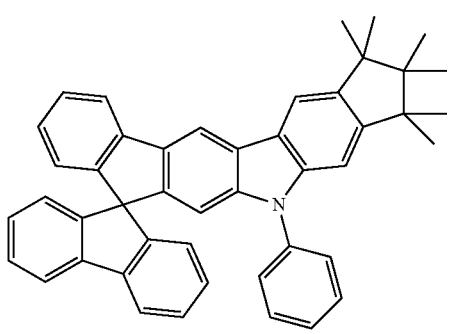
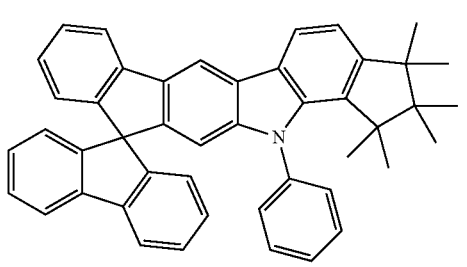
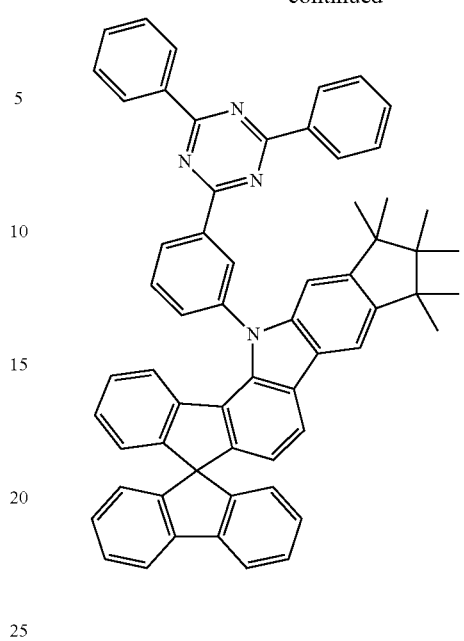
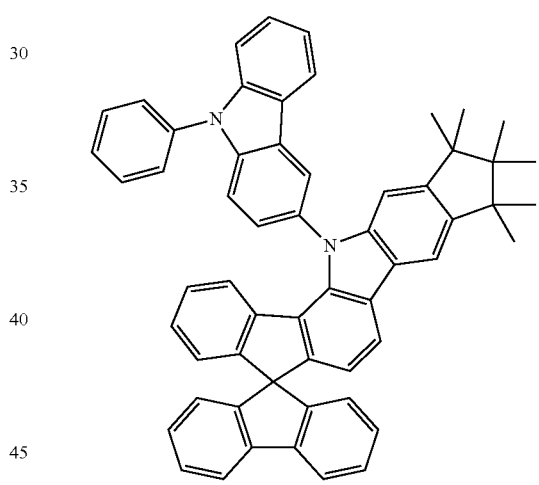
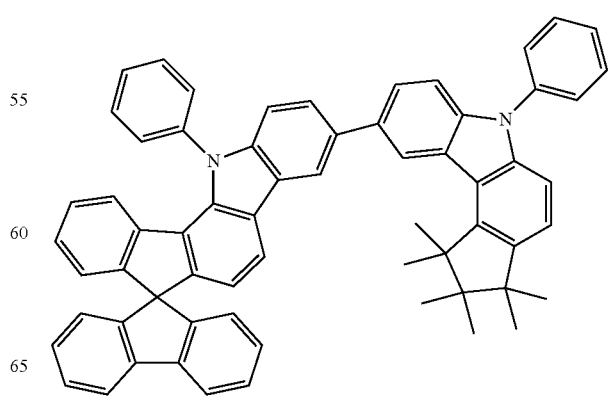

81
-continued
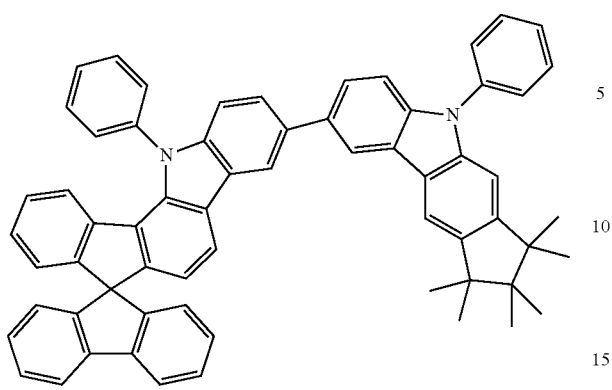
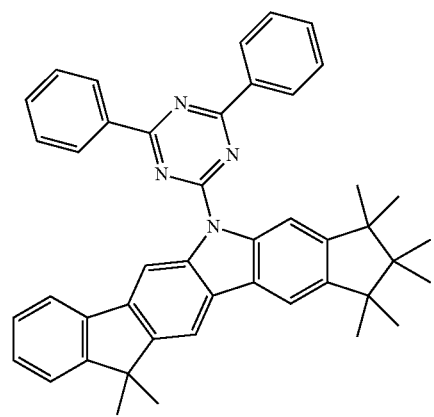
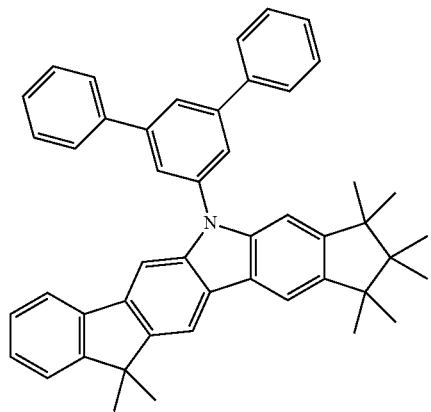
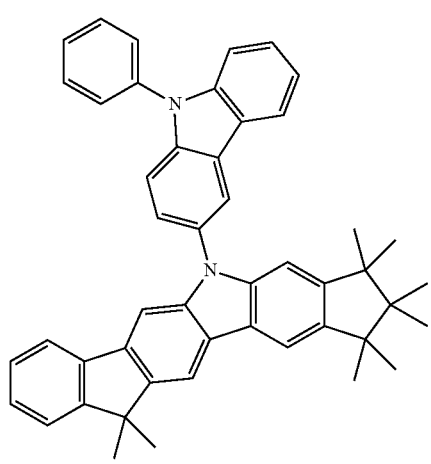
82
-continued
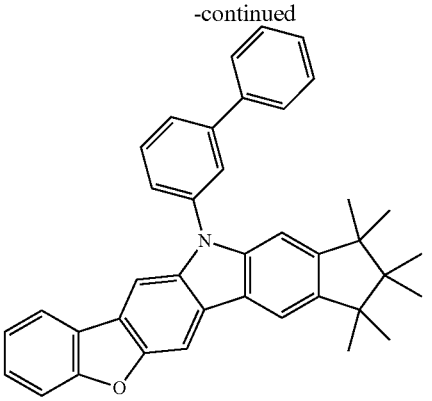
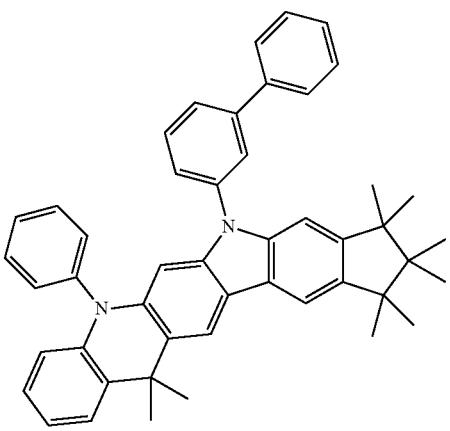
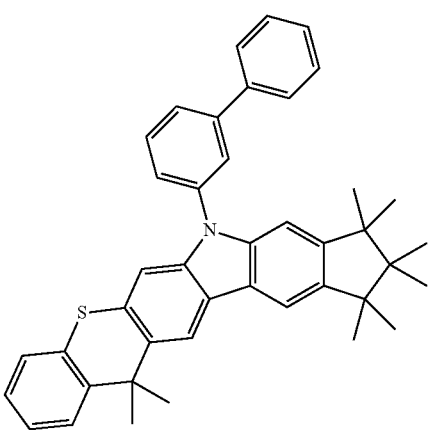
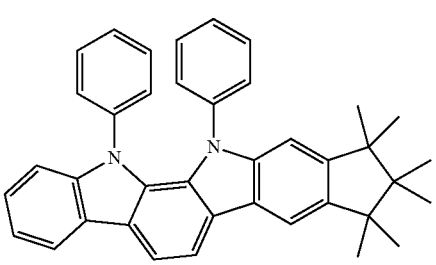

-continued
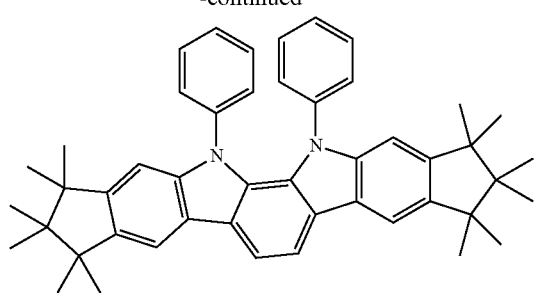
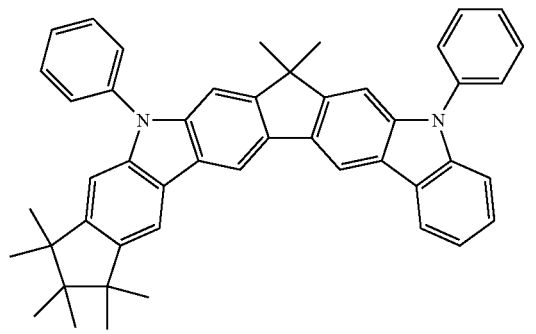
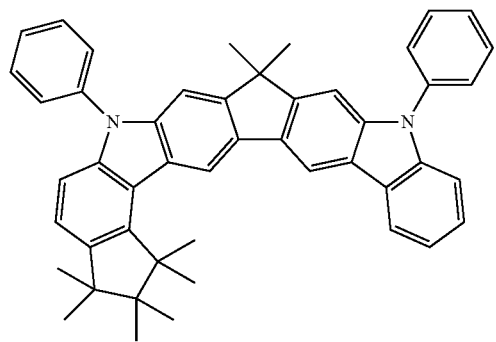
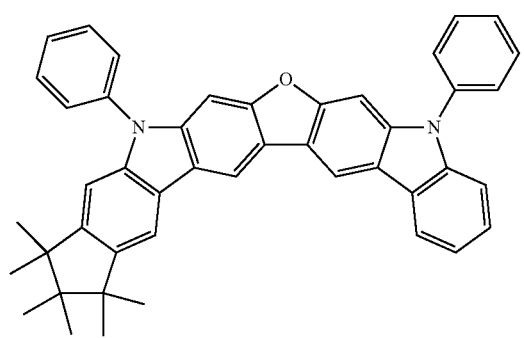
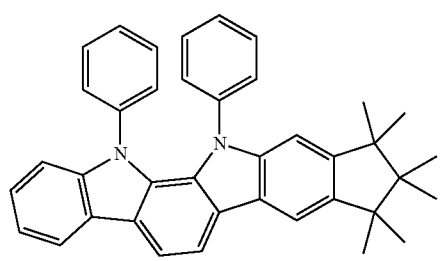
-continued
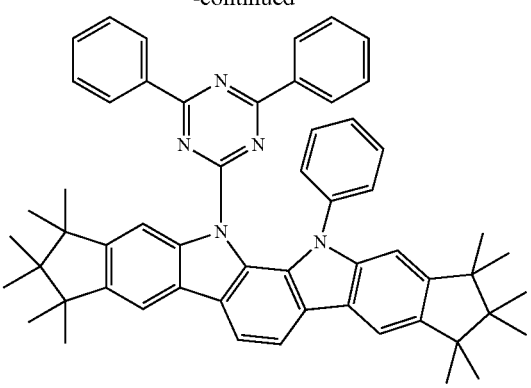
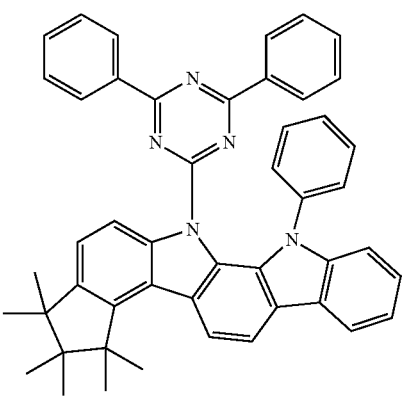
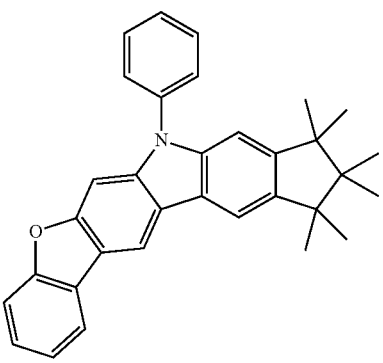
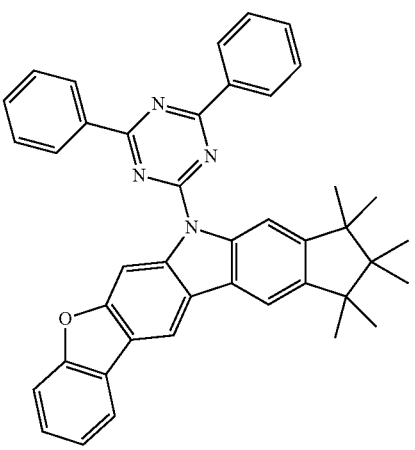

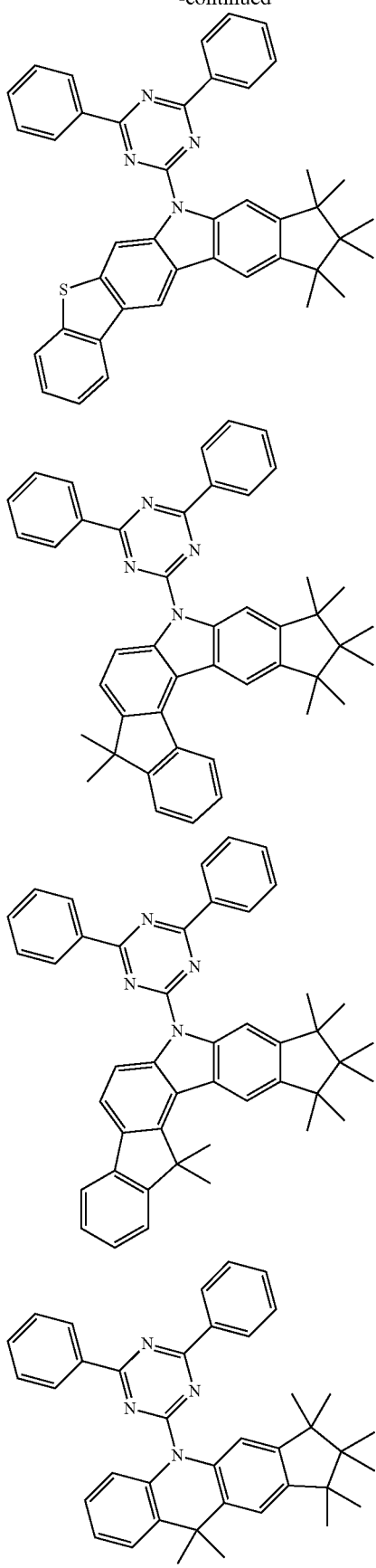
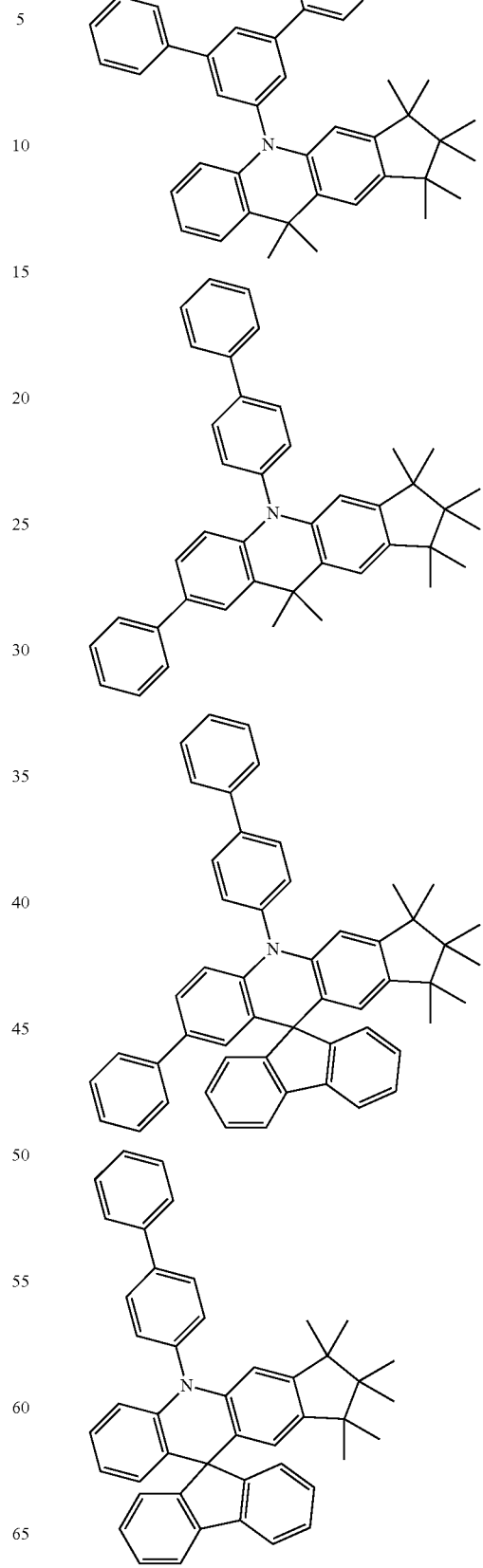

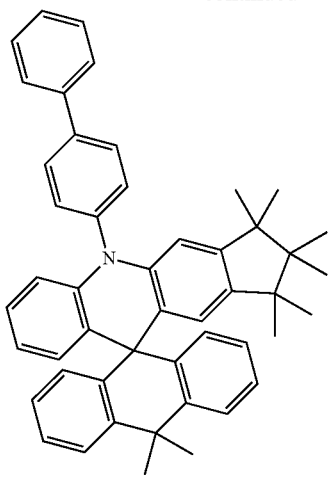
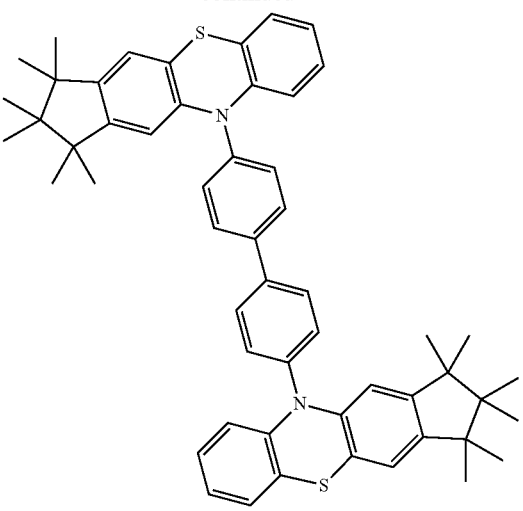
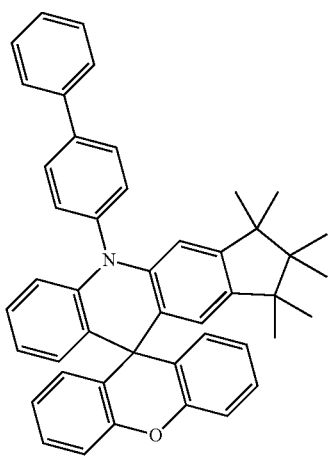
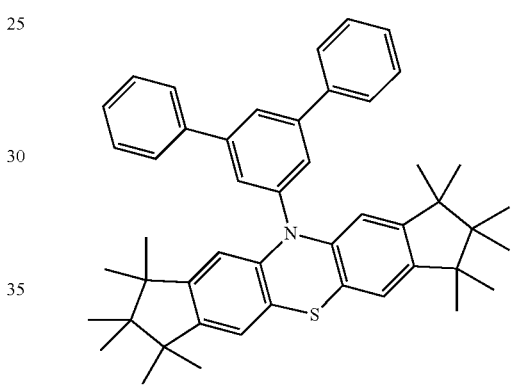
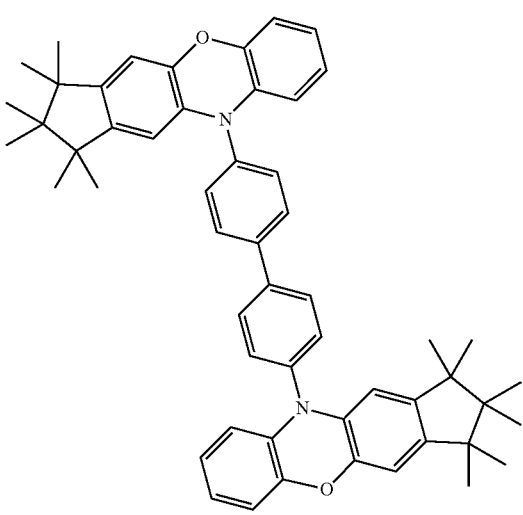
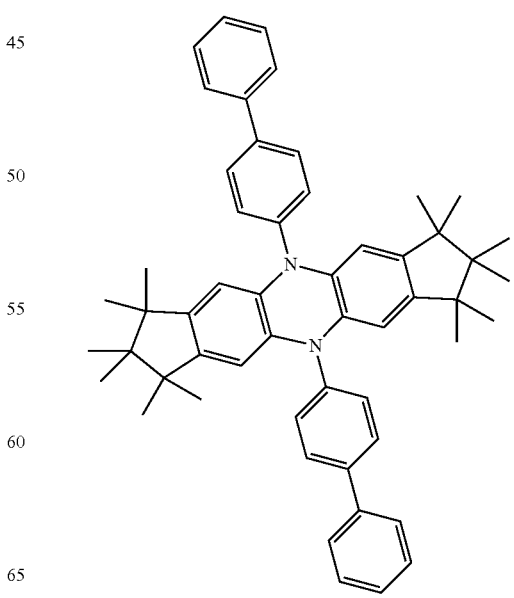

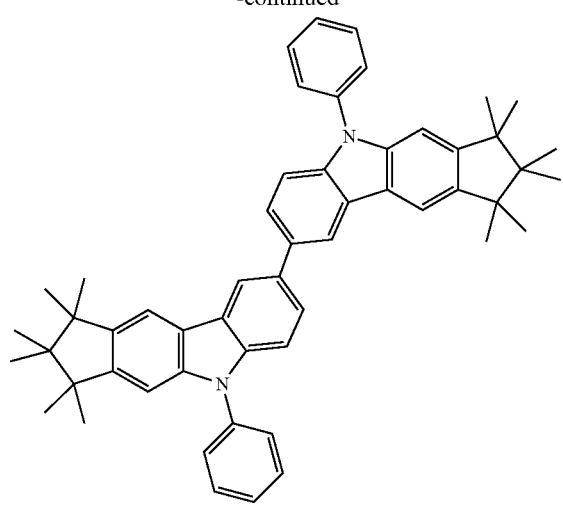
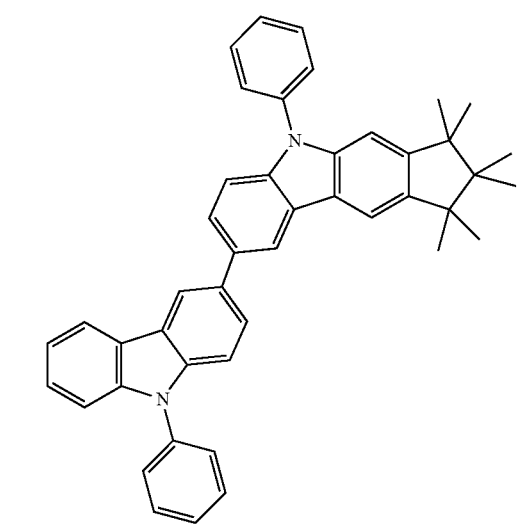
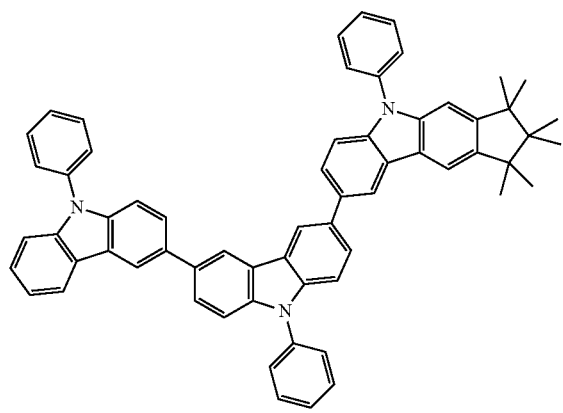
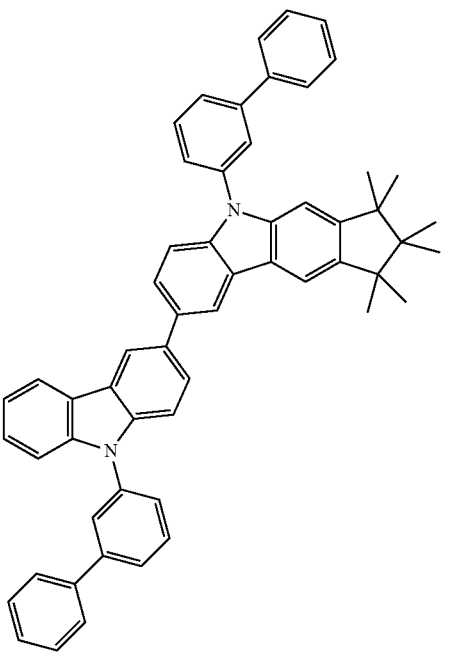
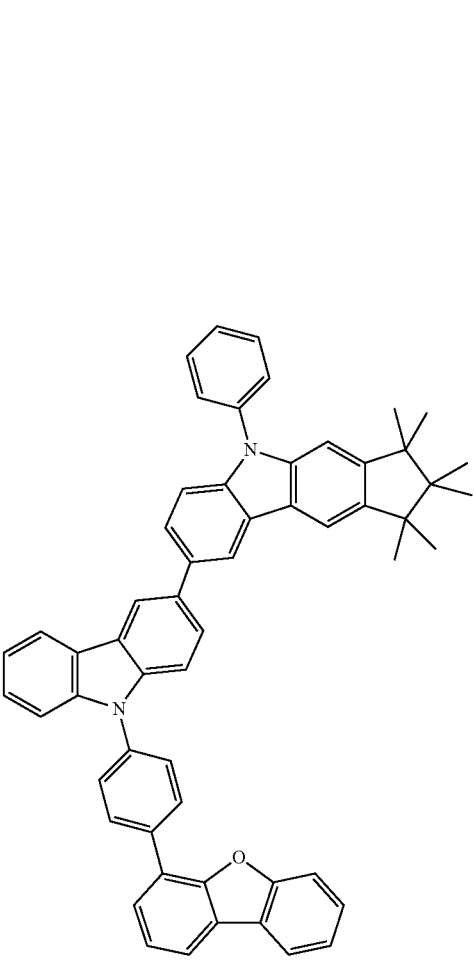

91
-continued
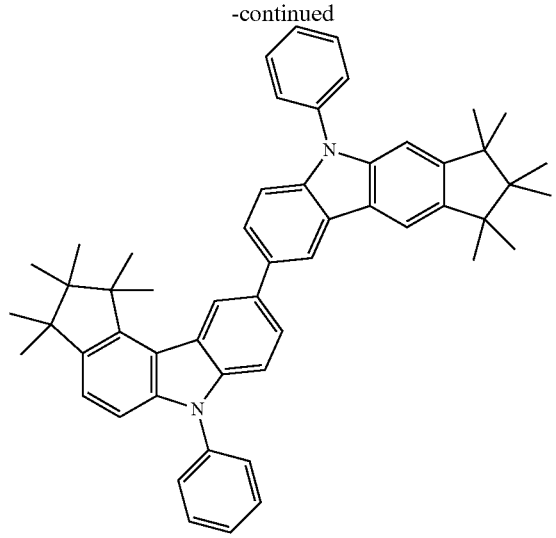
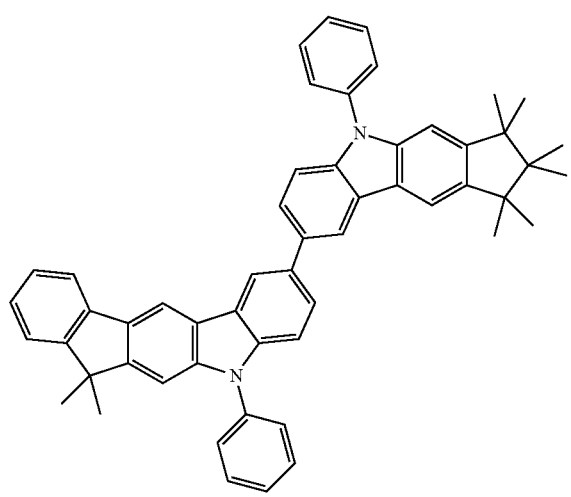
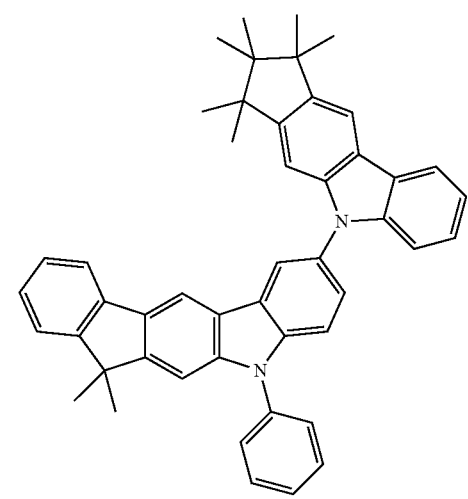
92
-continued
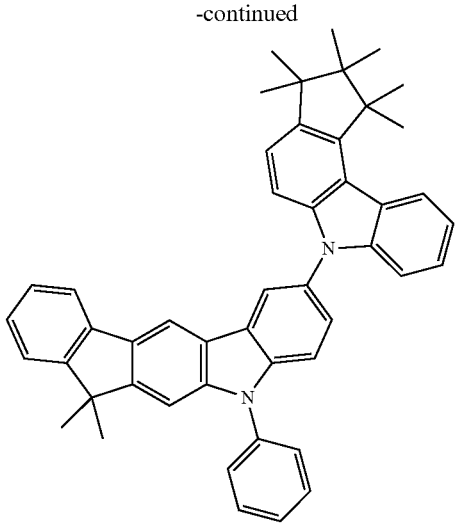
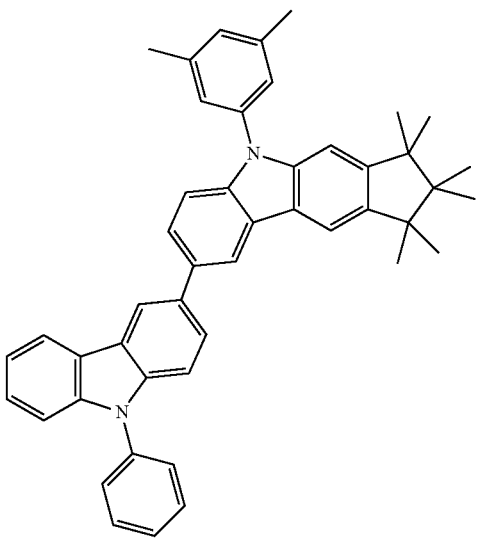
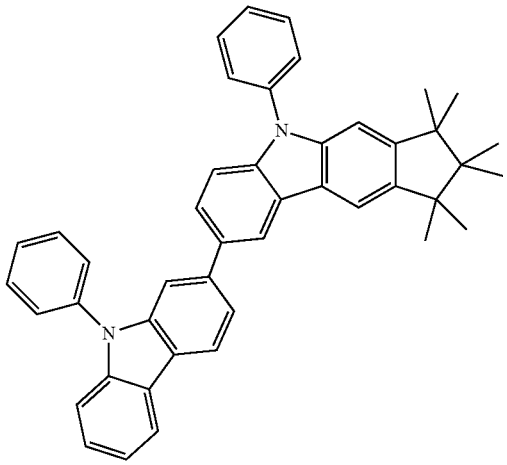

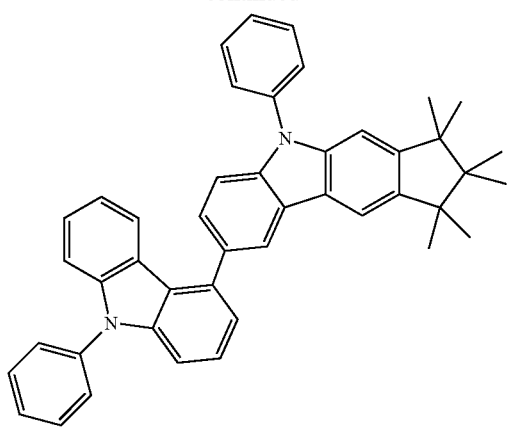
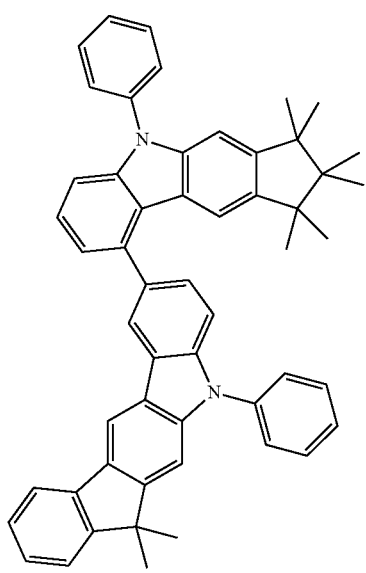
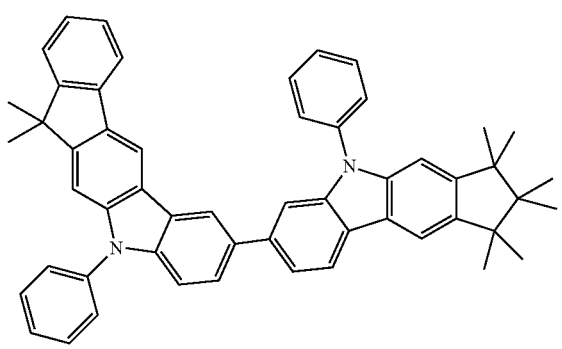
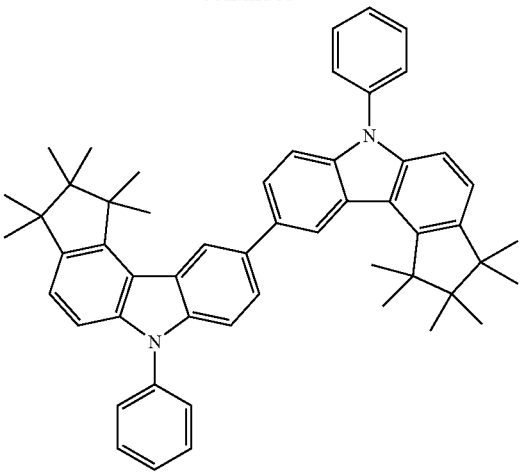
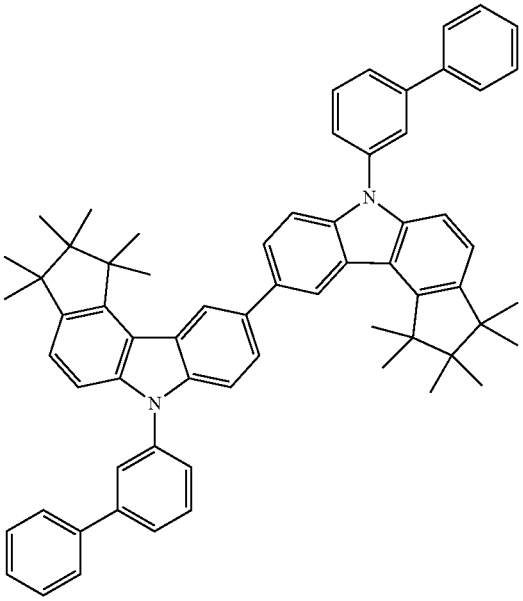
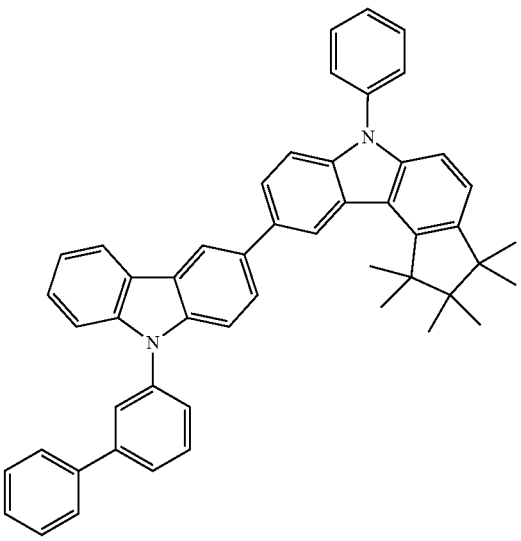

95
-continued
96
-continued
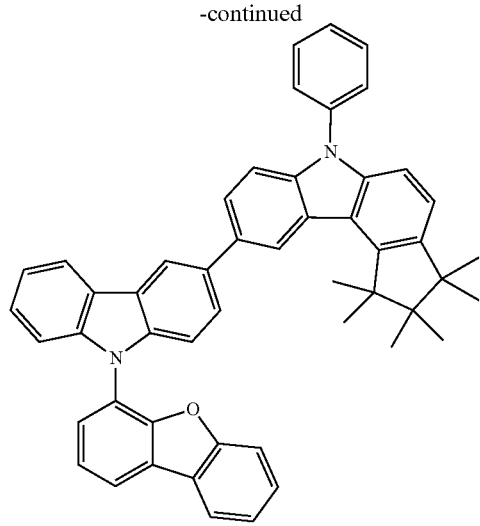
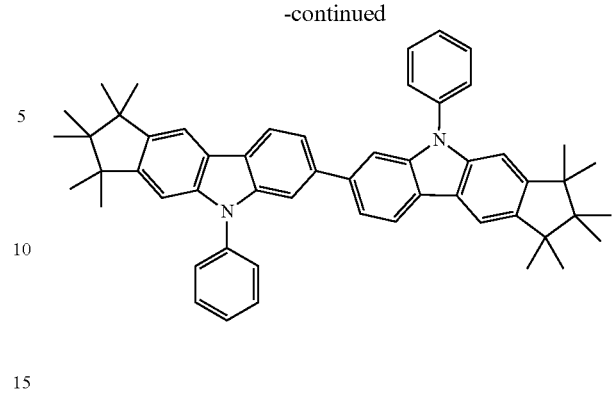
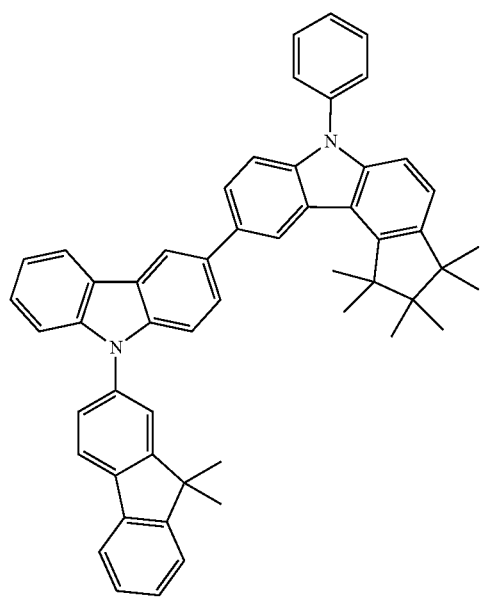
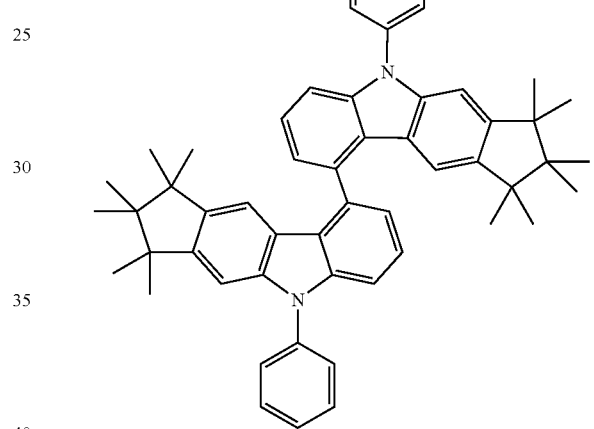
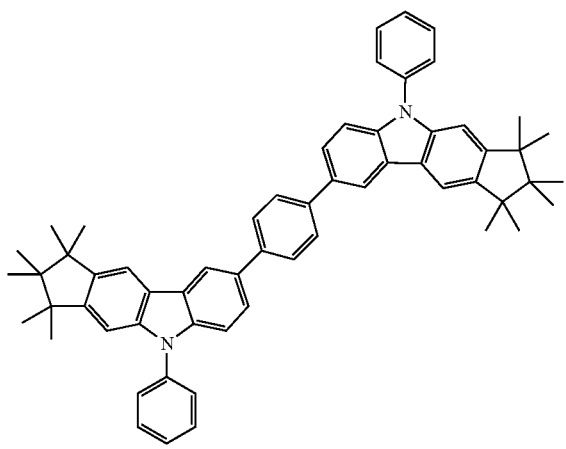
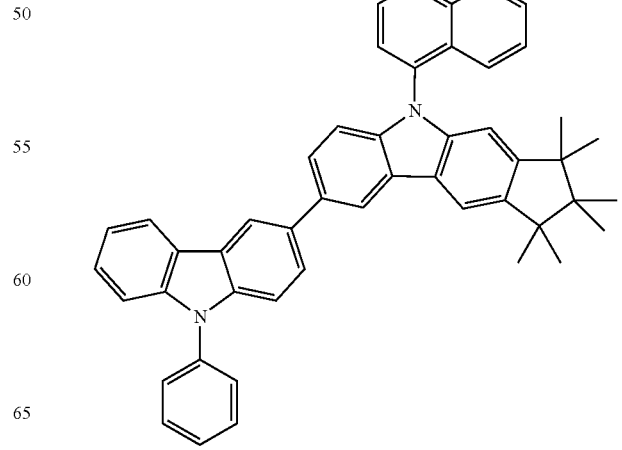

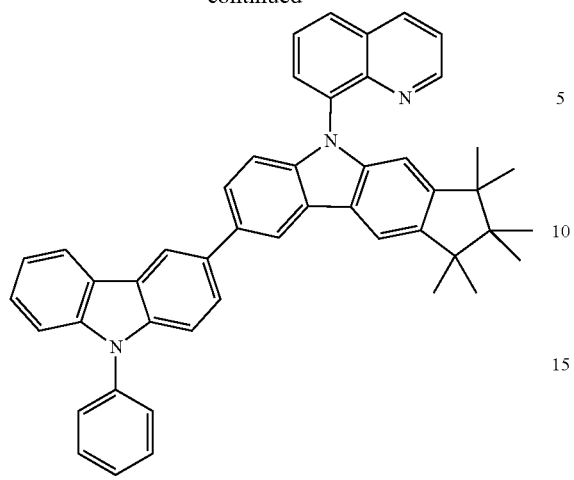
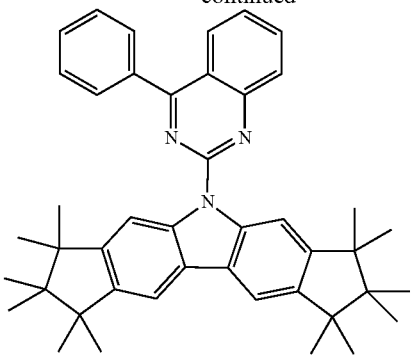
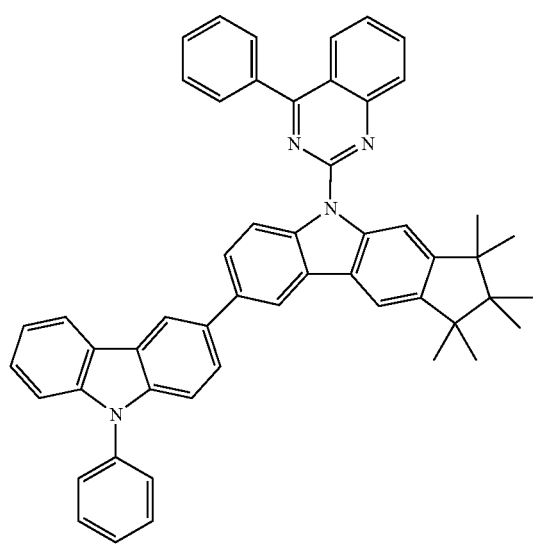
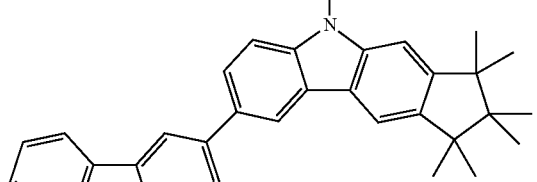
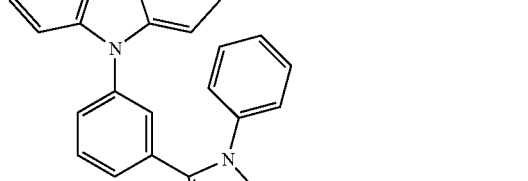
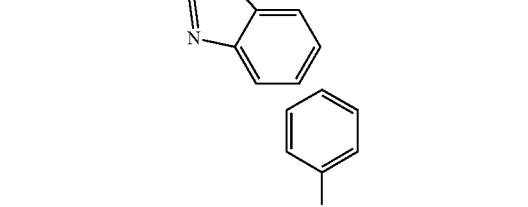
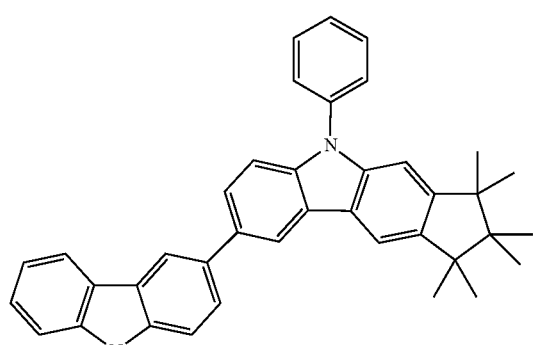

The compounds according to the invention can be prepared by synthesis steps known to the person skilled in the art, such as, for example, bromination, Suzuki coupling, Ullmann coupling, Hartwig-Buchwald coupling, etc. A unit of one of the above-mentioned formulae is preferably introduced onto the indenocarbazole basic structure or the corresponding derivative with O or S in the bridge by a Suzuki coupling, an Ullmann coupling or a Hartwig-Buchwald coupling.

The invention further relates to a process for the preparation of a compound according to the invention, characterized in that the group of the formula (1) is introduced by a Suzuki coupling, an Ullmann coupling, or by a Hartwig-Buchwald coupling.

The present invention further relates to mixtures comprising at least one compound according to the invention and at least one further compound. The further compound can be, for example, a fluorescent or phosphorescent dopant if the compound according to the invention is used as matrix material, in particular a phosphorescent dopant. Suitable dopants are mentioned below in connection with the organic electroluminescent devices and are also preferred for the mixtures according to the invention.

For processing from solution or from the liquid phase, for example by spin coating or by printing processes, solutions or formulations of the compounds or mixtures according to the invention are necessary. It may be preferred to use mixtures of two or more solvents. Suitable and preferred solvents are, for example, toluene, anisole, o-, m- or p-xylene, methylbenzoate, dimethylanisole, mesitylene, tetralin, veratrol, THF, methyl-THF,THP, chlorobenzene, dioxane, phenoxytoluene, especially 3-phenoxytoluene, (−)-fenchone, 1,2,3,5,-tetramethylbenzene, 1,2,4,5,-tetramethylbenzene, 1-methylnaphthaline, 2-methylbenzothiazole, 2-phenoxyethanol, 2-pyrrolidone, 3-methylanisole, 4-methylanisole, 3,4-dimethylanisole, 3,5-dimethylanisole, acetophenone, α-terpineol, benzothiazole, butylbenzoate, cumol, cyclohexanol, cyclohexanone, cyclohexylbenzene, decalin, dodecylbenzene, ethylbenzoate, indane, NMP, p-cymol, ethyl phenyl ether, 1,4-diisopropylbenzene, dibenzyl ether, diethyleneglycol butyl methyl ether, triethyleneglycol dimethyl ether, diethyleneglycol monobutyl ether, tripropyleneglycol dimethyl ether, tetraethyleneglycol dimethyl ether, 2-isopropyl naphthaline, pentylbenzene, hexylbenzene, heptylbenzene, octylbenzene, 1,1-bis(3,40dimethylphenyl)ethane, or mixtures of these solvents.

The present invention therefore furthermore relates to a formulation, in particular a solution, a suspension, or a miniemulsion, comprising at least one compound or mixture according to the invention and one or more solvents, in particular organic solvents. The way in which solutions of this type can be prepared is known to the person skilled in the art and is described, for example, in WO 2002/072714, WO 2003/019694 and the literature cited therein.

The compounds and mixtures according to the invention are suitable for use in an electronic device. An electronic device here is taken to mean a device which comprises at least one layer which comprises at least one organic compound. However, the component here may also comprise inorganic materials or also layers built up entirely from inorganic materials.

The present invention further includes the use of the compounds or mixtures according to the invention in an electronic device, in particular in an organic electroluminescent device. The electronic device comprises at least one of the compounds or mixtures according to the invention mentioned above. The preferences stated above for the compound also apply to the electronic devices.

The electronic device is preferably selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic dye-sensitized solar cells, organic optical detectors, organic photoreceptors, organic field-quench devices (O-FQDs), light-emitting electrochemical cells (LECs), organic laser diodes (O-lasers) and "organic plasmon emitting devices" (D. M. Koller et al., Nature Photonics, 2008, 1-4), preferably organic electroluminescent devices (OLEDs, PLEDs), in particular phosphorescent OLEDs.

The compound according to the present invention can be used in different layers of an electronic device. For example, the compound can be used in emissive layers (EML) as a matrix with fluorescent or phosphorescent emitter, preferably with phosphorescent emitter. In one embodiment, the EML comprises additional matrix material. In another embodiment, the EML comprises further material which is a wide band gap material.

The compound can be included in an electron transport layer (ETL) as an electron transport material (ETM). In one embodiment, the ETL can include additional ETM. The compound can be included in a hole transport layer (HTL) as a hole transport material (HTM). In one embodiment, the HTL can include additional HTM.

In another embodiment, the compound can be used in a hole blocking layer (HBL) as a hole blocking material (HBM). In one embodiment, the HBL can include additional HBM. Moreover, the compound can be used in an electron blocking layer (EBL) as electron blocking material (EBM). In one embodiment, the EBL can include additional EBM.

The organic electroluminescent device comprises a cathode, an anode and at least one emitting layer. Apart from these layers, it may also comprise further layers, for example, in each case one or more hole injection layers, hole transport layers, hole blocking layers, electron-transport layers, electron-injection layers, exciton-blocking layers, electron-blocking layers and/or charge-generation layers. It is likewise possible for interlayers, which have, for example, an exciton-blocking function, to be introduced between two emitting layers. However, it should be pointed out that each of these layers does not necessarily have to be present. The organic electroluminescent device here may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to systems having three emitting layers, where the three layers exhibit blue, green and orange or red emission (for the basic structure see, for example, WO 2005/011013). These can be fluorescent or phosphorescent emission layers or hybrid systems, in which fluorescent and phosphorescent emission layers are combined with one another.

The compound according to the invention in accordance with the embodiments indicated above can be employed in various layers, depending on the precise structure. Preference is given to an organic electroluminescent device comprising a compound of the formula (1) as matrix material for fluorescent or phosphorescent emitters, in particular for phosphorescent emitters, and/or in an electron-transport layer and/or in an electron-blocking or exciton-blocking layer and/or in a hole-transport layer, depending on the precise substitution. The preferred embodiments indicated above also apply to the use of the materials in organic electronic devices.

In a preferred embodiment of the invention, the compound of the formula (1) is employed as matrix material for a fluorescent or phosphorescent compound, in particular for a phosphorescent compound, in an emitting layer. The organic electroluminescent device here may comprise one emitting layer or a plurality of emitting layers, where at least one emitting layer comprises at least one compound according to the invention as matrix material.

If the compound of the formula (1) is employed as matrix material for an emitting compound in an emitting layer, it is preferably employed in combination with one or more phosphorescent materials (triplet emitters). Phosphorescence in the sense of this invention is the luminescence from an excited state having spin multiplicity >1, in particular from an excited triplet state. For the purposes of this application, all luminescent transition-metal complexes and luminescent lanthanide complexes, in particular all iridium, platinum and copper complexes, are to be regarded as phosphorescent compounds.

The mixture comprising the compound of the formula (1) comprises between 99 and 1% by weight, preferably between 98 and 10% by weight, particularly preferably between 97 and 60% by weight, in particular between 95 and 80% by weight, of the compound of the formula (1), based on the entire mixture comprising emitter and matrix material. Correspondingly, the mixture comprises between 1 and 99% by weight, preferably between 2 and 90% by weight, particularly preferably between 3 and 40% by weight, in particular between 5 and 20% by weight, of the emitter, based on the entire mixture comprising emitter and matrix material.

A further preferred embodiment of the present invention is the use of the compound of the formula (1) as matrix material for a phosphorescent emitter in combination with at least one further matrix material. Particularly suitable matrix materials which can be employed in combination with the compound of formula (1) are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, indenocarbazole derivatives, for example in accordance with WO 2010/136109 and WO 2011/000455, azacarbazole derivatives, for example in accordance with EP 1617710, EP 1617711, EP 1731584, JP 2005/347160, bipolar matrix materials, for example in accordance with WO 2007/137725, silanes, for example in accordance with WO 005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, diazasilole or tetraazasilole derivatives, for example in accordance with WO 2010/054729, diazaphosphole derivatives, for example in accordance with WO 2010/054730, bridged carbazole derivatives, for example in accordance with US 2009/0136779, WO 2010/050778, WO 2011/042107, WO 2011/088877 or in accordance with the unpublished application EP 11003232.3, triphenylene derivatives, for example in accordance with WO 2012/048781, or lactams, for example in accordance with WO 2011/116865 or WO 2011/137951.

A further phosphorescent emitter which emits at shorter wavelength than the actual emitter may likewise be present in the mixture as co-host.

Suitable phosphorescent compounds (=triplet emitters) are, in particular, compounds which emit light, preferably in the visible region, on suitable excitation and in addition contain at least one atom having an atomic number greater than 20, preferably greater than 38, and less than 84, particularly preferably greater than 56 and less than 80, in particular a metal having this atomic number. The phosphorescent emitters used are preferably compounds which contain copper, molybdenum, tungsten, rhenium, ruthenium, osmium, rhodium, iridium, palladium, platinum, silver, gold or europium, in particular compounds which contain iridium or platinum. For the purposes of the present invention, all luminescent compounds which contain the above-mentioned metals are regarded as phosphorescent compounds.

Examples of the emitters described above are revealed by the applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898, WO 2011/157339, or WO 2012/007086. In general, all phosphorescent complexes as used in accordance with the prior art for phosphorescent OLEDs and as are known to the person skilled in the art in the area of organic electroluminescence are suitable, and the person skilled in the art will be able to use further phosphorescent complexes without inventive step.

In a further embodiment of the invention, the organic electroluminescent device according to the invention does not comprise a separate hole-injection layer and/or hole transport layer and/or hole blocking layer and/or electron transport layer, i.e. the emitting layer is directly adjacent to the hole injection layer or the anode, and/or the emitting layer is directly adjacent to the electron transport layer or the electron injection layer or the cathode, as described, for example, in WO 2005/053051. It is furthermore possible to use a metal complex which is identical or similar to the metal complex in the emitting layer as hole transport or hole injection material directly adjacent to the emitting layer, as described, for example, in WO 2009/030981.

It is furthermore possible to employ the compounds according to the invention as a functional material selected from a hole injection material (HIM), hole transport material (HTM), hole blocking material (HBM), electron injection material (EIM), electron transport material (ETM), electron blocking material (EBM), host material, matrix material, wide band gap material, fluorescent emitter, phosphorescent emitter, n-dopant and p-dopant.

The functional materials are preferably organic materials. In one embodiment, n-dopant and p-dopant can be both inorganic and organic, preferably organic. In another embodiment, the wide band gap material is a material as described, for example, in U.S. Pat. No. 7,294,849. These systems show advantageous performance data in electroluminescent device.

Preferably the band gap material is defined by its band gap which should be larger than 3.5 eV, very preferably larger than 3.7 eV and particularly preferably larger than 3.9 eV.

Band gap, as used herein, is defined by the distance between the HOMO (highest occupied molecular orbital) and LUMO (lowest unoccupied molecular orbital) energy level. As both HOMO and LUMO level strongly depend on the method used for determination. The use of different techniques for the determination of HOMO and LUMO energies will also lead to different band gaps. The use of a specific technique is crucial in order to determine if a compound is a wide band gap material.

The energy values indicated relate to isolated compounds here and are determined as described below.

The HOMO and LUMO energies and the triplet level of the materials are determined via quantum-chemical calculations. To this end, the "Gaussian09, Revision D.01" software package (Gaussian Inc.) is used here. However, other software packages can also be used so long as the same methods have been implemented therein. In order to calculate organic substances without metals, firstly a geometry optimisation is carried out using the semi-empirical method AM1 (Gaussian input line "# AM1 opt") with charge 0 and multiplicity 1. An energy calculation (single point) for the electronic ground state and triplet level is subsequently carried out on the basis of the optimised geometry. The TDDFT (time dependent density functional theory) method B3PW91 with the 6-31G(d) base set (Gaussian input line "# B3PW91/6-31G(d) td=(50-50,nstates=4)") is used here (charge 0, multiplicity 1). For organo-metallic compounds, the geometry is optimised using the Hartree-Fock method and the LanL2 MB base set (Gaussian input line "# HF/LanL2 MB opt") (charge 0, multiplicity 1). The energy calculation is carried out analogously to the organic substances, as described above, with the difference that the "LanL2DZ" base set is used for the metal atom and the "6-31G(d)" base set is used for the ligands (Gaussian input line "# B3PW91/gen pseudo=lanl2 td=(50-50,nstates=4)"). The energy calculation gives the HOMO as the final orbital occupied by two electrons (Alpha occ. eigenvalues) and the LUMO as the first unoccupied orbital (Alpha virt. eigenvalues) in hartree units (HEh or LEh). The HOMO and LUMO value in electron volts calibrated with reference to cyclic voltammetry measurements is determined therefrom as follows:

LUMO (eV)=(1.0658*$LEh$*27.212)−0.5049

HOMO (eV)=(0.8308*$HEh$*27.212)−1.1180

These values are to be regarded as HOMO or LUMO of the materials for the purposes of this application.

The triplet level T1 of a material is defined as the relative excitation energy (in eV) of the triplet state having the lowest energy which arises from the quantum-chemical energy calculation.

The above-mentioned conditions and the method for determining the individual energy values allow the person skilled in the art to identify the suitable wide band gap materials from the prior art in a simple manner. The calculation of orbital energies represents a routine activity for the person skilled in the art, which he can carry out in a short time with the aid of the above-mentioned method.

In the remaining layers of the organic electroluminescent device according to the invention, it is possible to use all materials as usually employed in accordance with the prior art. The person skilled in the art can prepare and manufacture, without inventive step, all materials known for organic electroluminescent devices in combination with the compounds of the formula (1) according to the invention or in accordance with the preferred embodiments.

Preference is furthermore given to an organic electroluminescent device, characterized in that one or more layers are applied by means of a sublimation process, in which the materials are vapor-deposited in vacuum sublimation units at an initial pressure of less than $10^{-5}$ mbar, preferably less than $10^{-6}$ mbar. However, it is also possible for the initial pressure to be even lower or higher, for example less than $10^{-7}$ mbar.

Preference is likewise given to an organic electroluminescent device, characterized in that one or more layers are applied by means of the OVPD (organic vapour phase deposition) process or with the aid of carrier gas sublimation, in which the materials are applied at a pressure between $10^5$ mbar and 1 bar. A special case of this process is the OVJP (organic vapour jet printing) process, in which the materials are applied directly through a nozzle and thus structured (for example M. S. Arnold et al., Appl. Phys. Lett. 2008, 92, 053301).

Preference is furthermore given to an organic electroluminescent device, characterized in that one or more layers are produced from solution, such as, for example, by spin coating, or by means of any desired printing process, such as, for example, ink-jet printing, LITI (light induced thermal imaging, thermal transfer printing), screen printing, flexographic printing, offset printing or nozzle printing. Soluble compounds, which are obtained, for example, by suitable substitution, are necessary for this purpose. These processes are also particularly suitable for oligomers, dendrimers and Polymers.

Also possible are hybrid processes, in which, for example, one or more layers are applied from solution and one or more further layers are applied by vapor deposition. Thus, it is possible, for example, to apply the emitting layer from solution and to apply the electron-transport layer by vapor deposition.

These processes are generally known to the person skilled in the art and can be applied by him without inventive step to organic electroluminescent devices comprising the compounds according to the invention.

The compounds according to the invention have one or more of the following surprising advantages over the prior art on use in organic electroluminescent devices:

1. The power efficiency of corresponding devices becomes higher compared to systems in accordance with the prior art.
2. The stability of corresponding devices becomes higher compared to systems in accordance with the prior art, which is evident, in particular, from a significantly longer lifetime.
3. The organic electroluminescent devices according to the invention have a reduced operating voltage.
4. If the compounds according to the invention are used as matrix materials for phosphorent emitters, it is possible to achieve very good results with only a low emitter concentration in the region of less than 10% by vol.
5. The compounds according to the invention have very good thermal stability.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features. All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

It will be appreciated that many of the features described above, particularly of the preferred embodiments, are inventive in their own right and not just as part of an embodiment of the present invention. Independent protection may be sought for these features in addition to or alternative to any invention presently claimed.

The teaching as disclosed here can be abstracted and combined with other examples disclosed.

Other features of the invention will become apparent in the course of the following description of exemplary embodiments and drawings, which are given for illustration of the invention and are not intended to be limiting thereof.

The invention is now illustrated in greater detail by the following examples, without wishing to restrict it thereby.

WORKING EXAMPLES

Example 1

Synthesis of 1,1,2,2,3,3-Hexamethyl-1,2,3,9-tetrahydro-9-aza-cyclopenta[b]fluorene (4a) and 1,1,2,2,3,3-Hexamethyl-1,2,3,6-tetrahydro-cyclopenta[c]carbazole (5a)

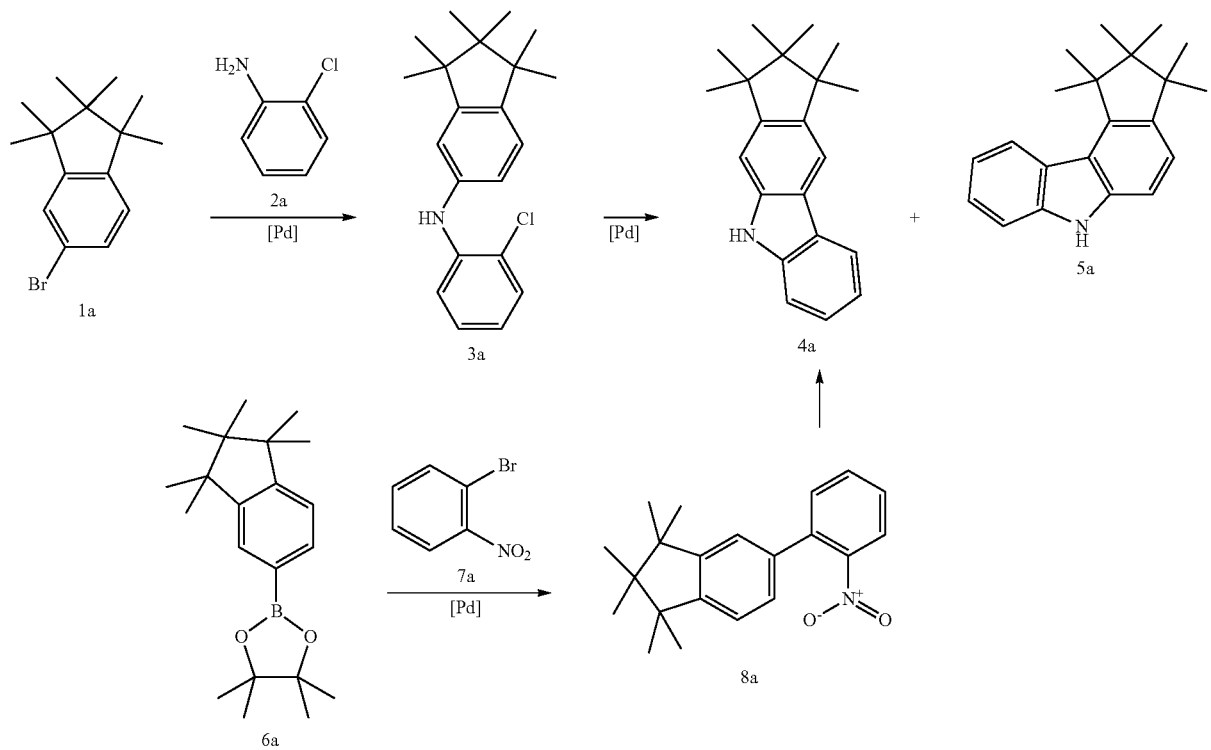

Synthesis of (2-Chloro-phenyl)-(1,1,2,2,3,3-hexamethyl-indan-5-yl)-amine (3a)

In a 2 L four-necked flask 51.5 g (183 mmol, 1.0 eq) of 5-bromo-2,3-dihydro-1,1,2,2,3,3-hexamethyl-1H-Indene [1562418-80-7] are dissolved together with 25.0 g (196 mmol, 1.07 eq) 2-chloroanilin and 45.7 g (476 mmol, 2.6 eq) sodium-tert-butoxide in 840 ml of dried toluene. The mixture was degassed for 30 minutes and then, 411 mg (1.83 mmol, 0.01 eq) of palladium(II)-acetate and 1.01 g (1.83 mmol, 0.01 eq) 1,1'-bis(diphenylphosphino)ferrocene are added. The reaction is heated to 100° C. for 4 hours. After the reaction is finished, 300 ml water are added and the mixture is stirred for additional 30 minutes. Then, the aqueous phase is separated and the organic phase is washed 3 times with water. The combined aqueous layers are extracted once with toluene. The combined organic layers are dried over sodium sulfate and the solvent is removed in vacuo. 54.0 g (164 mmol, 90%) of desired secondary amine 3a is obtained as brownish oil.

Synthesis of 1,1,2,2,3,3-Hexamethyl-1,2,3,9-tetrahydro-9-aza-cyclopenta[b]fluorene (4a) and 1,1,2,2,3,3-Hexamethyl-1,2,3,6-tetrahydro-cyclopenta[c]carbazole (5a)

A 1 L four-necked flask is charged with 54.0 g (164 mmol, 1.0 eq) of (2-Chloro-phenyl)-(1,1,2,2,3,3-hexamethyl-indan-5-yl)-amine 3a, 56.7 g (410 mmol, 2.5 eq) potassium carbonate and 650 ml of 1-methyl-2-pyrrolidon. After the mixture is degassed for 30 minutes, 5.03 g (49.2 mmol, 0.30 eq) pivalic acid, 736 mg (3.3 mmol, 0.02 eq) palladium(II)-acetate and 6.6 ml (6.6 mmol, 0.04 eq) of a 1 mol/l tri-tert.-butylphoshine solution in toluene is added. The reaction is stirred overnight at 130° C. and after the reaction is finished, the solvent and the pivalic acid are removed in vacuo and the remaining solid is dissolved in 100 ml toluene. The solution is washed 3 times with 150 ml water and dried over sodium sulfate. After evaporation of the solvent, the isomeric mixture is separated by two-fold crystallization from n-heptane. 13.4 g (45.9 mmol, 28%) of isomer 4a are obtained as light-brown crystals and 29.1 g (100 mmol, 61%) of isomer 5a are obtained after evaporation of the solvent.

Synthesis of 1,1,2,2,3,3-Hexamethyl-5-(2-nitro-phenyl)-indan (8a)

50.0 g (152 mmol, 1.0 eq) 2-(1,1,2,2,3,3-Hexamethyl-indan-5-yl)-4,4,5,5-tetramethyl-[1,3,2]dioxaboro-lane and 32.3 g (160 mmol, 1.05 eq) 1-bromo-2-nitrobenze are dissolved together with 32.3 g (305 mmol, 2.0 eq) sodium carbonate in 400 ml toluene, 400 ml 1,4-dioxane and 200 ml water. After degassing for 30 minutes, 1.76 g (1.52 mmol, 0.01 eq) tetrakis(triphenyl-phosphin)palladium(0) are added and the mixture is stirred overnight at reflux. Then, the phases are separated and the aqueous phase is extracted once with toluene. The combined organic layers are washed with sat. NaCl solution and dried over sodium sulfate. After crystallization from n-heptane, 28.0 g (86 mmol, 57%) 8a are obtained as slight brown crystals. The remaining solution is evaporated until more product precipitated and 18.6 g (57 mmol, 38%) of additional product 8a are obtained.

Synthesis of 1,1,2,2,3,3-Hexamethyl-1,2,3,9-tetrahydro-9-aza-cyclopenta[b]fluorene (4a) and 1,1,2,2,3,3-Hexamethyl-1,2,3,6-tetrahydro-cyclopenta[c]carbazole (5b)

40.5 g (124 mmol, 1.0 eq) 8a are reacted with 417 mg (2.5 mmol, 0.02 eq) palladium(II)-acetate and 2.40 g (13 mmol, 0.11 eq) 1,10-phenanthrolin in 500 ml DMF in the presence of 2.8 l carbon monoxide in an autoclave (140° C., max. 7.6 bar, 35 h). After the reaction is finished, the mixture is filtered with 95:5 heptane/THF over silica and the solvents are evaporated in vacuo. The isomeric mixture is separated by crystallization. 14.3 g (49 mmool, 40%) of isomer 4a are obtained after two crystallizations as light-brownish crystals, whereas 19.7 g (67 mmol, 55%) of isomer 5a are obtained after evaporation of the solvent.

Example 2

Synthesis of 6-Bromo-1,1,2,2,3,3-hexamethyl-1,2,3,9-tetrahydro-9-aza-cyclopenta[b]fluorene (9a)

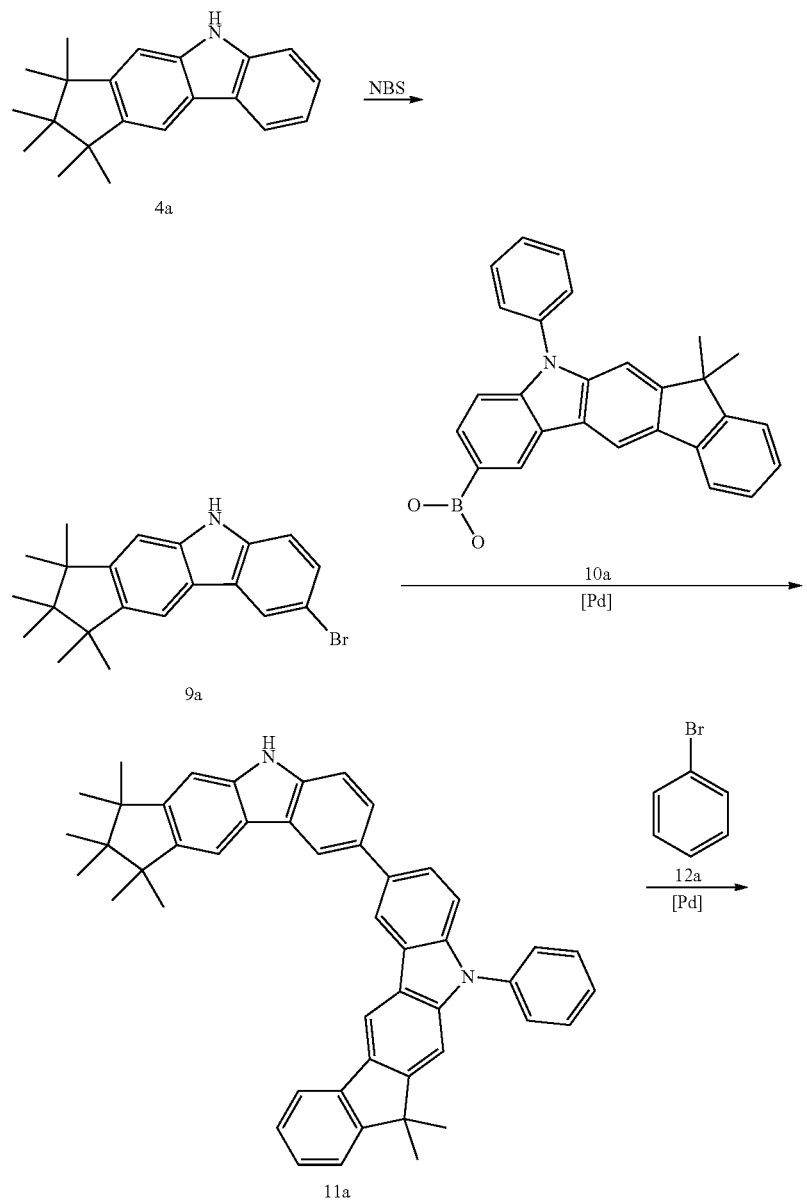

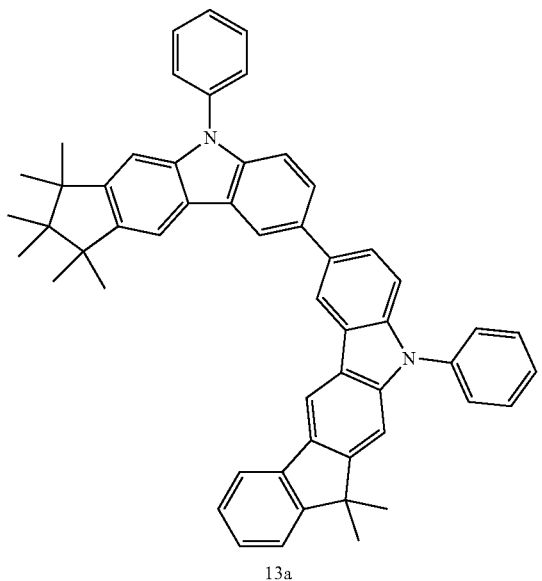

13a 15.1 g (51.8 mmol, 1.0 eq) carbazole 4a is dissolved in 400 ml THF and cooled in an ethanol/ice bath. Then, 9.51 g (53.4 g, 1.03 eq) N-bromsuccinimide are added subsequently at 0-5° C. After stirring for one hour at this temperature the reaction is stirred overnight at room temperature. The mixture is concentrated to about 50 ml and 100 ml water are added. The precipitate is filtered and washed with water. 18.9 g (51.0 mmol, 99%) of a slightly brown solid are obtained.

Analogously the following compound can be obtained:

| Compound | Educt | Product | Yield [%] |
|---|---|---|---|
| 9b | 5a | 9b | 43 |

Example 3

Synthesis of 7-(1,1,2,2,3,3-Hexamethyl-1,2,3,9-tetrahydro-9-aza-cyclopenta[b]fluoren-6-yl)-12,12-dimethyl-10-phenyl-10,12-dihydro-10-aza-indeno[2,1-b]fluorene (11a)

13.0 g (35.1 mmol, 1.0 eq) of 6-Bromo-1,1,2,2,3,3-hexamethyl-1,2,3,9-tetrahydro-9-aza-cyclopenta[b]fluorene 9a, 17.5 g (36.2 mmol, 1.03 eq) 12,12-Dimethyl-10-phenyl-7-(4,4,5,5-tetramethyl-[1,3,2]dioxaborolan-2-yl)-10,12-dihydro-10-aza-indeno[2,1-b]fluorine [1379585-25-7] 10a and 18.6 g (70.2 mmol, 2.0 eq) potassium phosphate are dissolved in 200 ml toluene, 200 ml 1,4-dioxane and 100 ml water. After the mixture is degassed for 30 minutes, 79 mg (0.35 mmol, 0.01 eq) palladium(II)-acetate and 427 mg (1.40 mmol, 0.04 eq) tri(o-tolyl)-phosphine are added. The reaction is stirred at reflux overnight and warmed to room temperature. The mixture is filtered over Celite and diluted with 400 ml toluene. The aqueous layer is separated, the organic phase washed three times with NaCl solution and the combined organic phases dried over sodium sulfate. After evaporation of the solvent, the residue is stirred for 30 minutes in 200 ml n-heptane at 60° C. After filtration 21.3 g (32.8 mmol, 93%) of product 11a are obtained as grey-brown solid.

Analogously the following compounds can be obtained:

| Comp. | Educt | Educt | Product | Yield [%] |
|---|---|---|---|---|
| 11b | | [854952-58-2] | | 89 |
| 11c | | [1379585-25-7] | | 92 |
| 11d | | [1133058-06-6] | | 74 |
| 11e | | [1372179-42-4] | | 82 |

-continued
| Comp. | Educt | Educt | Product | Yield [%] |
|---|---|---|---|---|
| 11f | 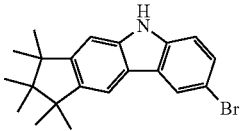 [SMILES: CC1(C)c2cc3[nH]c4ccc(Br)cc4c3cc2C(C)(C)C1(C)C] | 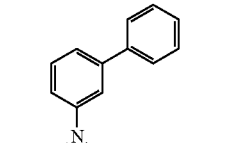 [1416814-68-0] | 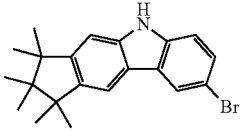 [SMILES: CC1(C)c2cc3[nH]c4ccc(Br)cc4c3cc2C(C)(C)C1(C)C] | 91 |
| 11g | 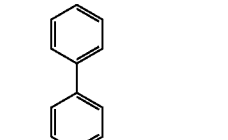 | 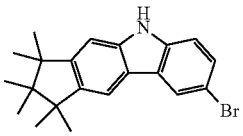 [SMILES: CC1(C)c2cc3[nH]c4ccc(Br)cc4c3cc2C(C)(C)C1(C)C] [1028648-22-7] | 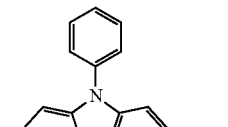 | 82 |
| 11h | | [1133058-05-5] | | 96 |

-continued

| Comp. | Educt | Educt | Product | Yield [%] |
|---|---|---|---|---|
| 11i | | [1373359-70-6] | | 84 |
| 11j | | [1459705-44-2] | | 55 |
| 11k | | [1316311-17-7] | | 78 |

-continued
| Comp. | Educt | Educt | Product | Yield [%] |
|---|---|---|---|---|
| 11l | 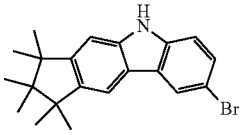 [SMILES: CC1(C)c2cc3[nH]c4ccc(Br)cc4c3cc2C(C)(C)C1(C)C] | 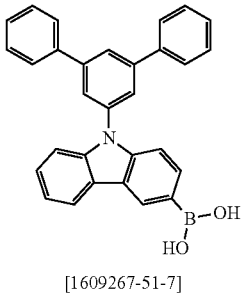 [SMILES: OB(O)c1ccc2c(c1)c1ccccc1n2-c1cc(-c2ccccc2)cc(-c2ccccc2)c1] [1609267-51-7] | 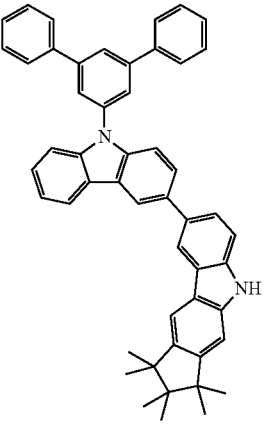 [SMILES: CC1(C)c2cc3[nH]c4ccc(-c5ccc6c(c5)c5ccccc5n6-c5cc(-c6ccccc6)cc(-c6ccccc6)c5)cc4c3cc2C(C)(C)C1(C)C] | 96 |
| 11m | 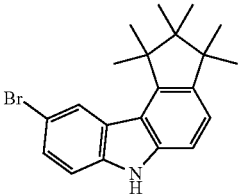 [SMILES: CC1(C)c2ccc3[nH]c4ccc(Br)cc4c3c2C(C)(C)C1(C)C] | 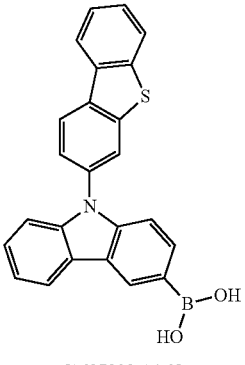 [1637323-14-8] | 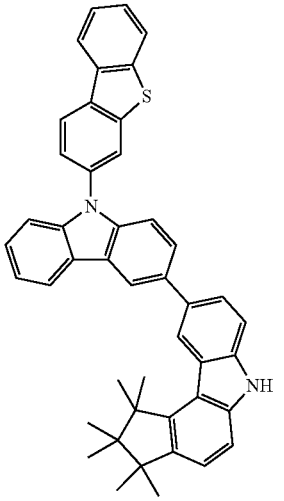 [SMILES: CC1(C)c2ccc3[nH]c4ccc(-c5ccc6c(c5)c5ccccc5n6-c5ccc6c(c5)sc5ccccc56)cc4c3c2C(C)(C)C1(C)C] | 86 |
| 11n | 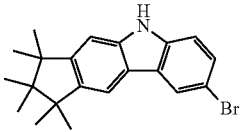 [SMILES: CC1(C)c2cc3[nH]c4ccc(Br)cc4c3cc2C(C)(C)C1(C)C] | 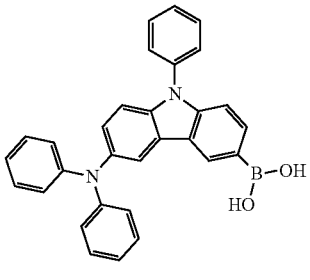 [1316311-20-2] | 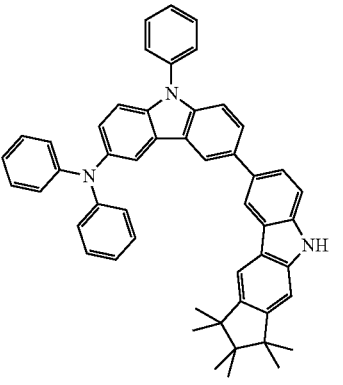 [SMILES: CC1(C)c2cc3[nH]c4ccc(-c5ccc6c(c5)c5cc(N(c7ccccc7)c7ccccc7)ccc5n6-c5ccccc5)cc4c3cc2C(C)(C)C1(C)C] | 71 |

-continued

| Comp. | Educt | Educt | Product | Yield [%] |
|---|---|---|---|---|
| 11o | | [1316311-24-6] | | 32 |
| 11p | | [1622183-74-7] | | 56 |
| 11q | | [1240963-83-0] | | 79 |

-continued

| Comp. | Educt | Educt | Product | Yield [%] |
|---|---|---|---|---|
| 11r | | [1557122-53-8] | | 87 |
| 11s | | [1537218-70-4] | | 72 |
| 11t | | [1613325-86-2] | | 83 |

-continued

| Comp. | Educt | Educt | Product | Yield [%] |
|---|---|---|---|---|
| 11u | | [1572537-61-1] | | 84 |
| 11v | | [1446010-37-2] | | 46 |
| 11w | | [1622875-90-4] | | 88 |

-continued

| Comp. | Educt | Educt | Product | Yield [%] |
|---|---|---|---|---|
| 11x | | [1622875-88-0] | | 86 |
| 11y | | [1679386-11-8] | | 63 |
| 11z | | [1609267-59-5] | | 51 |

-continued

| Comp. | Educt | Educt | Product | Yield [%] |
|---|---|---|---|---|
| 11aa | | [1246562-39-9] | | 68 |
| 11ab | | [1609267-29-9] | | 94 |
| 11ac | | [236389-21-2] | | 69 |
| 11ad | | [1421789-05-5] | | 95 |

-continued

| Comp. | Educt | Educt | Product | Yield [%] |
|---|---|---|---|---|
| 11ae | | [400607-31-0] | | 76 |
| 11af | | [395087-89-5] | | 82 |
| 11ag | | [796071-96-0] | | 87 |
| 11ah | | [1612243-82-9] | | 91 |

| Comp. | Educt | Educt | Product | Yield [%] |
|---|---|---|---|---|
| 11ai | | [1233200-59-0] | | 94 |
| 11aj | | [5122-95-2] | | 85 |
| 11ak | | [98-80-6] | | 83 |
| 11al | | [4612-28-6] | | 76 |

Example 4

Synthesis of 7-(1,1,2,2,3,3-Hexamethyl-9-phenyl-1,2,3,9-tetrahydro-9-aza-cyclopenta[b]fluoren-6-yl)-12,12-dimethyl-10-phenyl-10,12-dihydro-10-aza-indeno[2,1-b]fluorene (13a)

20.0 g (30.8 mmol, 1.0 eq) 7-(1,1,2,2,3,3-Hexamethyl-1,2,3,9-tetrahydro-9-aza-cyclopenta[b]fluoren-6-yl)-12,12-dimethyl-10-phenyl-10,12-dihydro-10-aza-indeno[2,1-b]fluorene 11a, 3.57 ml (33.9 mmol, 1.10 eq) bromobenzene and 8.88 g (92.5 mmol, 3.0 eq) sodium-tert-butoxide are dissolved in 500 ml dry toluene. After degassing for 30 minutes, 138 mg (0.616 mmol, 0.02 eq) palladium(II)-acetate and 1.23 ml (1.23 mmol, 0.04 eq) of a tri-tert-butylphosphine solution (1 mol/l in toluene) are added. The reaction is stirred for two days at reflux, cooled to room temperature and filtered over Celite.

The filtrate is concentrated to about 50 ml and 500 ml heptane are added. The mixture is stirred for one hour and the precipitate filtered and dried. 18.6 g (25.7 mmol, 83%) of a grey solid are obtained as crude product. The product is purified by hot extraction with heptane/toluene 5:1 and three times recrystallized with toluene/acetonitrile. After two sublimations 2.45 g (3.38 mmol, 11%) of final product 13a are obtained as a colorless solid in a purity >99.9% (HPLC).

Analogously the following compounds can be obtained:

| Comp. | Educt | Educt | Product | Yield [%] |
|---|---|---|---|---|
| 13b |  |  | 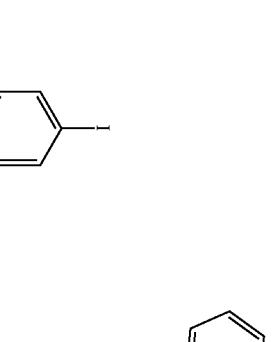 | 43 |
| 13c | 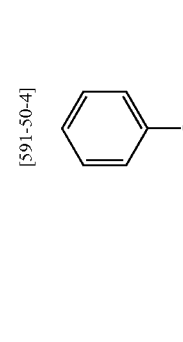 | [591-50-4] | | 56 |

| Comp. | Educt | Educt | Product | Yield [%] |
|---|---|---|---|---|
| 13d | 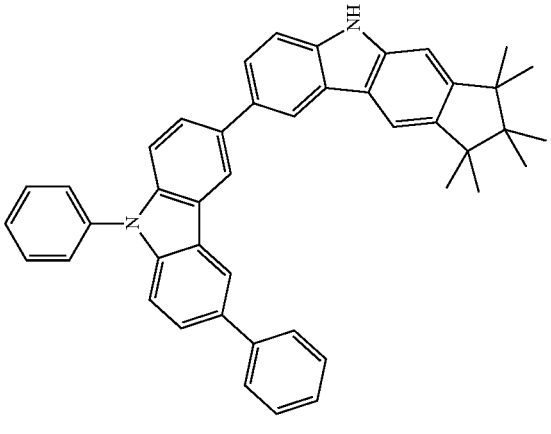 [92-66-0] | 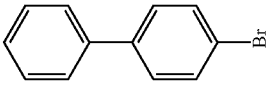 [591-50-4] | 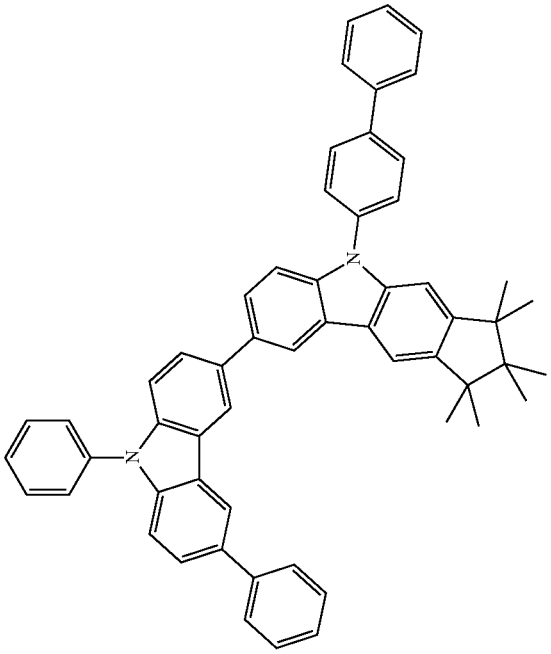 | 23 |

| Comp. | Educt | Educt | Product | Yield [%] |
|---|---|---|---|---|
| 13e | 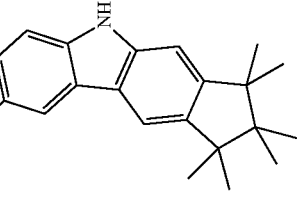 | 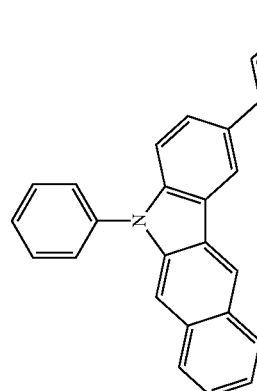 | 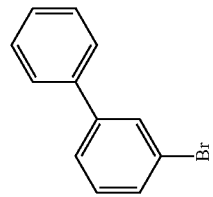 [2113-57-7] | 44 |

| Comp. | Educt | Educt | Product | Yield [%] |
|---|---|---|---|---|
| 13f | | | | 38 |

[2113-57-7]

| Comp. | Educt | Educt | Product | Yield [%] |
|---|---|---|---|---|
| 13g | 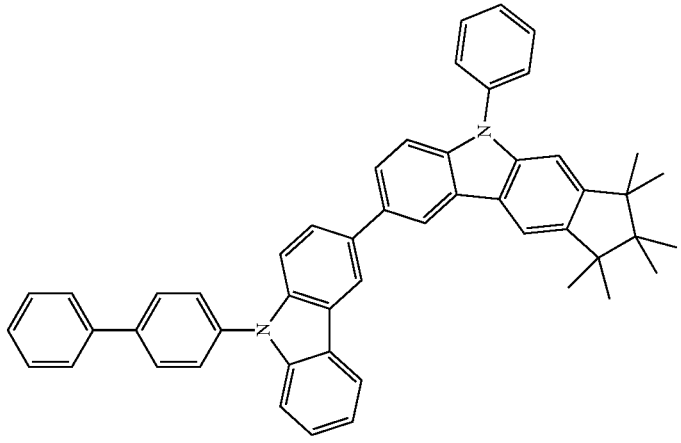 | 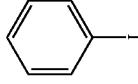  [591-50-4] | | 59 |

| Comp. | Educt | Educt | Product | Yield [%] |
|---|---|---|---|---|
| 13h | | [591-50-4] | | 21 |

| Comp. | Educt | Educt | Product | Yield [%] |
|---|---|---|---|---|
| 13i | 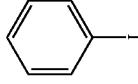 | 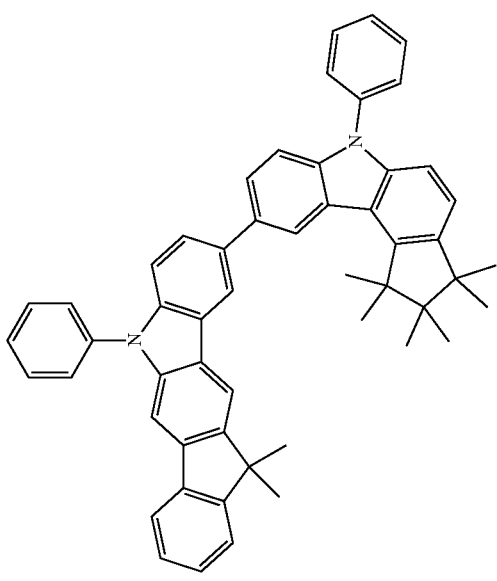  [591-50-4] | 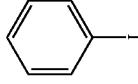 | 17 |

| Comp. | Educt | Educt | Product | Yield [%] |
|---|---|---|---|---|
| 13j | 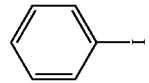 | [591-50-4] | 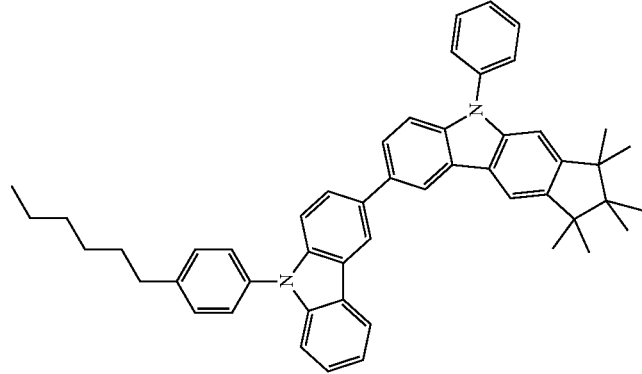 | 45 |

| Comp. | Educt | Educt | Product | Yield [%] |
|---|---|---|---|---|
| 13k | 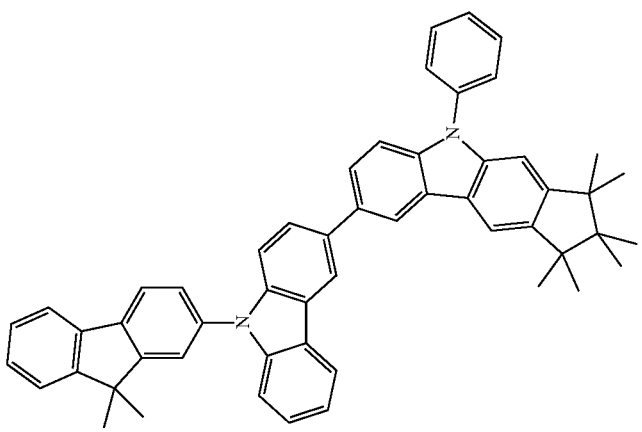 | 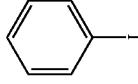   [591-50-4] | | 19 |

| Comp. | Educt | Educt | Product | Yield [%] |
|---|---|---|---|---|
| 131 | 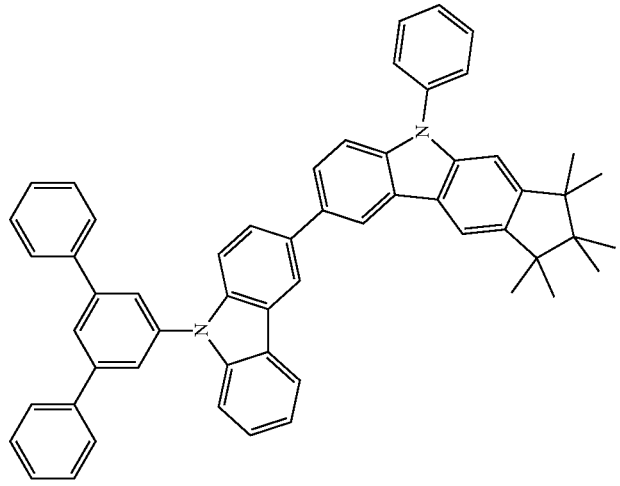 | 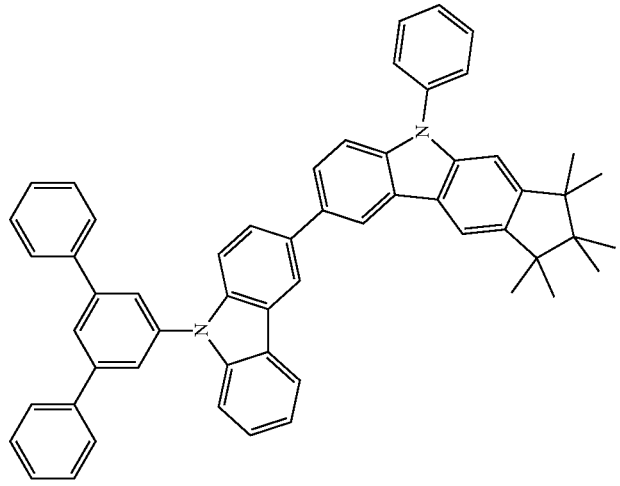  [591-50-4] | 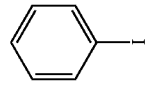 | 54 |

| Comp. | Educt | Educt | Product | Yield [%] |
|---|---|---|---|---|
| 13m | (structure) | (phenyl iodide) [591-50-4] | (structure) | 61 |

| Comp. | Educt | Educt | Product | Yield [%] |
|---|---|---|---|---|
| 13n | 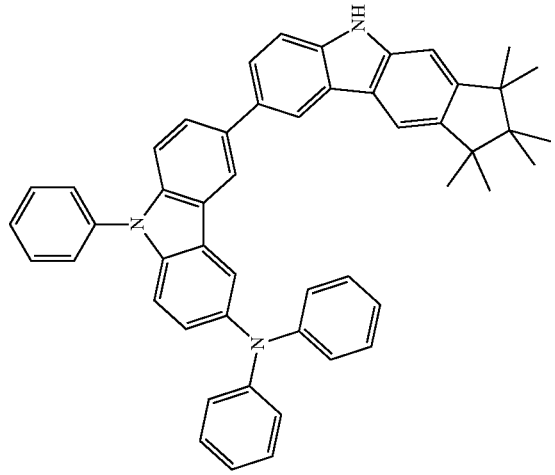 | 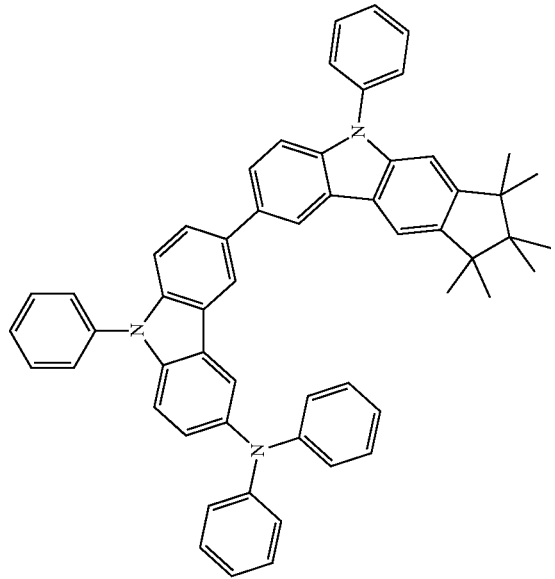[591-50-4] | | 15 |

| Comp. | Educt | Educt | Product | Yield [%] |
|---|---|---|---|---|
| 13o | | [591-50-4] | | 24 |

| Comp. | Educt | Educt | Product | Yield [%] |
|---|---|---|---|---|
| 13p | (structure) | (phenyl iodide) [591-50-4] | (structure) | 33 |

| Comp. | Educt | Educt | Product | Yield [%] |
|---|---|---|---|---|
| 13q | (carbazole-phenyl-carbazole-indenocarbazole-NH structure) | iodobenzene [591-50-4] | (carbazole-phenyl-carbazole-indenocarbazole-N-phenyl product) | 38 |

| Comp. | Educt | Educt | Product | Yield [%] |
|---|---|---|---|---|
| 13r | 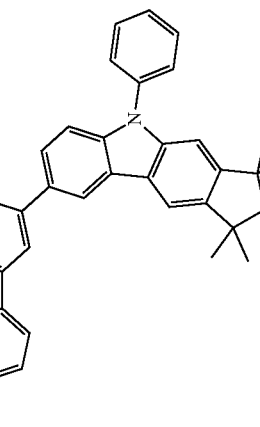 | 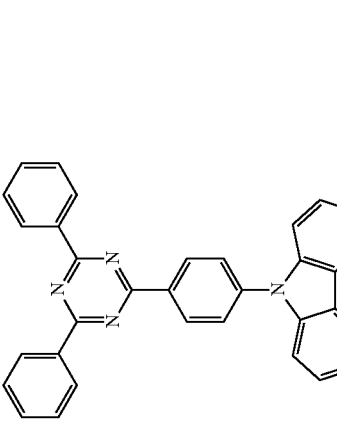 [591-50-4] | | 41 |

| Comp. | Educt | Educt | Product | Yield [%] |
|---|---|---|---|---|
| 13s |  | 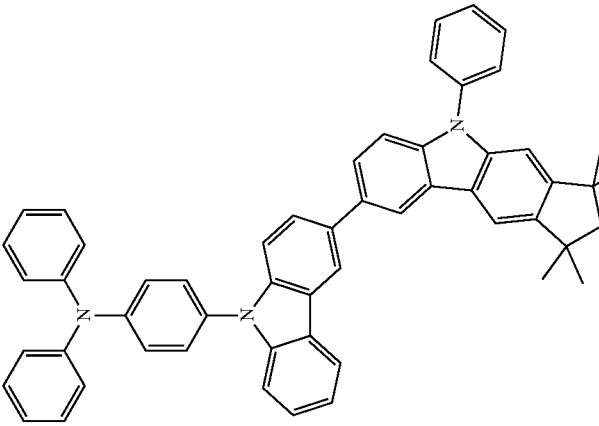  [591-50-4] | | 21 |

| Comp. | Educt | Educt | Product | Yield [%] |
|---|---|---|---|---|
| 13t | (carbazole-dibenzofuran-cyclopenta-fused carbazole educt) | phenyl iodide [591-50-4] | (N-phenylated product) | 18 |

| Comp. | Educt | Educt | Product | Yield [%] |
|---|---|---|---|---|
| 13u | 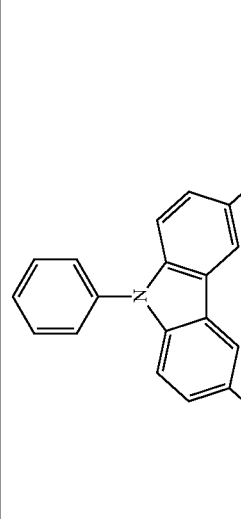 | 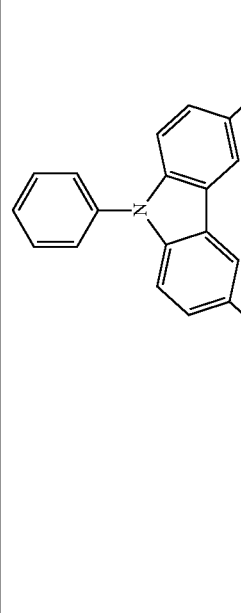 [591-50-4] | | 53 |

| Comp. | Educt | Educt | Product | Yield [%] |
|---|---|---|---|---|
| 13v | 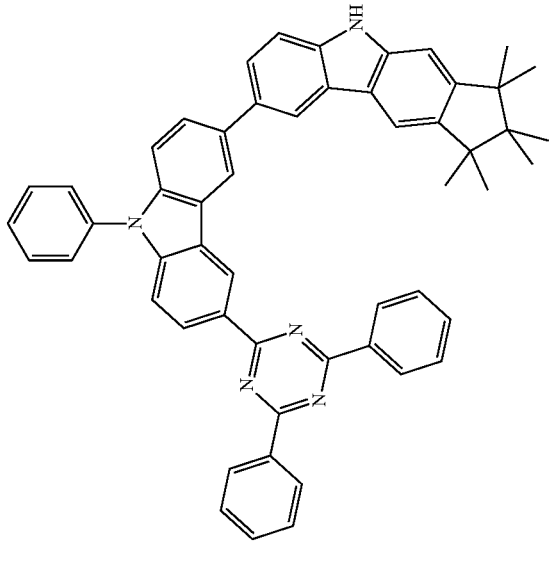 [591-50-4] |  | 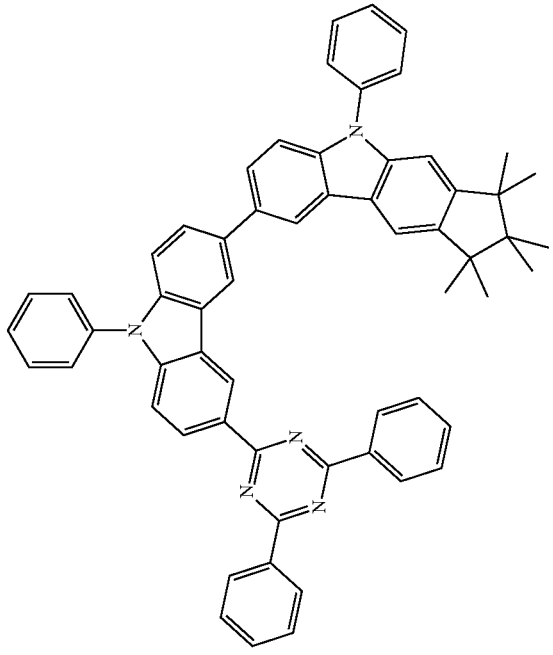 | 27 |

-continued
| Comp. | Educt | Educt | Product | Yield [%] |
|---|---|---|---|---|
| 13w | 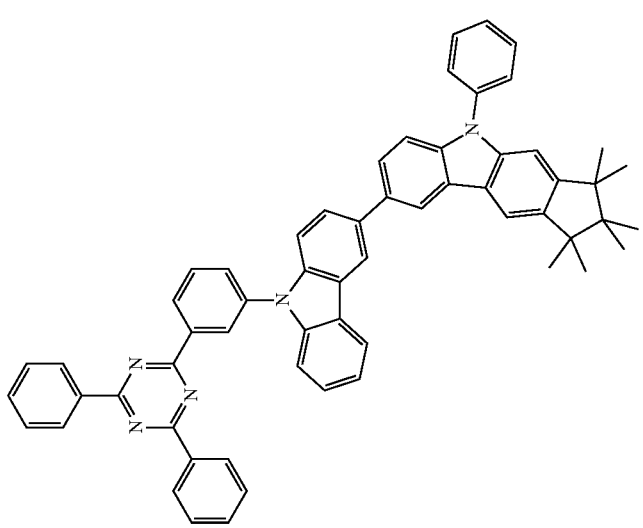 | 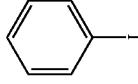 [591-50-4] | | 36 |

| Comp. | Educt | Educt | Product | Yield [%] |
|---|---|---|---|---|
| 13x | | [591-50-4] | | 19 |

| Comp. | Educt | Educt | Product | Yield [%] |
|---|---|---|---|---|
| 13y | | [591-50-4] | | 53 |

| Comp. | Educt | Educt | Product | Yield [%] |
|---|---|---|---|---|
| 13z | (structure) [611-33-6] | (structure) | (structure) | 23 |

| Comp. | Educt | Educt | Product | Yield [%] |
|---|---|---|---|---|
| 13aa | 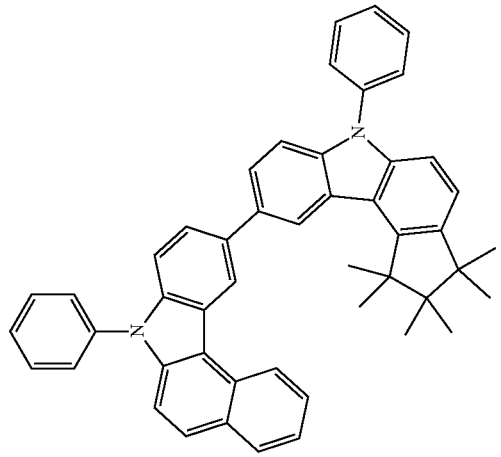 | 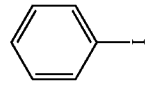  [591-50-4] | | 65 |

-continued

| Comp. | Educt | Educt | Product | Yield [%] |
|---|---|---|---|---|
| 13ab | (structure) | iodobenzene | (structure) | 34 |
| 13ac | (structure) | 3-bromobiphenyl [591-50-4] | (structure) | 71 |

| Comp. | Educt | Educt | Product | Yield [%] |
|---|---|---|---|---|
| 13ad | 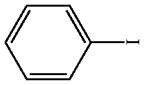 [13ad structure] | 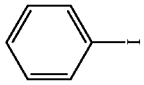 [2113-57-7] | 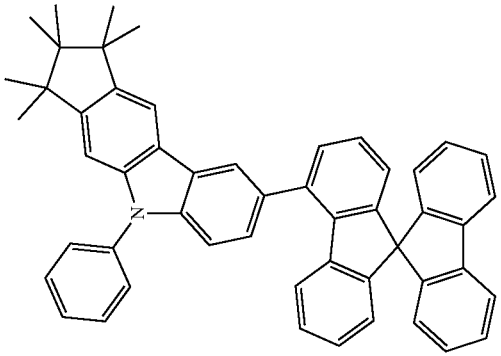 | 59 |
| 13ae | 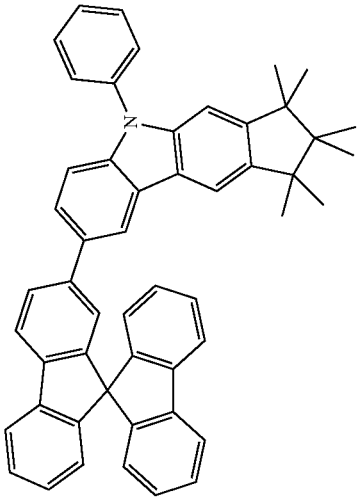 [13ae structure] | [591-50-4] | | 35 |

| Comp. | Educt | Educt | Product | Yield [%] |
|---|---|---|---|---|
| 13af | 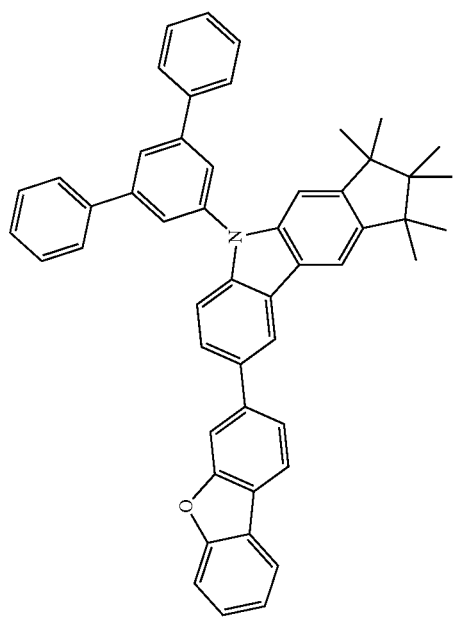 | 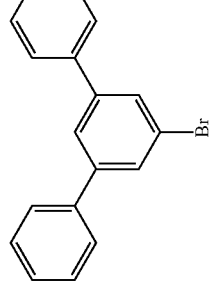 | (structure shown) | 42 |
[103068-20-8]

| Comp. | Educt | Educt | Product | Yield [%] |
|---|---|---|---|---|
| 13ag | 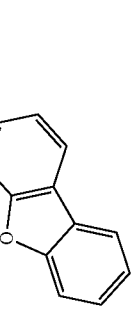 | 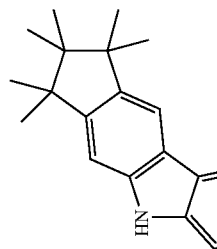 | 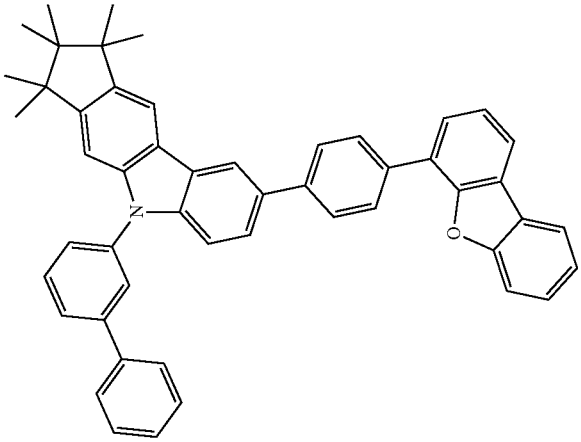 | 39 |
| | | [2113-57-7] | | |

| Comp. | Educt | Educt | Product | Yield [%] |
|---|---|---|---|---|
| 13ah | 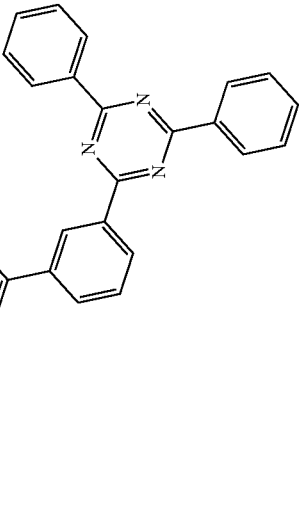 | 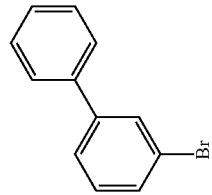 [2113-57-7] | | 64 |

| Comp. | Educt | Educt | Product | Yield [%] |
|---|---|---|---|---|
| 13ai | 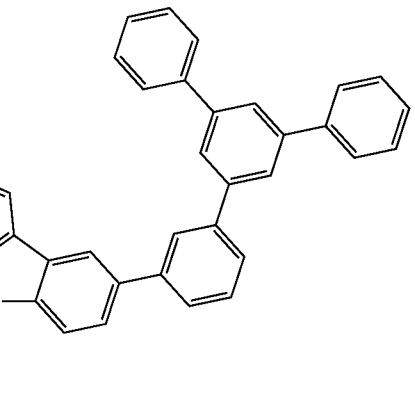 | 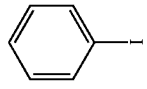  [591-50-4] | | 28 |

| Comp. | Educt | Educt | Product | Yield [%] |
|---|---|---|---|---|
| 13aj | 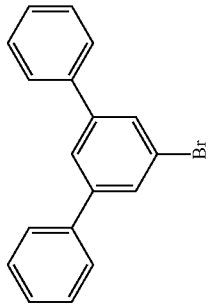 | 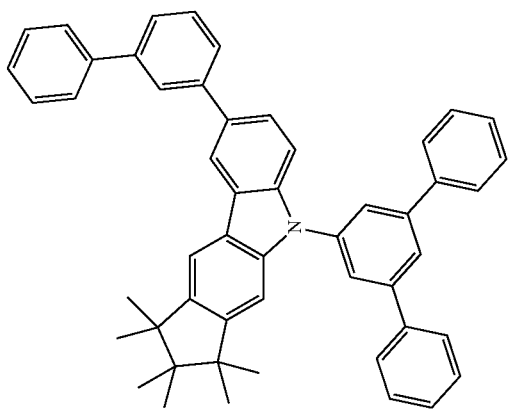 | 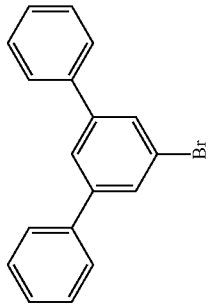 | 31 |
[103068-20-8]

| Comp. | Educt | Educt | Product | Yield [%] |
|---|---|---|---|---|
| 13ak | 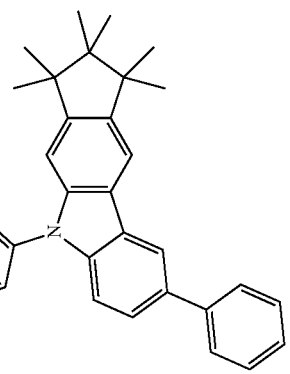 | 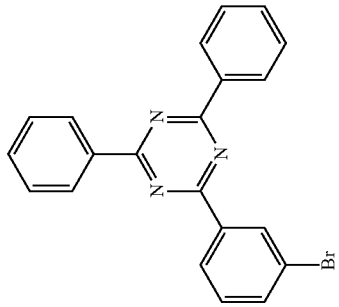 | | 47 |

| Comp. | Educt | Educt | Product | Yield [%] |
|---|---|---|---|---|
| 13al | 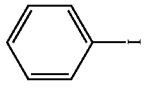 | 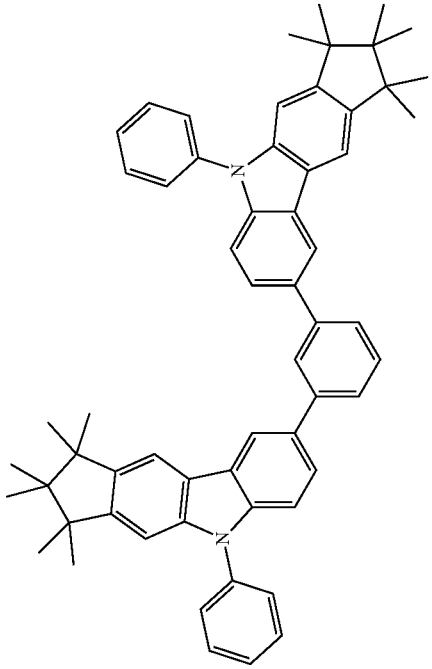 [864377-31-1] [591-51-4] 2.0 eq | | 51 |

201
Example 5
Synthesis of (6-Bromo-1,1,2,2,3,3-hexamethyl-indan-5-yl)-(1,1,2,2,3,3-hexamethyl-indan-5-yl)-amine (17a)
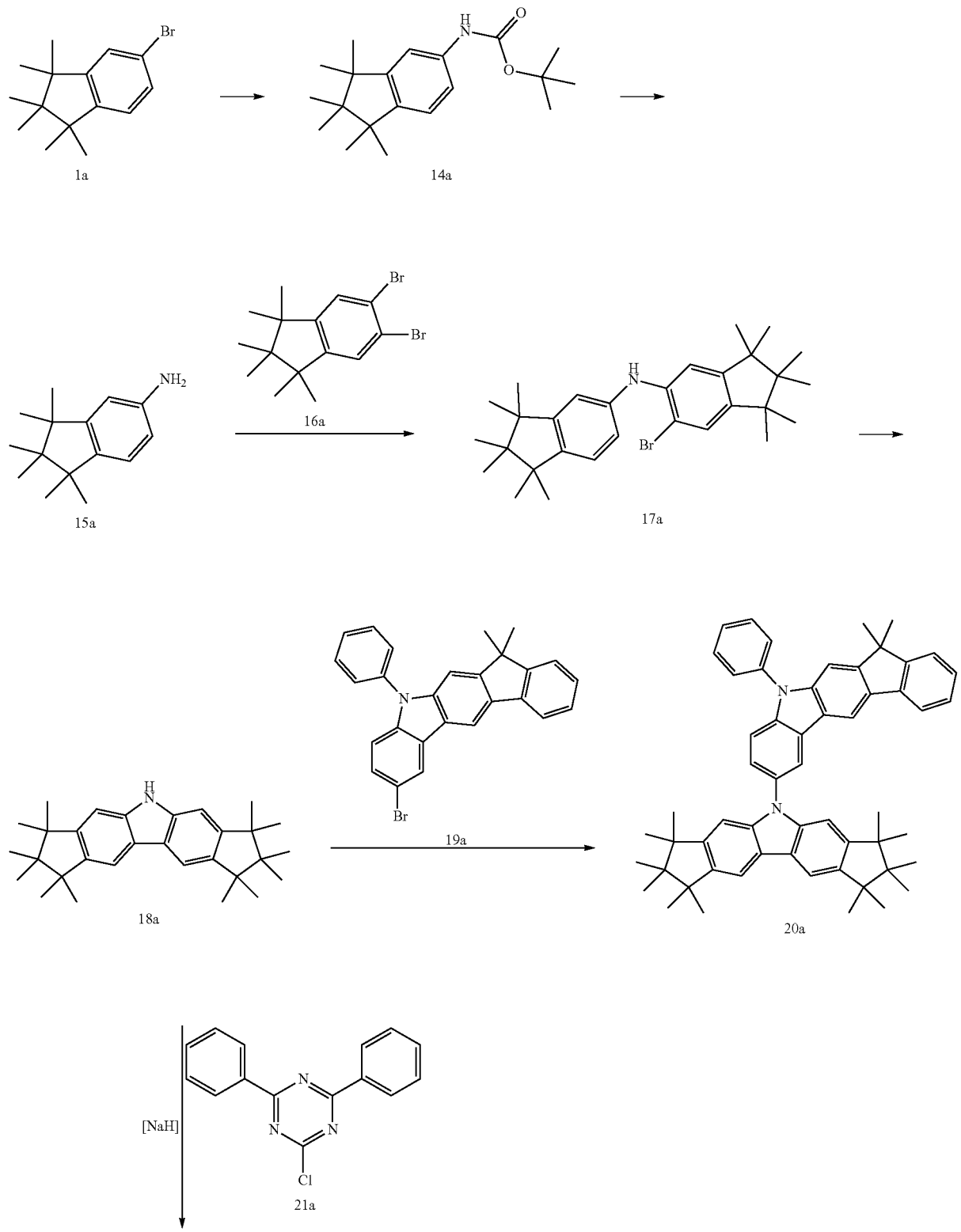

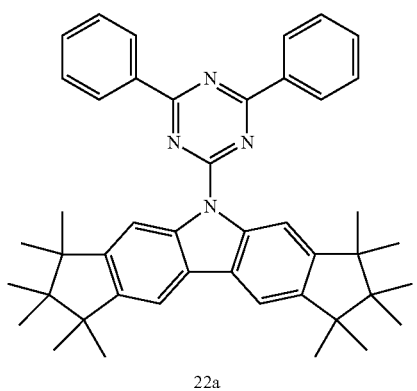

22a

Synthesis of (1,1,2,2,3,3-Hexamethyl-indan-5-yl)-carbamic acid tert-butyl ester (14a)

50.0 g (178 mmol, 1.0 eq) 5-Bromo-1,1,2,2,3,3-hexamethyl-indan5-Bromo-1,1,2,2,3,3-hexamethyl-indan 1a, 31.2 g (267 mmol, 1.5 eq) tert.-butylcarbamate and 146 g (356 mmol, 2.0 eq) cesium carbonate are dissolved in 750 ml tert.-butanol and degassed for 20 minutes. Then, 6.52 g (7.12 mmol, 0.04 eq) Tris(dibenzylideneacetone)dipalladium(0) and 4.38 g (10.7 mmol, 0.04 eq) S-Phos are added and the mixture refluxed overnight. After the reaction is finished, the solvent is removed in vacuo. 52.0 g (164 mmol, 92%) brownish oil are obtained.

Synthesis of 1,1,2,2,3,3-Hexamethyl-indan-5-ylamine (15a)

52.0 g (164 mmol, 1.0 eq) (1,1,2,2,3,3-Hexamethyl-indan-5-yl)-carbamic acid tert-butyl ester 14a are dissolved in 500 ml dichloromethan and treated with 63.2 ml (820 mmol, 5.0 eq) trifluoroacetic acid. The reaction is stirred at room temperature for 14 hours and after the reaction is finished, the solvent is evaporated, the crude is re-dissolved in ethylacetate and washed with sodium carbonate. The solution is dried over sodium sulfate and the solvent removed in vacuo. 31.7 g (146 mmol, 89%) of desired product 15a are obtained as slightly brownish oil.

Synthesis of (6-Bromo-1,1,2,2,3,3-hexamethyl-indan-5-yl)-(1,1,2,2,3,3-hexamethyl-indan-5-yl)-amine (17a)

In a 2 L four-necked flask 30.0 g (138 mmol, 1.0 eq) of 1,1,2,2,3,3-Hexamethyl-indan-5-ylamine 15a are dissolved together with 53.3 g (148 mmol, 1.07 eq) 5,6-dibromo-2,3-dihydro-1,1,2,2,3,3-hexamethyl-1H-Indene [1541101-19-2] 16a and 35.5 g (359 mmol, 2.6 eq) sodium-tert-butoxide in 600 ml of dried toluene. The mixture is degassed for 30 minutes and then, 310 mg (1.38 mmol, 0.01 eq) of palladium (II)-acetate and 765 mg (1.38 mmol, 0.01 eq) 1,1'-bis (diphenylphosphino)ferrocene are added. The reaction is heated to 100° C. for 12 hours. After the reaction is finished, 200 ml water are added and the mixture stirred for additional 45 min. Then, the aqueous phase is separated and the organic phase is washed 3 times with water. The combined aqueous layers are extracted once with toluene. The combined organic layers are dried over sodium sulfate and the solvent is removed in vacuo. 43.2 g (86.9 mmol, 63%) of desired secondary amine 17a are obtained as brownish oil.

Analogously the following compounds can be obtained:

| Comp. | Educt | Educt | Product | Yield [%] |
|---|---|---|---|---|
| 17b | [108714-73-4] | [1541101-19-2] | | 45 |
| 17c | [4106-66-5] | [1541101-19-2] | | 65 |

| Comp. | Educt | Educt | Product | Yield [%] |
|---|---|---|---|---|
| 17d | 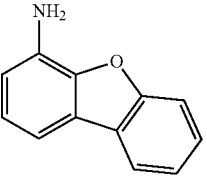 [SMILES: Nc1cccc2c1oc1ccccc12]<br>[50548-43-1] | 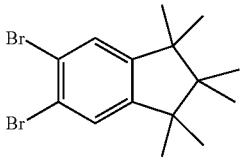 [SMILES: CC1(C)c2cc(Br)c(Br)cc2C(C)(C)C1(C)C]<br>[1541101-19-2] | 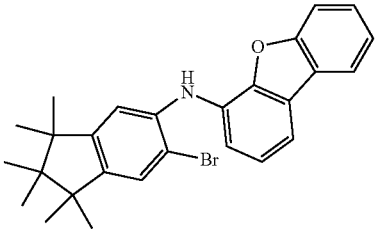 [SMILES: CC1(C)c2cc(Br)c(Nc3cccc4c3oc3ccccc34)cc2C(C)(C)C1(C)C] | 78 |
| 17e | 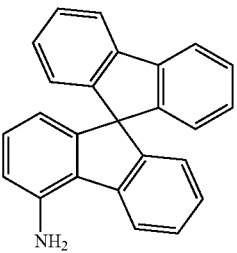 [SMILES: Nc1cccc2c1-c1ccccc1C21c2ccccc2-c2ccccc21]<br>[1579281-06-3] | 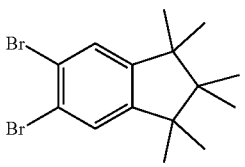 [SMILES: CC1(C)c2cc(Br)c(Br)cc2C(C)(C)C1(C)C]<br>[1541101-19-2] | 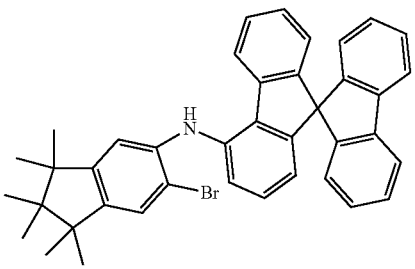 [SMILES: CC1(C)c2cc(Br)c(Nc3cccc4c3-c3ccccc3C43c4ccccc4-c4ccccc43)cc2C(C)(C)C1(C)C] | 62 |
| 17f | 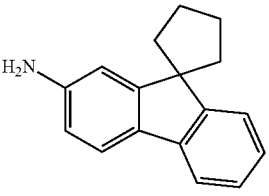 [SMILES: Nc1ccc2c(c1)C1(CCCC1)c1ccccc1-2]<br>[133872-22-7] | 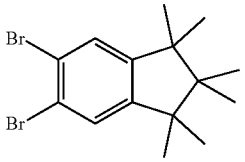 [SMILES: CC1(C)c2cc(Br)c(Br)cc2C(C)(C)C1(C)C]<br>[1541101-19-2] | 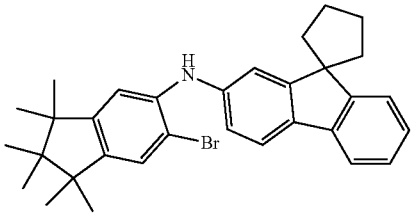 [SMILES: CC1(C)c2cc(Br)c(Nc3ccc4c(c3)C3(CCCC3)c3ccccc3-4)cc2C(C)(C)C1(C)C] | 71 |
| 17g | 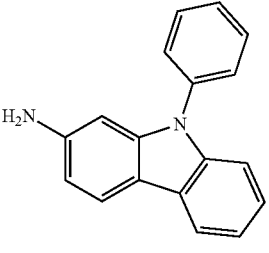 [SMILES: Nc1ccc2c3ccccc3n(-c3ccccc3)c2c1]<br>[1257982-95-8] | 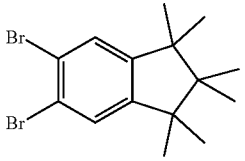 [SMILES: CC1(C)c2cc(Br)c(Br)cc2C(C)(C)C1(C)C]<br>[1541101-19-2] | 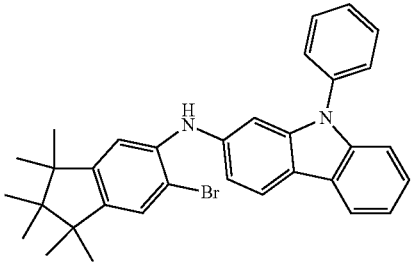 [SMILES: CC1(C)c2cc(Br)c(Nc3ccc4c5ccccc5n(-c5ccccc5)c4c3)cc2C(C)(C)C1(C)C] | 52 |
| 17h | 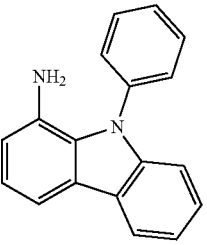 [SMILES: Nc1cccc2c3ccccc3n(-c3ccccc3)c12]<br>[855180-11-9] | 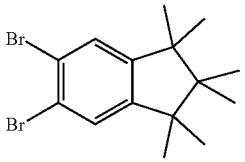 [SMILES: CC1(C)c2cc(Br)c(Br)cc2C(C)(C)C1(C)C]<br>[1541101-19-2] | 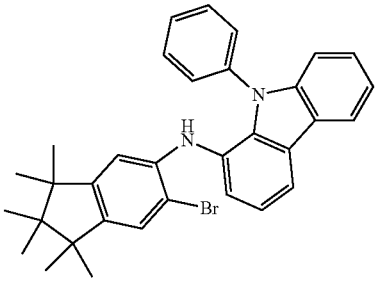 [SMILES: CC1(C)c2cc(Br)c(Nc3cccc4c5ccccc5n(-c5ccccc5)c34)cc2C(C)(C)C1(C)C] | 59 |

| Comp. | Educt | Educt | Product | Yield [%] |
|---|---|---|---|---|
| 17i | 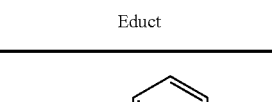 [71041-19-5] | [1541101-19-2] | | 83 |

Example 6

Synthesis of Compound 18a

A 1 L four-necked flask is charged with 43.0 g (86.6 mmol, 1.0 eq) of 17a, 29.9 g (217 mmol, 2.5 eq) potassium carbonate and 500 ml of 1-methyl-2-pyrrolidon. After the mixture is degassed for 25 minutes, 2.65 g (26.0 mmol, 0.30 eq) pivalic acid, 389 mg (1.73 mmol, 0.02 eq) palladium (II)-acetate and 3.46 ml (3.46 mmol, 0.04 eq) of a 1 mol/l tri-tert.-butylphoshine solution in toluene are added. The reaction is stirred overnight at 130° C. and after the reaction is finished, the solvent and the pivalic acid are removed in vacuo and the remaining solid is dissolved in 50 ml toluene. The solution is washed 3 times with 75 ml water and dried over sodium sulfate. After evaporation of the solvent the crude product is purified by crystallization from n-heptane/toluene. 23.7 g (56.9 mmol, 66%) of product 18a are obtained as light-brown crystals.

Analogously the following compounds can be obtained:

| Comp. | Educt | Product | Yield [%] |
|---|---|---|---|
| 18b | 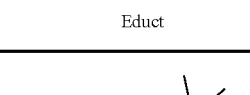 | | 37 |
| 18c | | | 24 |
| 18d | 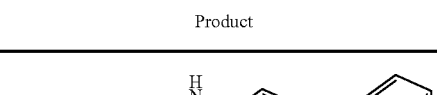 | | 74 |

| Comp. | Educt | Product | Yield [%] |
|---|---|---|---|
| 18e | | | 88 |
| 18f | | | 38 |
| 18g | | | 21 |
| 18h | | | 91 |
| 18i | | | 42 |

Example 7

Synthesis of Compound 20a 25.0 g (56.9 mmol, 1.00 eq) 7-Bromo-12,12-dimethyl-10-phenyl-10,12-dihydro-10-aza-indeno[2,1-b]fluorine 19a are dissolved with 23.7 g 56.9 mmol, 1.00 eq) of educt 18a and 8.46 g (85.3 mmol, 1.50 eq) sodium-t-butoxide in 500 ml of dried toluene. After the reaction is degassed for 30 minutes 1.30 g (1.42 mmol, 0.03 eq) Tris(dibenzylideneacetone)di-palladium(0) and 2.84 ml (2.84 mmol, 0.05 eq) tri-tert-butylphosphine solution are added. The mixture is refluxed overnight and after the reaction is finished the solution is concentrated in vacuo. The precipitate is filtered and washed with water and ethanol. The product is purified by hot extraction with heptane/toluene 3:1 and three times recrystallized with toluene/heptane. After two sublimations 19.8 g (25.6 mmol, 45%) of final product 20a are obtained as a colorless solid in a purity >99.9% (HPLC).

Analogously the following compounds can be obtained:

| Comp. | Educt | Educt | Product | Yield [%] |
|---|---|---|---|---|
| 20b | 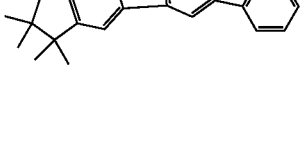 | 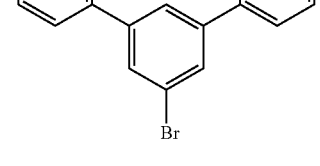 [103068-20-8] | 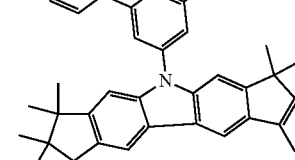 | 56 |
| 20c | 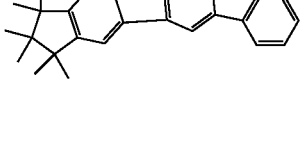 | 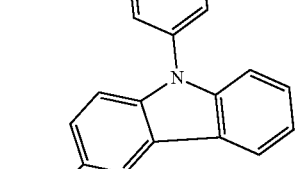 [1153-85-1] | 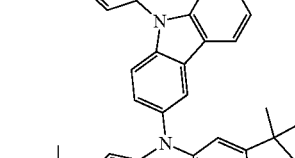 | 61 |
| 20d | 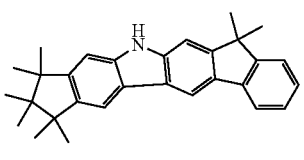 [SMILES: CC1(C)c2ccccc2-c2cc3c(cc21)[nH]c1cc2c(cc13)C(C)(C)C(C)(C)C2(C)C] | 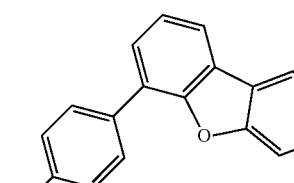 [955959-84-9] | 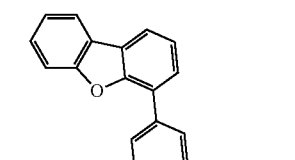 | 34 |
| 20e | 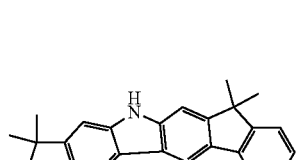 | 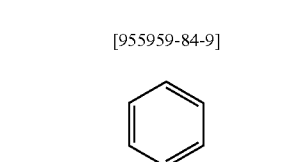 [86437-31-1] | 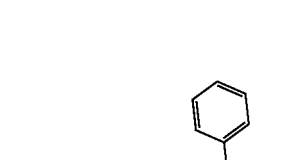 | 45 |

-continued

| Comp. | Educt | Educt | Product | Yield [%] |
|---|---|---|---|---|
| 20f | | [591-50-4] | | 17 |
| 20g | | [1153-85-1] | | 37 |
| 20h | | [591-50-4] | | 47 |
| 20i | | [864377-31-1] | | 21 |

| Comp. | Educt | Educt | Product | Yield [%] |
|---|---|---|---|---|
| 20j | | [864377-31-1] | | 29 |
| 20k | | [591-50-4] | | 53 |
| 20l | | [23449-08-3] | | 26 |
| 20m | | [2113-57-7] | | 44 |

Example 8

Synthesis of Compound 22a

To a suspension of 1.73 g (43.3 mmol, 1.2 eq) 60 wt-% sodium hydride in 50 ml dried DMF 15.0 g (36.1 mmol, 1.0 eq) of educt 20a in 50 ml dried DMF are added slowly. After the reaction is finished 9.66 g (36.1 mmol, 1.0 eq) of 2-Chloro-4,6-diphenyl-[1,3,5]triazine in another 50 ml of toluene are added to the mixture. After stirring overnight 100 ml water are added drop-wise and the precipitate filtered, washed with water and ethanol and dried in vacuo. The product is purified by hot extraction with heptane/toluene 1:1 and two times recrystallized with toluene/heptane. After two sublimations 7.30 g (11.3 mmol, 31%) of final product 20a are obtained as a colorless solid in a purity >99.9% (HPLC).

Analogously the following compounds can be obtained:

| Comp. | Educt | Educt | Product | Yield [%] |
|---|---|---|---|---|
| 22b | | [3842-55-5] | | 45 |
| 22c | | [2915-16-4] | | 61 |
| 22d | | [3842-55-5] | | 22 |
| 22e | | [2915-16-4] | | 38 |

| Comp. | Educt | Educt | Product | Yield [%] |
|---|---|---|---|---|
| 22f | | | [3842-55-5] | 12 |
| 22g | | | [3842-55-5] | 19 |

Example 9

Device Preparation and Characterization

The following examples V1 to E13 (see Table 1 and 2) show data of various OLEDs.

Substrate Pre-Treatment of Examples V1-E13:

Glass plates with structured ITO (50 nm, indium tin oxide) are coated with 20 nm PEDOT:PSS (Poly(3,4-ethylenedioxythiophene) poly(styrenesulfonate, CLEVIOS™ P VP AI 4083 from Heraeus Precious Metals GmbH Germany, spin-coated from a water-based solution) and form the substrates on which the OLEDs are processed.

The OLEDs have in principle the following layer structure: substrate/hole-transport layer (HTL)/optional interlayer (IL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer with a thickness of 100 nm. The exact layer structure is denoted in Table 1. The materials used for the OLED fabrication are presented in Table 3.

All materials are applied by thermal vapour deposition in a vacuum chamber. The emission layer here always consists of at least one matrix material (host material) and an emitting dopant (emitter), which is admixed with the matrix material or matrix materials in a certain proportion by volume by co-evaporation. An expression such as IC1:M1:TEG1 (55%:35%:10%) here means that material IC1 is present in the layer in a proportion by volume of 55%, M1 is present in the layer in a proportion of 35% and TEG1 is present in the layer in a proportion of 10%. Analogously, the electron-transport layer may also consist of a mixture of two materials.

The OLEDs are characterised by standard methods. For this purpose, the electroluminescence spectra, the current efficiency (CE1000, measured in cd/A at 1000 cd/m$^2$), the luminous efficacy (LE1000, measured in lm/W at 1000 cd/m$^2$), the external quantum efficiency (EQE1000, measured in % at 1000 cd/m$^2$) and the voltage (U1000, measured at 1000 cd/m$^2$ in V) are determined from current/voltage/luminance characteristic lines (IUL characteristic lines) assuming a Lambertian emission profile. The electroluminescence (EL) spectra are recorded at a luminous density of 1000 cd/m$^2$ and the CIE 1931 x and y coordinates are then calculated from the EL spectrum.

The device data of various OLEDs is summarized in Table 2. The example V1 is a comparison example according to the state-of-the-art. The examples E1-E13 show data of inventive OLEDs.

In the following section several examples are described in more detail to show the advantages of the inventive OLEDs.

Use of Inventive Compounds as Host Material in Phosphorescent OLEDs

The use of the inventive compounds as host material results in significantly improved OLED device data compared to state-of-the-art materials, especially with respect to device efficiency.

The use of the inventive material 13a as host mixed with IC1 results in 10% improved external quantum efficiency compared to a device containing the material IC3 (comparison of example V1 with E1).

TABLE 1

OLED layer structure

| Bsp. | HIL Dicke | IL Dicke | HTL Dicke | EBL Dicke | EML Dicke | HBL Dicke | ETL Dicke |
|---|---|---|---|---|---|---|---|
| V1 | --- | SpA1 70 nm | HATCN 5 nm | SpMA1 90 nm | IC1:IC3:TEG1 (65%:30%:5%) 30 nm | IC1 10 nm | ST2:LiQ (50%:50%) 30 nm |
| E1 | --- | SpA1 70 nm | HATCN 5 nm | SpMA1 90 nm | IC1:13a:TEG1 (65%:30%:5%) 30 nm | IC1 10 nm | ST2:LiQ (50%:50%) 30 nm |
| E2 | --- | SpA1 70 nm | HATCN 5 nm | SpMA1 90 nm | IC1:13f:TEG1 (45%:45%:10%) 30 nm | IC1 10 nm | ST2:LiQ (50%:50%) 30 nm |
| E3 | --- | SpA1 70 nm | HATCN 5 nm | SpMA1 90 nm | 13v:TEG1 (90%:10%) 30 nm | IC1 10 nm | ST2:LiQ (50%:50%) 30 nm |
| E4 | SpA1 70 nm | HATCN 5 nm | SpMA1 80 nm | 13aa 10 nm | IC1:IC3:TEG1 (25%:65%:10%) 30 nm | IC1 10 nm | ST2:LiQ (50%:50%) 30 nm |
| E5 | --- | SpA1 70 nm | HATCN 5 nm | SpMA1 90 nm | IC1:13ag:TEG1 (35%:55%:10%) 30 nm | IC1 10 nm | ST2:LiQ (50%:50%) 30 nm |
| E6 | --- | SpA1 70 nm | HATCN 5 nm | SpMA1 90 nm | IC1:13aj:TEG1 (35%:55%:10%) 30 nm | IC1 10 nm | ST2:LiQ (50%:50%) 30 nm |
| E7 | --- | SpA1 70 nm | HATCN 5 nm | SpMA1 90 nm | IC1:20g:TEG1 (45%:50%:5%) 30 nm | IC1 10 nm | ST2:LiQ (50%:50%) 30 nm |
| E8 | --- | SpA1 70 nm | HATCN 5 nm | SpMA1 90 nm | IC1:20h:TEG1 (45%:50%:5%) 30 nm | IC1 10 nm | ST2:LiQ (50%:50%) 30 nm |
| E9 | --- | SpA1 70 nm | HATCN 5 nm | SpMA1 90 nm | 20j:TEG1 (90%:10%) 30 nm | IC1 10 nm | ST2:LiQ (50%:50%) 30 nm |
| E10 | SpA1 70 nm | HATCN 5 nm | SpMA1 80 nm | 20 m 10 nm | IC1:IC3:TEG1 (25%:65%:10%) 30 nm | IC1 10 nm | ST2:LiQ (50%:50%) 30 nm |
| E11 | --- | SpA1 70 nm | HATCN 5 nm | SpMA1 90 nm | 22c:TEG1 (90%:10%) 30 nm | IC1 10 nm | ST2:LiQ (50%:50%) 30 nm |
| E12 | --- | SpA1 70 nm | HATCN 5 nm | SpMA1 90 nm | 22f:TEG1 (90%:10%) 30 nm | IC1 10 nm | ST2:LiQ (50%:50%) 30 nm |
| E13 | --- | SpA1 70 nm | HATCN 5 nm | SpMA1 90 nm | IC1:13p:TEG1 (45%:45%:10%) 30 nm | IC1 10 nm | ST2:LiQ (50%:50%) 30 nm |

TABLE 2

OLED device data

| Example | U1000 (V) | CE1000 (cd/A) | LE1000 (lm/W) | EQE 1000 | CIE x/y at 1000 cd/m$^2$ |
|---|---|---|---|---|---|
| V1 | 3.3 | 60 | 57 | 16.1% | 0.32/0.64 |
| E1 | 3.4 | 66 | 61 | 17.8% | 0.32/0.63 |
| E2 | 3.5 | 63 | 57 | 16.9% | 0.32/0.64 |
| E3 | 3.8 | 60 | 50 | 16.5% | 0.32/0.63 |
| E4 | 3.6 | 55 | 48 | 15.2% | 0.31/0.64 |
| E5 | 3.7 | 60 | 51 | 16.7% | 0.33/0.63 |
| E6 | 3.8 | 62 | 51 | 16.9% | 0.34/0.63 |
| E7 | 3.6 | 63 | 55 | 17.1% | 0.33/0.63 |
| E8 | 3.7 | 64 | 54 | 17.3% | 0.33/0.63 |
| E9 | 3.3 | 55 | 52 | 15.5% | 0.32/0.63 |
| E10 | 3.4 | 59 | 55 | 15.9% | 0.33/0.63 |
| E11 | 3.6 | 60 | 52 | 16.4% | 0.32/0.63 |
| E12 | 3.6 | 58 | 51 | 15.7% | 0.33/0.63 |
| E13 | 3.5 | 61 | 55 | 16.7% | 0.32/0.64 |

TABLE 3

Chemical structures of the OLED materials

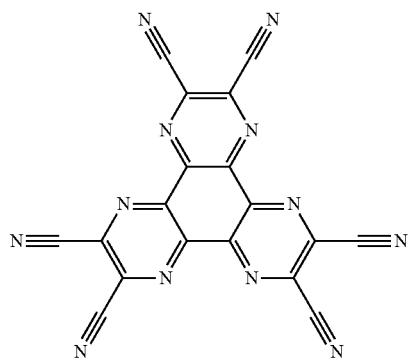 [SMILES: N#Cc1nc2c3nc(C#N)c(C#N)nc3c3nc(C#N)c(C#N)nc3c2nc1C#N]

HATCN

TABLE 3-continued
Chemical structures of the OLED materials
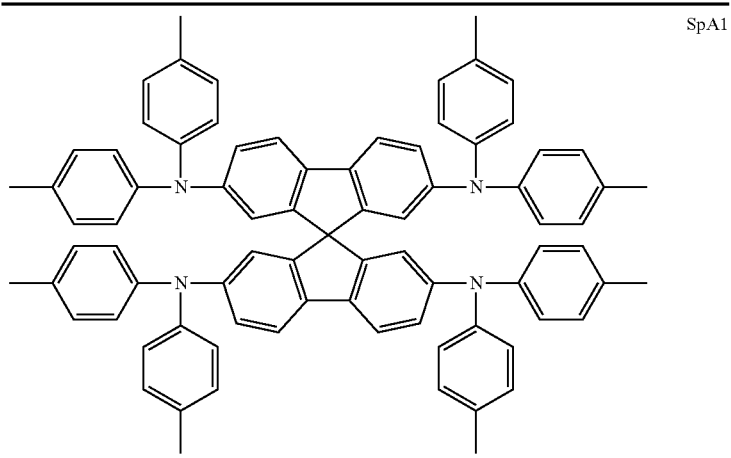
SpA1
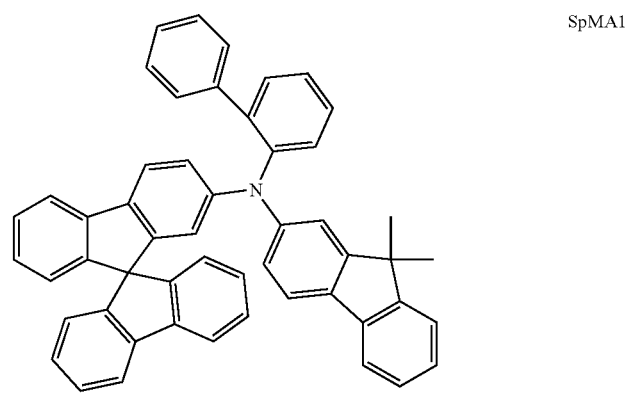
SpMA1
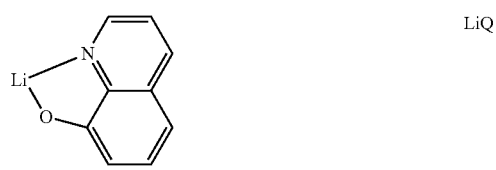
LiQ
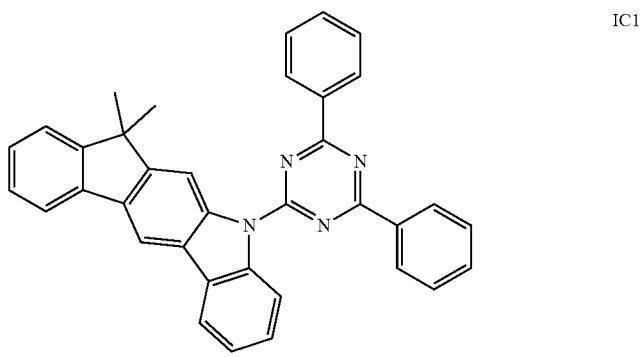
IC1
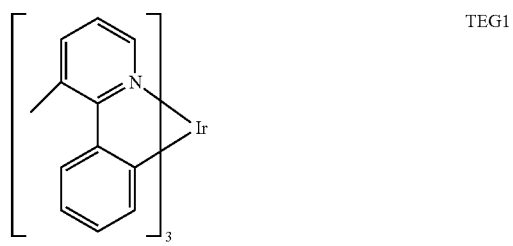
TEG1

TABLE 3-continued
Chemical structures of the OLED materials
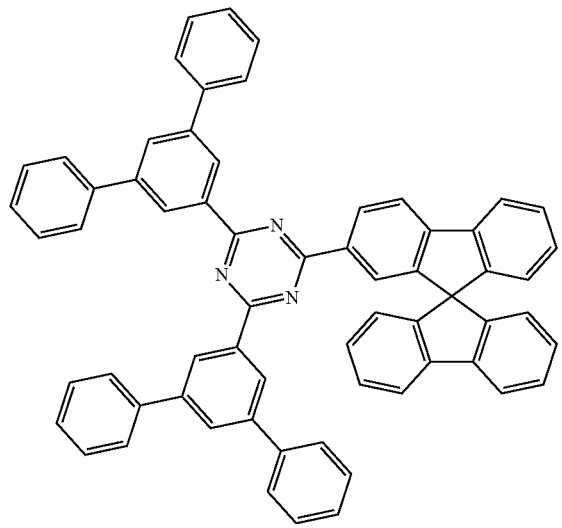 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ST2
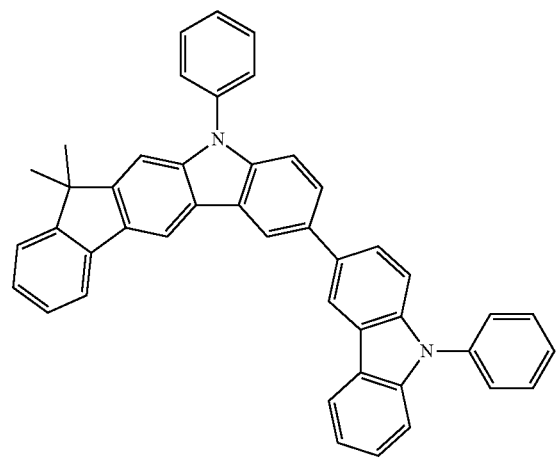 [SMILES: CC1(C)c2ccccc2-c2cc3c4cc(-c5ccc6c(c5)c5ccccc5n6-c5ccccc5)ccc4n(-c4ccccc4)c3cc21]
IC3
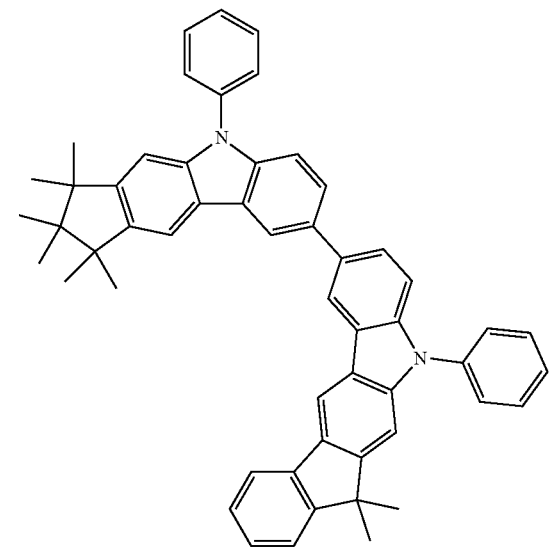 [SMILES: CC1(C)c2ccccc2-c2cc3c4cc(-c5ccc6c(c5)c5cc7c(cc5n6-c5ccccc5)C(C)(C)C(C)(C)C7(C)C)ccc4n(-c4ccccc4)c3cc21]
13a TABLE 3-continued
Chemical structures of the OLED materials
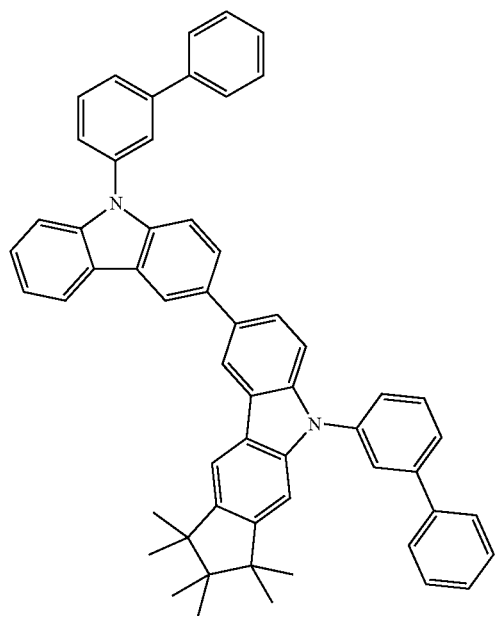 [SMILES: CC1(C)c2cc3c4cc(-c5ccc6c(c5)c5ccccc5n6-c5cccc(-c6ccccc6)c5)ccc4n(-c4cccc(-c5ccccc5)c4)c3cc2C(C)(C)C1(C)C]
13f
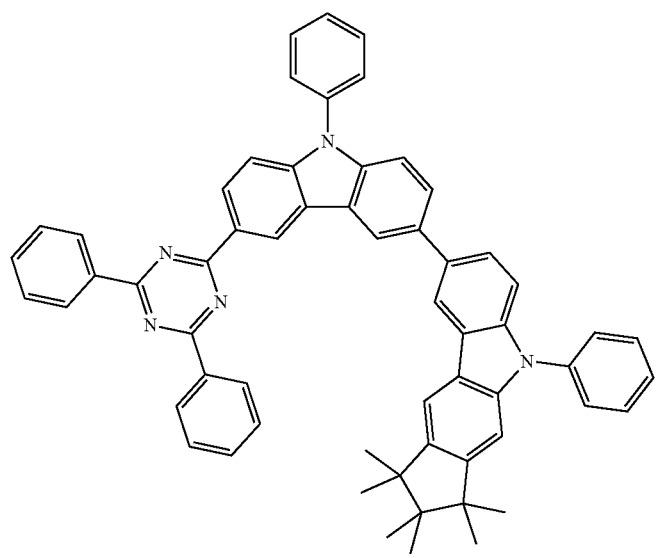 [SMILES: CC1(C)c2cc3c4cc(-c5ccc6c(c5)c5cc(-c7nc(-c8ccccc8)nc(-c8ccccc8)n7)ccc5n6-c5ccccc5)ccc4n(-c4ccccc4)c3cc2C(C)(C)C1(C)C]
13v TABLE 3-continued
Chemical structures of the OLED materials
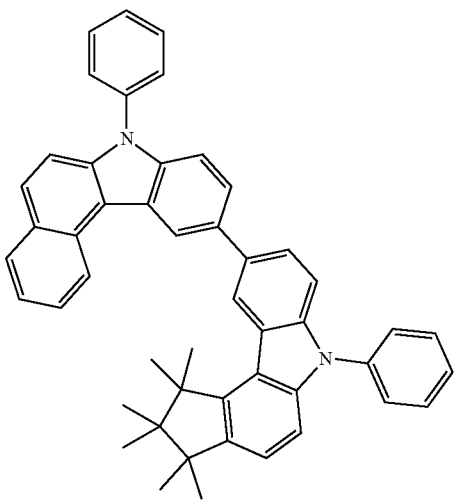 [SMILES: CC1(C)c2ccc3c(c2C(C)(C)C1(C)C)c1cc(-c2ccc4c(c2)c2c5ccccc5ccc2n4-c2ccccc2)ccc1n3-c1ccccc1]
13aa
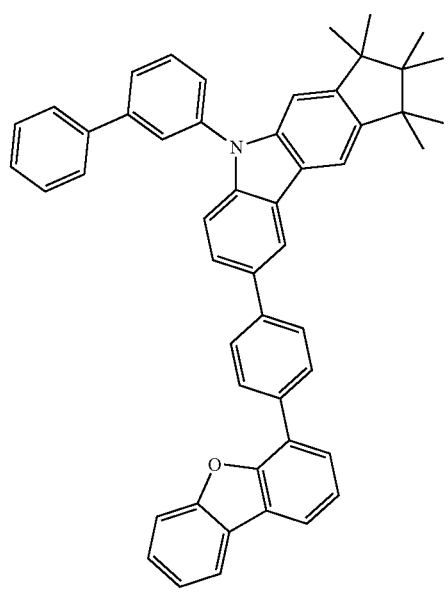 [SMILES: CC1(C)c2cc3c4cc(-c5ccc(-c6cccc7c6oc6ccccc67)cc5)ccc4n(-c4cccc(-c5ccccc5)c4)c3cc2C(C)(C)C1(C)C]
13ag
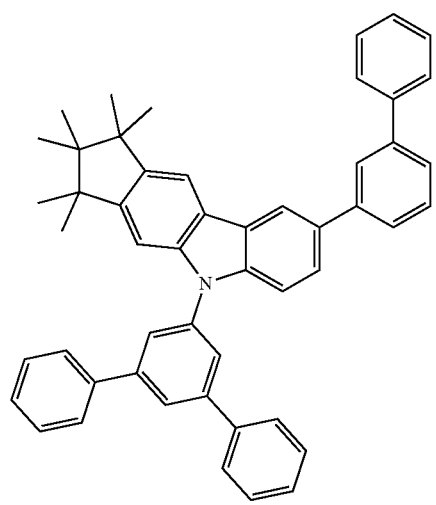 [SMILES: CC1(C)c2cc3c4cc(-c5cccc(-c6ccccc6)c5)ccc4n(-c4cc(-c5ccccc5)cc(-c5ccccc5)c4)c3cc2C(C)(C)C1(C)C]
13aj TABLE 3-continued
Chemical structures of the OLED materials
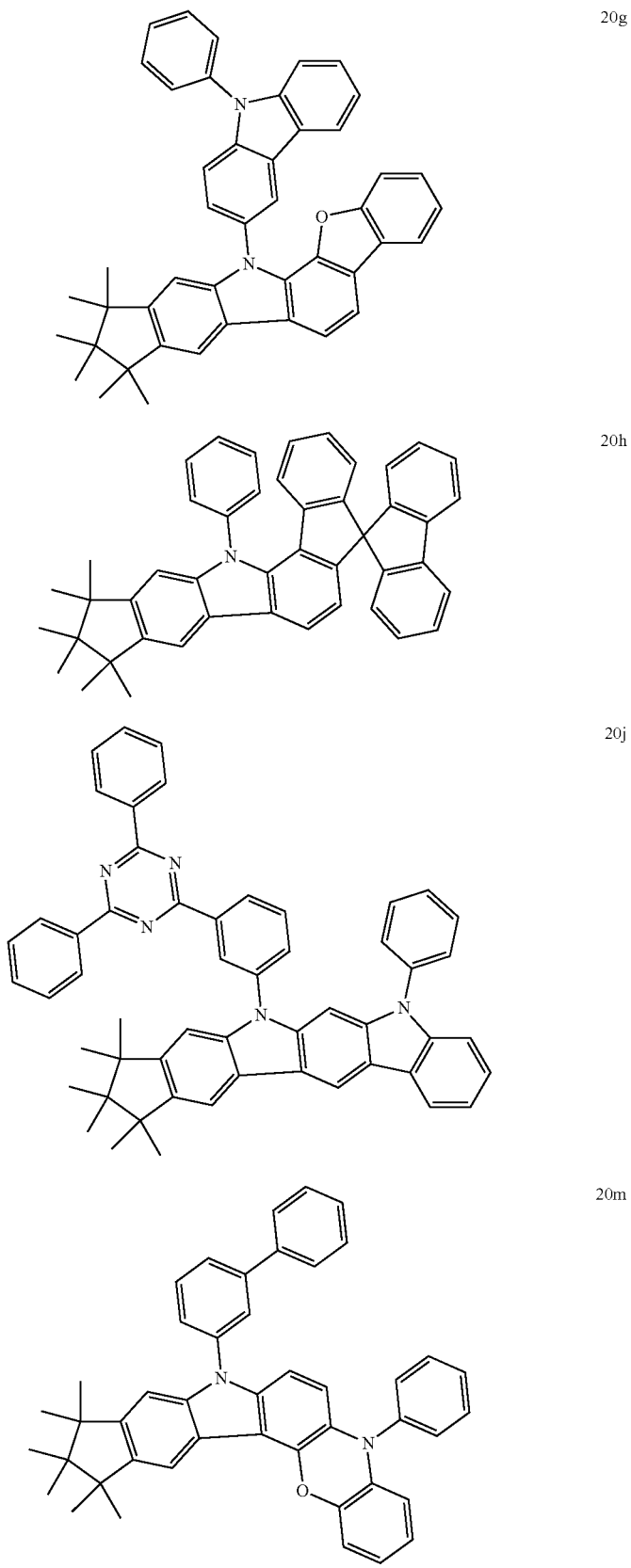
20g
20h
20j
20m TABLE 3-continued
Chemical structures of the OLED materials
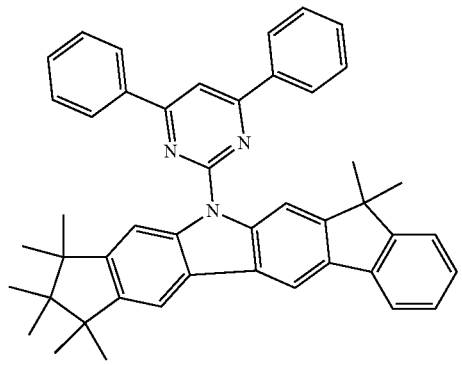 [SMILES: CC1(C)c2ccccc2-c2cc3c4cc5c(cc4n(-c4nc(-c6ccccc6)cc(-c6ccccc6)n4)c3cc21)C(C)(C)C(C)(C)C5(C)C]
22c
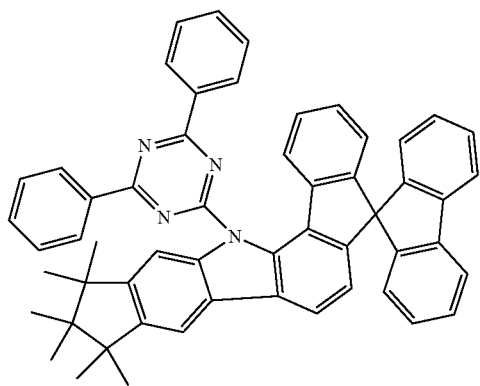 [SMILES: CC1(C)c2cc3c4ccc5c(c4n(-c4nc(-c6ccccc6)nc(-c6ccccc6)n4)c3cc2C(C)(C)C1(C)C)-c1ccccc1C51c2ccccc2-c2ccccc21]
22f
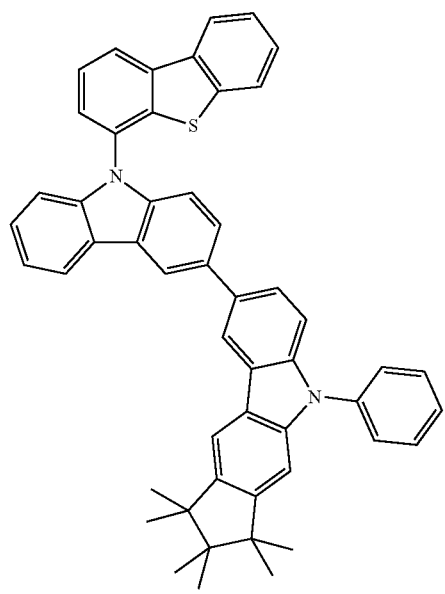 [SMILES: CC1(C)c2cc3c4cc(-c5ccc6c(c5)c5ccccc5n6-c5cccc6c5sc5ccccc56)ccc4n(-c4ccccc4)c3cc2C(C)(C)C1(C)C]
13p

The invention claimed is:
1. A compound according to the formula (1),

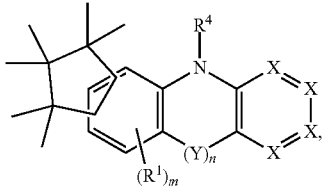

wherein:
Y is at each occurrence same or different and selected from $C(R^1)_2$, $N(R^1)$, $C(=O)$, $C(=S)$, O, or S;
X is at each occurrence same or different, and X includes $CR^1$ or N;
$R^1$ is at each occurrence same or different, and $R^1$ includes H, D, F, Cl, Br, I, CHO, $N(Ar^1)_2$, $C(=O)Ar^1$, $P(=O)(Ar^1)_2$, $S(=O)Ar^1$, $S(=O)_2Ar^1$, $CR^2=CR^2Ar^1$, CN, $NO_2$, $Si(R^2)_3$, $B(OR^2)_2$, $B(R^2)_2$, $B(N(R^2)_2)_2$, $OSO_2R^2$, a straight-chain alkyl, alkoxy, or thioalkoxy group having 1 to 40 C atoms or a branched or cyclic alkyl, alkoxy, or thioalkoxy group having 3 to 40 C atoms, each of which may be substituted by one or more $R^2$, wherein one or more non-adjacent methylene groups may be replaced by $R^2C=CR^2$, $C≡C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S, or $C(=O)NR^2$, and wherein one or more hydrogen atoms can include a substitution selected from D, F, Cl, Br, I, CN, $NO_2$, or an aromatic or heteroaromatic ring system having 5 to 60 aromatic ring atoms, which may in each case be substituted by one or more radicals $R^2$, or an aryloxy or heteroaryloxy group having 5 to 40 aromatic ring atoms, which is optionally substituted by one or more radicals $R^2$, or an aralkyl or heteroaralkyl group having 5 to 40 aromatic ring atoms, which is optionally substituted by one or more radicals $R^2$, or a combination of these systems;
$R^2$ is at each occurrence same or different, and $R^2$ includes H, D, F, Cl, Br, I, $N(R^3)_2$, CN, $NO_2$, $Si(R^3)_3$, $B(OR^3)_2$, $C(=O)R^3$, $P(=O)(R^3)_2$, $S(=O)R^3$, $S(=O)_2R^3$, $OSO_2R^3$, a straight-chain alkyl, alkoxy or thioalkoxy group having 1 to 40 C atoms or a straight-chain alkenyl or alkynyl having 2 to 40 C atoms or a branched or cyclic alkyl, alkenyl, alkynyl, alkoxy, alkylalkoxy, or thioalkoxy group having 3 to 40 C atoms, each of which is optionally substituted by one or more radicals $R^3$, where one or more non-adjacent $CH_2$ groups is optionally replaced by $R^3C=CR^3$, $C≡C$, $Si(R^3)_2$, $Ge(R^3)_2$, $Sn(R^3)_2$, $C=O$, $C=S$, $C=Se$, $C=NR^3$, $P(=O)(R^3)$, SO, $SO_2$, $NR^3$, O, S or $CONR^3$ and where one or more H atoms is optionally replaced by D, F, Cl, Br, I, CN or NO2, or an aromatic or heteroaromatic ring system having 5 to 60 aromatic ring atoms, which may in each case be substituted by one or more radicals $R^3$, or an aryloxy, aralkoxy, or heteroaryloxy group having 5 to 60 aromatic ring atoms, which is optionally substituted by one or more radicals $R^3$, or a diarylamino group, a diheteroarylamino group, or arylheteroarylamino group having 10 to 40 aromatic ring atoms, which is optionally substituted by one or more radicals $R^3$, or a combination of two or more of these groups, wherein two or more substituents $R^2$ may also form a mono- or polycyclic, aliphatic or aromatic ring system with one another;
$R^3$ is at each occurrence same or different, and $R^3$ includes H, D, F, or an aliphatic, aromatic and/or heteroaromatic hydrocarbon radical having 1 to 20 C atoms, wherein on or more H atoms can be substituted for F, wherein two or more substituents $R^3$ may also form a mono- or polycyclic, aliphatic or aromatic ring system with one another;
$R^4$ is at each occurrence same or different, and $R^4$ includes $Ar^1$, a first moiety comprising a $C_1$-$C_{40}$ alkyl, a $C_1$-$C_{40}$ unsaturated group, a $C_3$-$C_{40}$ cyclic alkyl, or a $C_3$-$C_{40}$ unsaturated cyclic group, the moiety further comprising $R^2$, wherein one or more methylene groups, can include a substitution selected from $R^2C=CR^2$, $C≡C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, or $C(=O)NR^2$, wherein one or more hydrogen atoms can include a substitution selected from D, F, Cl, Br, I, CN, $NO_2$, or $Ar^1$;
$Ar^1$ is at each occurrence same or different, and $Ar^1$ includes an aromatic ring, an aromatic ring system, a hetero-aromatic ring, a hetero-aromatic ring system, or an aromatic hetero-aromatic ring system, wherein $Ar^1$ can include one or more $R^3$ substitution;
m is 0 or 1; and
n is 0 or 1.

2. The compound according to claim 1, wherein $R^4$ includes an aromatic or hetero-aromatic system having 5 to 60 aromatic ring atoms comprising one or more substitution $R^2$.

3. The compound according to claim 1, wherein the compound is of the formula 1a, 1b, or 1c:

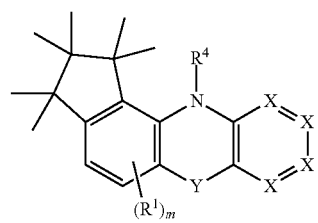

1a

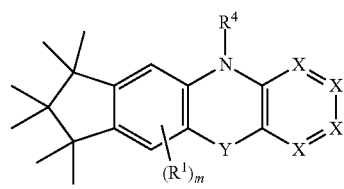

1b

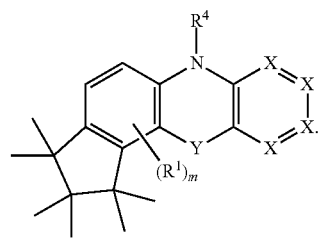

1c

4. The compound according to claim 1 wherein the compound is of the formula 2a, 2b, or 2c:

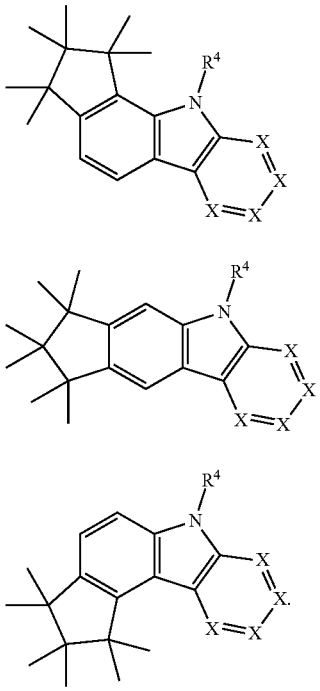

5. The compound according to claim 1 wherein the compound is of the formula 3a, 3b or 3c:

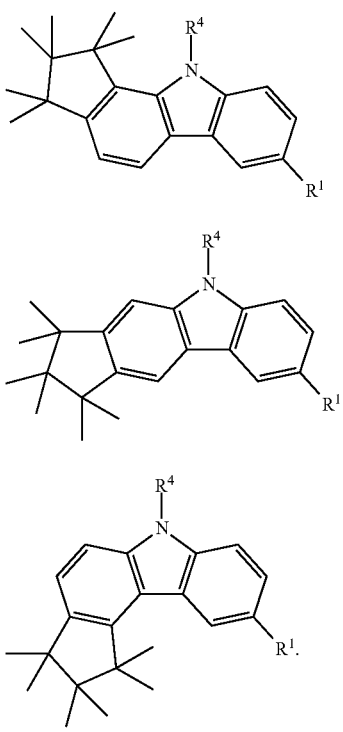

6. The compound according to claim 1, wherein $R^4$ is a phenyl-, biphenyl-, terphenyl-, quarterphenyl-, pyridyl-, pyrimidinyl-, pyrazinyl-, pyridazinyl-, triazinyl-, diarylaminopenyl- or diarylaminobiphenylgroup which can be substituted with one or more $R^2$ that can be same or different in each occurrence.

7. The compound according to claim 1, wherein $R^4$ includes one of the following groups:

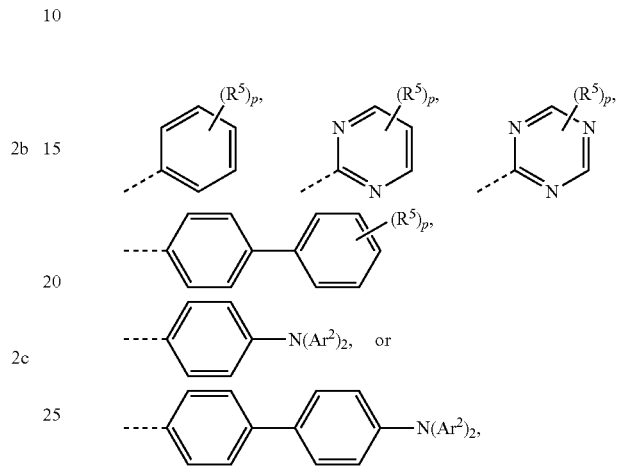

wherein $R^5$ is at each occurrence same or different, and $R^5$ includes H, D, F, Cl, Br, I, CHO, $N(Ar^2)_2$, $C(=O)Ar^2$, $P(=O)(Ar^2)_2$, $S(=O)Ar^2$, $S(=O)_2Ar^2$, $CR^6=CR^6Ar^2$, CN, $NO_2$, $Si(R^6)_3$, $B(OR^6)_2$, $B(R^6)_2$, $B(N(R^6)_2)_2$, $OSO_2R^6$, a straight-chain alkyl, alkoxy, or thioalkoxy group having 1 to 40 C atoms or a branched or cyclic alkyl, alkoxy, or thioalkoxy group having 3 to 40 C atoms, each of which may be substituted by one or more $R^6$, wherein one or more non-adjacent methylene groups may be replaced by $R^6C=CR^6$, $C≡C$, $Si(R^6)_2$, $Ge(R^6)_2$, $Sn(R^6)_2$, $C=O$, $C=S$, $C=Se$, $C=NR^6$, $P(=O)(R^6)$, SO, $SO_2$, $NR^6$, O, S, or $C(=O)NR^6$, and wherein one or more hydrogen atoms can include a substitution selected from D, F, Cl, Br, I, CN, $NO_2$, or an aromatic or heteroaromatic ring system having 5 to 60 aromatic ring atoms, which may in each case be substituted by one or more radicals $R^6$, or an aryloxy or heteroaryloxy group having 5 to 40 aromatic ring atoms, which is optionally substituted by one or more radicals $R^6$, or an aralkyl or heteroaralkyl group having 5 to 40 aromatic ring atoms, which is optionally substituted by one or more radicals $R^6$, or a combination of these systems; wherein two or more substituents $R^5$ together with the atoms to which they are bonded, or two substituents $R^5$, together with the atom to which they are bonded, may also form a mono- or polycyclic, aliphatic or aromatic ring system with one another;

$R^6$ is at each occurrence same or different, and $R^6$ includes H, D, F, or an aliphatic, aromatic and/or heteroaromatic hydrocarbon radical having 1 to 20 C atoms, wherein on or more H atoms can be substituted for F, wherein two or more substituents $R^6$ may also form a mono- or polycyclic, aliphatic or aromatic ring system with one another;

Ar² is at each occurrence same or different, and Ar² includes an aromatic ring, an aromatic ring system, a hetero-aromatic ring, a hetero-aromatic ring system, or an aromatic hetero-aromatic ring system, wherein Ar² can include 5 to 40 ring atoms, wherein Ar² includes one or more R⁶ substitution; and p is 0, 1, 2, 3, 4 or 5.

8. A composition comprising at least one compound according to claim 1 and at least one functional material selected from the group consisting of a hole injection material (HIM), hole transport material (HTM), hole blocking material (HBM), electron injection material (EIM), electron transport material (ETM), electron blocking material (EBM), host material, matrix material, wide band gap material, fluorescent emitter, phosphorescent emitter, n-dopant and p-dopant.

9. The composition according to claim 8, wherein the functional material is a matrix material.

10. The composition according to claim 8, further comprising at least one phosphorescent emitter.

11. The composition according to claim 8, further comprising at least one wide band gap material, wherein the wide band gap material.

12. The composition according to claim 8 wherein the at least one compound is covalently bonded to the oligomer, the dendrimer, or the polymer.

13. A formulation comprising at least one compound according to claim 1 and at least one solvent.

14. An electronic device comprising the compound according to claim 1.

15. The electronic device according to claim 14, wherein the device is selected from the group consisting of organic integrated circuits (OICs), organic field effect transistors (OFETs), organic thin film transistors (OTFTs), organic electroluminescent devices, organic solar cells (OSCs), organic optical detectors and organic photoreceptors.

16. The electronic device according to claim 15, wherein the device is an electroluminescent device selected from the group consisting of organic light emitting transistors (OLETs), organic field quenching devices (OFQDs), organic light emitting electrochemical cells (OLECs, LECs, LEECs), organic laser diodes (O-Laser) and organic light emitting diodes (OLEDs).

17. The electronic device according to claim 15 for use in medicine for phototherapy.

18. The electronic device to claim 15 for cosmetic use for irradiation of human and animal skin.

19. A method for preparing the electronic device according to claim 15, the method including depositing at least one organic layer of the device by vapor deposition or from solution.

20. A compound according to the formula 1a or 1c,

1a

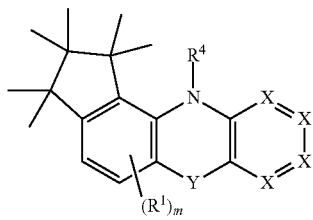

-continued

1c

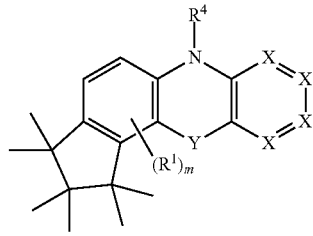

wherein:

Y is at each occurrence same or different and selected from C(R¹)₂, N(R¹), C(=O), C(=S), O, or S;

X is at each occurrence same or different, and X includes CR¹ or N;

R¹ is at each occurrence same or different, and R¹ includes H, D, F, Cl, Br, I, CHO, N(Ar¹)₂, C(=O)Ar¹, P(=O)(Ar¹)₂, S(=O)Ar¹, S(=O)₂Ar¹, CR²=CR²Ar¹, CN, NO₂, Si(R²)₃, B(OR²)₂, B(R²)₂, B(N(R²)₂)₂, OSO₂R², a straight-chain alkyl, alkoxy, or thioalkoxy group having 1 to 40 C atoms or a branched or cyclic alkyl, alkoxy, or thioalkoxy group having 3 to 40 C atoms, each of which may be substituted by one or more R², wherein one or more non-adjacent methylene groups may be replaced by R²C=CR², C≡C, Si(R²)₂, Ge(R²)₂, Sn(R²)₂, C=O, C=S, C=Se, C=NR², P(=O)(R²), SO, SO₂, NR², O, S, or C(=O)NR², and wherein one or more hydrogen atoms can include a substitution selected from D, F, Cl, Br, I, CN, NO₂, or an aromatic or heteroaromatic ring system having 5 to 60 aromatic ring atoms, which may in each case be substituted by one or more radicals R², or an aryloxy or heteroaryloxy group having 5 to 40 aromatic ring atoms, which is optionally substituted by one or more radicals R², or an aralkyl or heteroaralkyl group having 5 to 40 aromatic ring atoms, which is optionally substituted by one or more radicals R², or a combination of these systems; wherein two or more substituents R¹ together with the atoms to which they are bonded, or two substituents R¹, together with the atom to which they are bonded, may also form a mono- or polycyclic, aliphatic or aromatic ring system with one another;

R² is at each occurrence same or different, and R² includes H, D, F, Cl, Br, I, N(R³)₂, CN, NO₂, Si(R³)₃, B(OR³)₂, C(=O)R³, P(=O)(R³)₂, S(=O)R³, S(=O)₂R³, OSO₂R³, a straight-chain alkyl, alkoxy or thioalkoxy group having 1 to 40 C atoms or a straight-chain alkenyl or alkynyl having 2 to 40 C atoms or a branched or cyclic alkyl, alkenyl, alkynyl, alkoxy, alkylalkoxy, or thioalkoxy group having 3 to 40 C atoms, each of which is optionally substituted by one or more radicals R³, where one or more non-adjacent CH₂ groups is optionally replaced by R³C=CR³, C≡C, Si(R³)₂, Ge(R³)₂, Sn(R³)₂, C=O, C=S, C=Se, C=NR³, P(=O)(R³), SO, SO₂, NR³, O, S or CONR³ and where one or more H atoms is optionally replaced by D, F, Cl, Br, I, CN or NO₂, or an aromatic or heteroaromatic ring system having 5 to 60 aromatic ring atoms, which may in each case be substituted by one or more radicals R³, or an aryloxy, aralkoxy, or heteroaryloxy group having 5 to 60 aromatic ring atoms, which is optionally substituted by one or more radicals R³, or a diarylamino group, a diheteroarylamino group, or arylheteroarylamino group having 10 to 40 aromatic ring atoms, which is optionally substituted by one or more radicals $R^3$, or a combination of two or more of these groups, wherein two or more substituents $R^2$ may also form a mono- or polycyclic, aliphatic or aromatic ring system with one another;

$R^3$ is at each occurrence same or different, and $R^3$ includes H, D, F, or an aliphatic, aromatic and/or heteroaromatic hydrocarbon radical having 1 to 20 C atoms, wherein on or more H atoms can be substituted for F, wherein two or more substituents $R^3$ may also form a mono- or polycyclic, aliphatic or aromatic ring system with one another;

$R^4$ is at each occurrence same or different, and $R^4$ includes $Ar^1$, a first moiety comprising a $C_1$-$C_{40}$ alkyl, a $C_1$-$C_{40}$ unsaturated group, a $C_3$-$C_{40}$ cyclic alkyl, or a $C_3$-$C_{40}$ unsaturated cyclic group, the moiety further comprising $R^2$, wherein one or more methylene groups, can include a substitution selected from $R^2C=CR^2$, $C\equiv C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, or $C(=O)NR^2$, wherein one or more hydrogen atoms can include a substitution selected from D, F, Cl, Br, I, CN, $NO_2$, or $Ar^1$;

$Ar^1$ is at each occurrence same or different, and $Ar^1$ includes an aromatic ring, an aromatic ring system, a hetero-aromatic ring, a hetero-aromatic ring system, or an aromatic hetero-aromatic ring system, wherein $Ar^1$ can include one or more $R^3$ substitution;

m is 0 or 1; and n is 0 or 1.

\* \* \* \* \*